(12) United States Patent
Fritzer et al.

(10) Patent No.: US 12,564,625 B2
(45) Date of Patent: *Mar. 3, 2026

(54) METHOD OF PRODUCING PHARMACEUTICAL COMPOSITIONS COMPRISING IMMUNOGENIC CHIKUNGUNYA VIRUS CHIKV-Δ5nsP3

(71) Applicant: Valneva SE, Nantes (FR)

(72) Inventors: Andrea Fritzer, Vienna (AT); Andreas Meinke, Pressbaum (AT); Urban Lundberg, Pressbaum (AT); Mario Nebenführ, Vienna (AT); Jürgen Heindl-Wruss, Vienna (AT); Robert Schlegl, Siegenfeld (AT); Arnaud Leon, Nantes (FR)

(73) Assignee: Valneva SE, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,777

(22) Filed: May 6, 2024

(65) Prior Publication Data

US 2025/0073326 A1     Mar. 6, 2025

Related U.S. Application Data

(63) Continuation of application No. 17/935,490, filed on Sep. 26, 2022, now Pat. No. 12,011,477, which is a
(Continued)

(30) Foreign Application Priority Data

Sep. 21, 2017     (EP) ..................................... 17192374

(51) Int. Cl.
    *A61K 39/12*        (2006.01)
    *A61K 9/00*         (2006.01)
    (Continued)

(52) U.S. Cl.
    CPC ........... *A61K 39/12* (2013.01); *A61K 9/0019* (2013.01); *A61K 9/19* (2013.01); *A61P 31/14* (2018.01);
    (Continued)

(58) Field of Classification Search
    None
    See application file for complete search history.

(56) References Cited

U.S. PATENT DOCUMENTS 6,309,650 B1    10/2001  Kim et al.
7,871,814 B2    1/2011   Andino-Pavlovsky et al.
(Continued)

FOREIGN PATENT DOCUMENTS

CN          105749268  A      7/2016
WO     WO 1999/011762  A1      3/1999
(Continued)

OTHER PUBLICATIONS

[No Author Listed], Centers for Disease Control and Prevention. Ingredients of vaccines fact sheet; continuously updated; https://www.cdc.gov/vaccines/vac-gen/additives.htm.
(Continued)

*Primary Examiner* — Shanon A. Foley
(74) *Attorney, Agent, or Firm* — Wolf, Greenfield & Sacks, P.C.

(57) ABSTRACT

The present invention relates to a process for producing an immunogenic live attenuated Chikungunya virus, as well as pharmaceutical compositions comprising the same.

20 Claims, 23 Drawing Sheets

Specification includes a Sequence Listing.

Related U.S. Application Data continuation of application No. 16/641,012, filed as application No. PCT/EP2018/075392 on Sep. 19, 2018, now Pat. No. 11,484,587.

(51) Int. Cl.

| | |
|---|---|
| *A61K 9/19* | (2006.01) |
| *A61P 31/14* | (2006.01) |
| *C07K 14/005* | (2006.01) |
| *C12N 7/00* | (2006.01) |
| *A61K 39/00* | (2006.01) |

(52) U.S. Cl.

CPC .............. *C07K 14/005* (2013.01); *C12N 7/00* (2013.01); *A61K 2039/5254* (2013.01); *A61K 2039/54* (2013.01); *C12N 2770/36121* (2013.01); *C12N 2770/36122* (2013.01); *C12N 2770/36123* (2013.01); *C12N 2770/36134* (2013.01)

(56) References Cited

U.S. PATENT DOCUMENTS

| | | | |
|---|---|---|---|
| 8,765,148 | B2 | 7/2014 | Wizel et al. |
| 8,865,184 | B2 | 10/2014 | Ella et al. |
| 9,353,353 | B2 | 5/2016 | Nable et al. |
| 9,499,588 | B2 | 11/2016 | Mason et al. |
| 10,086,061 | B2 | 10/2018 | Thomas et al. |
| 10,537,630 | B2 | 1/2020 | Barbero Calzado et al. |
| 10,660,950 | B2 | 5/2020 | Barbero Calzado et al. |
| 10,744,194 | B2 | 8/2020 | Barbero Calzado et al. |
| 11,207,397 | B2 | 12/2021 | Barbero Calzado et al. |
| 11,357,846 | B2 * | 6/2022 | Fritzer ................. A61K 9/0019 |
| 11,406,700 | B2 | 8/2022 | Barbero Calzado et al. |
| 11,484,587 | B2 * | 11/2022 | Fritzer ..................... C12N 7/00 |
| 11,524,064 | B2 | 12/2022 | Barbero Calzado et al. |
| 12,011,477 | B2 * | 6/2024 | Fritzer ................. A61K 9/0019 |
| 2011/0171249 | A1 | 7/2011 | Frolov et al. |
| 2012/0003266 | A1 | 1/2012 | Nable et al. |
| 2014/0086953 | A1 * | 3/2014 | Brown ................... A61K 38/00 |
| | | | 435/235.1 |
| 2018/0362936 | A1 | 12/2018 | Barbero Calzado et al. |
| 2018/0362937 | A1 | 12/2018 | Barbero Calzado et al. |
| 2018/0369359 | A1 | 12/2018 | Barbero Calzado et al. |
| 2018/0371027 | A1 | 12/2018 | Barbero Calzado et al. |
| 2019/0008945 | A1 | 1/2019 | Barbero Calzado et al. |
| 2020/0197506 | A1 | 6/2020 | Barbero Calzado et al. |
| 2020/0368342 | A1 | 11/2020 | Barbero Calzado et al. |
| 2021/0322534 | A1 | 10/2021 | Fritzer et al. |
| 2022/0016230 | A1 | 1/2022 | Fritzer et al. |
| 2023/0056142 | A1 | 2/2023 | Barbero Calzado et al. |
| 2023/0293661 | A1 | 9/2023 | Fritzer et al. |

FOREIGN PATENT DOCUMENTS

| | | |
|---|---|---|
| WO | WO 2001/092552 A2 | 12/2001 |
| WO | WO 2008/026225 A2 | 3/2008 |
| WO | WO 2010/062396 A2 | 6/2010 |
| WO | WO 2013/083726 A1 | 6/2013 |
| WO | WO 2016/145149 A1 | 9/2016 |
| WO | WO 2017/109225 A1 | 6/2017 |

OTHER PUBLICATIONS

[No Author Listed], Japanese Encephalitis Vaccine. Centers for Disease Control and Prevention, 2016. Retrieved from https://www.cdc.gov/japaneseencephalitis/vaccine/ on Jun. 16, 2016.

[No Author Listed], Pan-American Health Organization. 2015. Number of Reported Cases of Chikungunya Fever in the Americas, by Country or Territory 2013-2014, Cumulative Cases (Updated Oct. 23, 2015).

[No Author Listed], Protamine sulfate. Wikimedia Foundation, Inc., 2015. Retrieved from https://en.wikipedia.org/wiki/Protamine_sulfate; updated Sep. 30, 2015 on Nov. 26, 2015.

[No Author Listed], Valneva Announces Successful Generation of a Highly-purified Zika Vaccine Candidate Using its FDA-EMA Approved Japanese Encephalitis Platform. Press release Jul. 7, 2016.

[No Author Listed], Valneva Reports Excellent Final Phase 1 Results for its Chikungunya Vaccine Candidate, Confirms Plans. Press release. Nov. 18, 2019.

[No Author Listed], Valneva Reports Further Positive Results for Its Chikungunya Vaccine Candidate. Saint Herblain, France. May 22, 2019. 4 pages.

[No Author Listed], Valneva Reports Positive Phase 1 Interim Results for Its Chikungunya Vaccine Candidate. Saint Herblain, France. Jan. 7, 2019. 4 pages.

[No Author Listed], Valneva Reports Positive 24-Month Antibody Persistence Data for its Single-Shot Chikungunya Vaccine IXCHIQ®. VALNEVA SE. Dec. 4, 2023. 5 pages.

[No Author Listed], World Health Organization, 2016 Zika Virus Fact Sheet 2016. Retrieved from http://www.who.int/mediacentre/factsheets/zika/en/ on Mar. 11, 2016.

[No Author Listed], World Health Organization, 2016. Zika Situation Report Feb. 5, 2016.

[No Author Listed], Zika virus, strain H/PF/2013. European virus archive, 2016.

Abbink et al., Durability and correlates of vaccine protection against Zika virus in rhesus monkeys. Sci. Transl. Med. 2017;9:eaao4163.

Altschul et al., Basic Local Alignment Search Tool. J. Mol. Biol. 1990;215:403-410.

Altschul et al., Gapped BLAST and PSI-BLAST: a new generation of protein database search programs. Nuc. Acids Res. 1997;25(17):3389-3402.

Anez et al., Passage of dengue virus type 4 vaccine candidates in fetal rhesus lung cells selects heparin-sensitive variants that result in loss of infectivity and immunogenicity in rhesus macaques. J Virol. Oct. 2009;83(20):10384-94. doi: 10.1128/JVI.01083-09. Epub Aug. 5, 2009.

Athmaram et al., A two step purification strategy for Chikungunya virions purification using sucrose buoyant density gradient separation. J Virology Res. 2013;2(1):18-21.

Aubry et al., Inactivation of Zika virus in plasma with amotosalen and ultraviolet A illumination. Transfusion. Jan. 2016;56(1):33-40. doi: 10.1111/trf.13271. Epub Aug. 18, 2015.

Baronti et al., Complete Coding Sequence of Zika Virus from a French Polynesia Outbreak in 2013. Genome Announc. May-Jun. 2014; 2(3):e00500-14. Abstract.

Bender et al., Zika Virus Vaccine Candidate VLA1601: Cooperation VALNEVA & EMERGENT, Presentation at World Vaccine Congress Apr. 4, 2018.

Bender, Chikungunya Virus Vaccine Candidate VALNEVA's VLA1553. World Vaccine Conference 2019. Washington, D.C.. Apr. 16, 2019. 43 pages.

Chroboczek et al., Virus-like particles as vaccine. Acta Biochim Pol. 2014;61(3):531-9. Epub Sep. 18, 2014.

Cohen, Infectious Disease. The race for a Zika vaccine is on. Science. Feb. 5, 2016;351(6273):543-4. doi: 10.1126/science.351.6273.543.

Cox et al., Predicting Zika virus structural biology:Challenges and opportunities for intervention. Antivir Chem Chemother. Aug. 2015;24(3-4):118-26. doi: 10.1177/2040206616653873. Epub Jun. 13, 2016.

Dowall et al., A susceptible mouse model for Zika virus infection. PLOS Neglected Tropical Diseases.10(5):e0004658. May 5, 2016. DOI:10.1371/journal.pntd.0004658.

Eckels et al., Chikungunya virus vaccine prepared by Tween-ether extraction. Appl Microbiol. Feb. 1970;19(2):321-5.

Edelman et al., Phase II safety and immunogenicity study of live chikungunya virus vaccine TSI-GSD-218. Am J Trop Med Hyg. Jun. 2000;62(6):681-5. doi: 10.4269/ajtmh.2000.62.681.

Fritsche et al., Vaccine hypersensitivity—update and overview. Swiss Med Wkly. 2010;140(17-18):238-246.

Garcia-Arriaza et al., A novel poxvirus-based vaccine, MVA-CHIKV, is highly immunogenic and protects mice against chikungunya infection. J Virol. Mar. 2014;88(6):3527-47. doi: 10.1128/JVI.03418-13. Epub Jan. 8, 2014.

(56)                References Cited

OTHER PUBLICATIONS

Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.

Geradin et al., Chikungunya virus-associated encephalitis: A cohort study on La Réunion Island. 2005-2009. Neurology. 86(1):94-102.

Gubler et al., Fields Virology. Knipe DM, Howley PM, editors. Lippincott-Raven Publishers; Philadelphia: 2007:1153-1252.

Haddow et al., Genetic Characterization of Zika Virus Strains: Geographic Expansion of the Asian Lineage. PLoS Negl Trop Dis 6(2): e1477. doi:10.1371/journal.pntd.0001477.

Hallengard et al., Novel Attenuated Chikungunya Vaccine Candidates Elicit Protective Immunity in C57BL/6 mice. J. Virology 88(5):2858-2866.

Hallengard et al., Prime-Boost Immunization Strategies against Chikungunya Virus. J. Virology. 88(22):13333-13343.

Hombach et al., Report on a WHO consultation on immunological endpoints for evaluation of new Japanese encephalitis vaccines, WHO, Geneva, Sep. 2-3, 2004. Vaccine. 2005; 23(45):5205-5211.

Hutornojs et al., Comparison of ultracentrifugation methods for concentration of recombinant alphaviruses: sucrose and iodixanol cushions. Environmental Experimental Biology. 2012;10:117-123.

Katoh et al., Recent developments in the MAFFT multiple sequence alignment program. Briefings in Bioinformatics. 2008;9(4):286-298.

Kim et al., Design of Chimeric Alphaviruses with a Programmed, Attenuated, Cell Type-Restricted Phenotype. J Virol. 2011;85(9):4363-4376.

Konishi et al., Studies on structural proteins of Chikungunya Virus. I. Separation of three species of proteins and their preliminary characterization. Microbiol Immunol. 1980;24(5):419-28. doi: 10.1111/j.1348-0421.1980.tb02846.x.

Larkin et al., Clustal W and Clustal X version 2.0. Bioinformatics. 2007;23(21):2947-2948.

Larocca et al., Vaccine protection against Zika virus from Brazil. Nature. 2016;536:474-478. doi: 10.1038/nature18952. Methods.

Liljestrom et al., A new generation of animal cell expression vectors based on the Semliki Forest virus replicon. Biotechnology (N Y). Dec. 1991;9(12):1356-61. doi: 10.1038/nbt1291-1356.

Lindenbach et al., Fields Virology. Knipe DM, Howley PM, editors. Lippincott-Raven Publishers; Philadelphia: 2007;1101-1152.

Malone et al., Zika Virus: Medical Countermeasure Development Challenges. PLoS Negl Trop Dis. 2016;10(3):e0004530. doi:10.1371/journal.pntd.0004530.

Modjarrad et al., Preliminary aggregate safety and immunogenicity results from three trials of a purified inactivated Zika virus vaccine candidate: phase 1, randomised, double-blind, placebo-controlled clinical trials. Dec. 4, 2017.

Monath, Yellow fever: an update. Lancet Infect Dis. 2001;1(1):11-20.

Needleman et al., A general method applicable to the search for similarities in the amino acid sequence of two proteins. J. Mol. Biol. 1970;48(3):443-453.

Patkar et al., Yellow Fever virus NS3 plays an essential role in virus assembly independent of its known enzymatic functions. J Virol. Apr. 2008;82(7):3342-52. doi: 10.1128/JVI.02447-07. Epub Jan. 16, 2008.

Pearson et al., Improved tools for biological sequence comparison. Proc. Natl. Acad. Sci. USA. 1988;85(8):2444-8.

Pellerin, Walter Reed Scientists Test Zika Vaccine Candidate. U.S. Department of Defense. Jun. 9, 2016.

Pinto et al., A Temporal Role of Type I Interferon Signaling in CD8+ T Cell Maturation during Acute West Nile Virus Infection. PLoS Pathog. Dec. 2011;7(12):e1002407.

Plevka et al., Maturation of flaviviruses starts from one or more icosahedrally independent nucleation centres EMBO reports. 2011;12(6):602-606.

Pohjala et al., Inhibitors of alphavirus entry and replication identified with a stable Chikungunya replicon cell line and virus-based assays. PLoS One. 2011;6(12):e28923. doi: 10.1371/journal.pone.0028923. Epub Dec. 19, 2011. 13 pages.

Powers et al., Re-emergence of Chikungunya and O'nyong-nyong viruses: evidence for distinct geographical lineages and distant evolutionary relationships. J Gen Virol. Feb. 2000;81(Pt 2):471-9. doi: 10.1099/0022-1317-81-2-471.

Reed et al., A simple method of estimating fifty percent endpoints. American J Hygiene. May 1938;27:493-497.

Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.

Roques et al., Attenuated and vectored vaccines protect nonhuman primates against Chikungunya virus. JCI Insight. Mar. 23, 2017;2(6):e83527. doi: 10.1172/jci.insight.83527.

Rozen-Gagnon et al., Alphavirus Mutator Variants Present Host-Specific Defects and Attenuation in Mammalian and Insect Models, PLOS Pathogens, 10(1):e1003877.

Schlegl et al., Influence of elemental impurities in aluminum hydroxide adjuvant on the stability of inactivated Japanese Encephalitis vaccine, IXIARO®. Vaccine. 2015;33(44):5989-5996.

Shustov et al., Efficient, trans-complementing packaging systems for chimeric, pseudoinfectious dengue 2/yellow fever viruses. Virology. Apr. 25, 2010;400(1):8-17. doi: 10.1016/j.virol.2009.12.015.

Simizu et al., Structural Proteins of Chikungunya Virus, J Virol. 1984;51(1): 254-258.

Smith et al., Comparison of Biosequences. Adv Appl Math. 1981;2:482-489.

Srivastava et al., A purified inactivated Japanese encephalitis virus vaccine made in vero cells. Vaccine. 2001; 19:4557-4565.

Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.

Vega-Rua et al., Chikungunya Virus Transmission Potential by Local Aedes Mosquitoes in the Americas and Europe. PLOS Neglected Tropical Diseases. 2015;9(5): e0003780.

Waterhouse et al., Jalview Version 2—a multiple sequence alignment editor and analysis workbench. Bioinformatics. 2009;25(9):1189-1191.

Way et al., Comparative Studies of some African Arboviruses in Cell Culture and in Mice, J Gen. Virol. 1976;30:123-130.

Weaver, Arrival of Chikungunya Virus in the New Word: Prospects for Spread and Impact on Public Health. PLoS Negl Trop Dis. 2014;8(6):e2921. doi:10.1371/journal.pntd.0002921.

* cited by examiner

VLA1553-CHIKV-Δ5nsP3 Genome
11673bp

| | Groups for subcutaneous immunization of C57Bl/6 mice | | | | |
|---|---|---|---|---|---|
| | Group 1 | Group 3 | Group 5 | Group 6 | Group 7 |
| Formulation ratio of P3 and P5B-07 (E168K) | P3:E168K 1:0.1 | P3:E168K 1:1 | P3:E168K 1:10 | P3 | P5B-7 |
| Reference sequence | G | G | G | G | G |
| Heterogeneity | G>A | G=A | G<A | G>A | A |
| Chromatogram | | | | | |

FIG. 15A

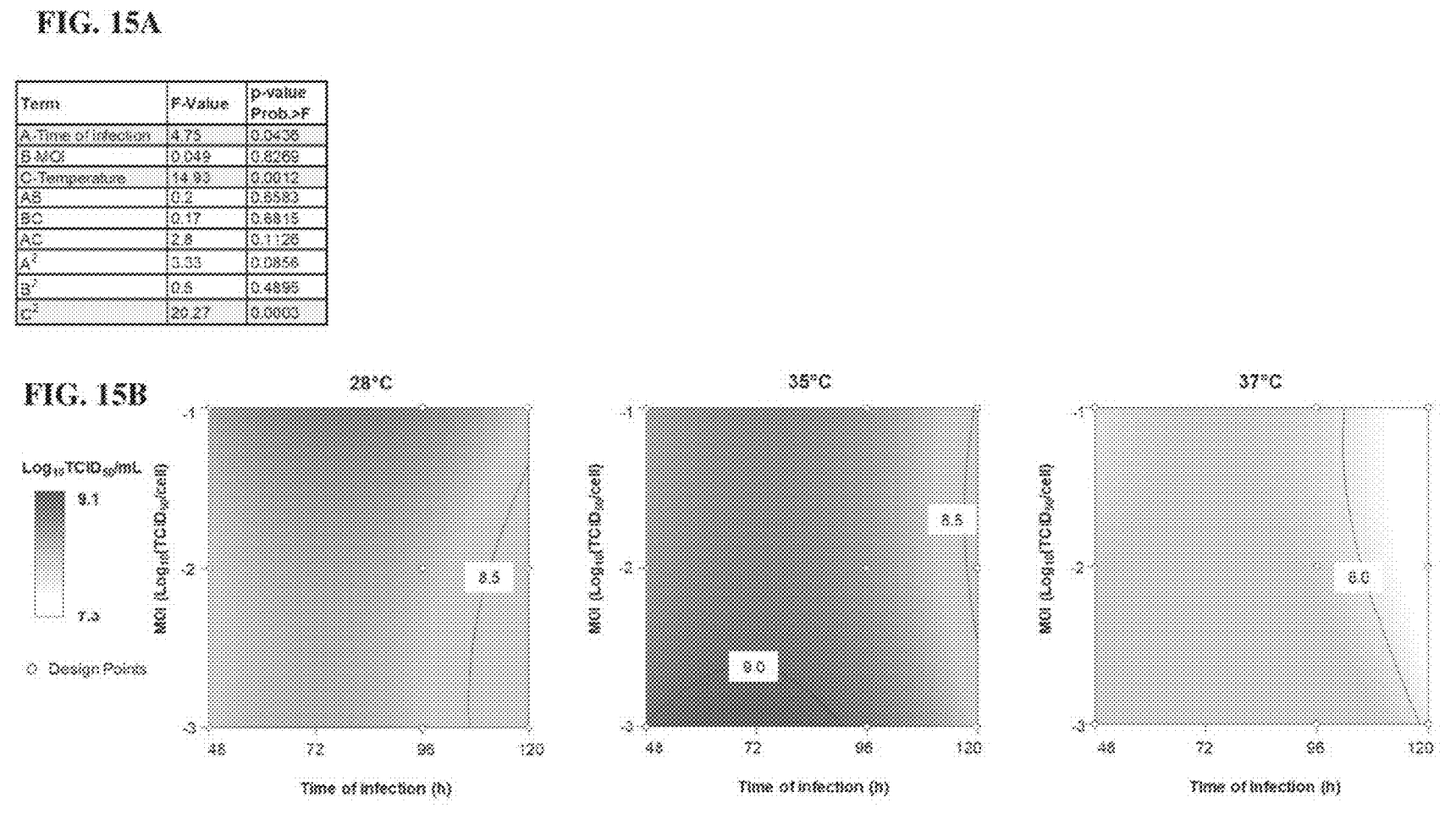

| Term | F-Value | p-value Prob>F |
|---|---|---|
| A-Time of infection | 4.75 | 0.0438 |
| B-MOI | 0.049 | 0.8269 |
| C-Temperature | 4.93 | 0.0012 |
| AB | 0.2 | 0.6583 |
| BC | 0.17 | 0.6815 |
| AC | 2.8 | 0.1126 |
| A² | 3.33 | 0.0858 |
| B² | 0.5 | 0.4896 |
| C² | 20.27 | 0.0003 |

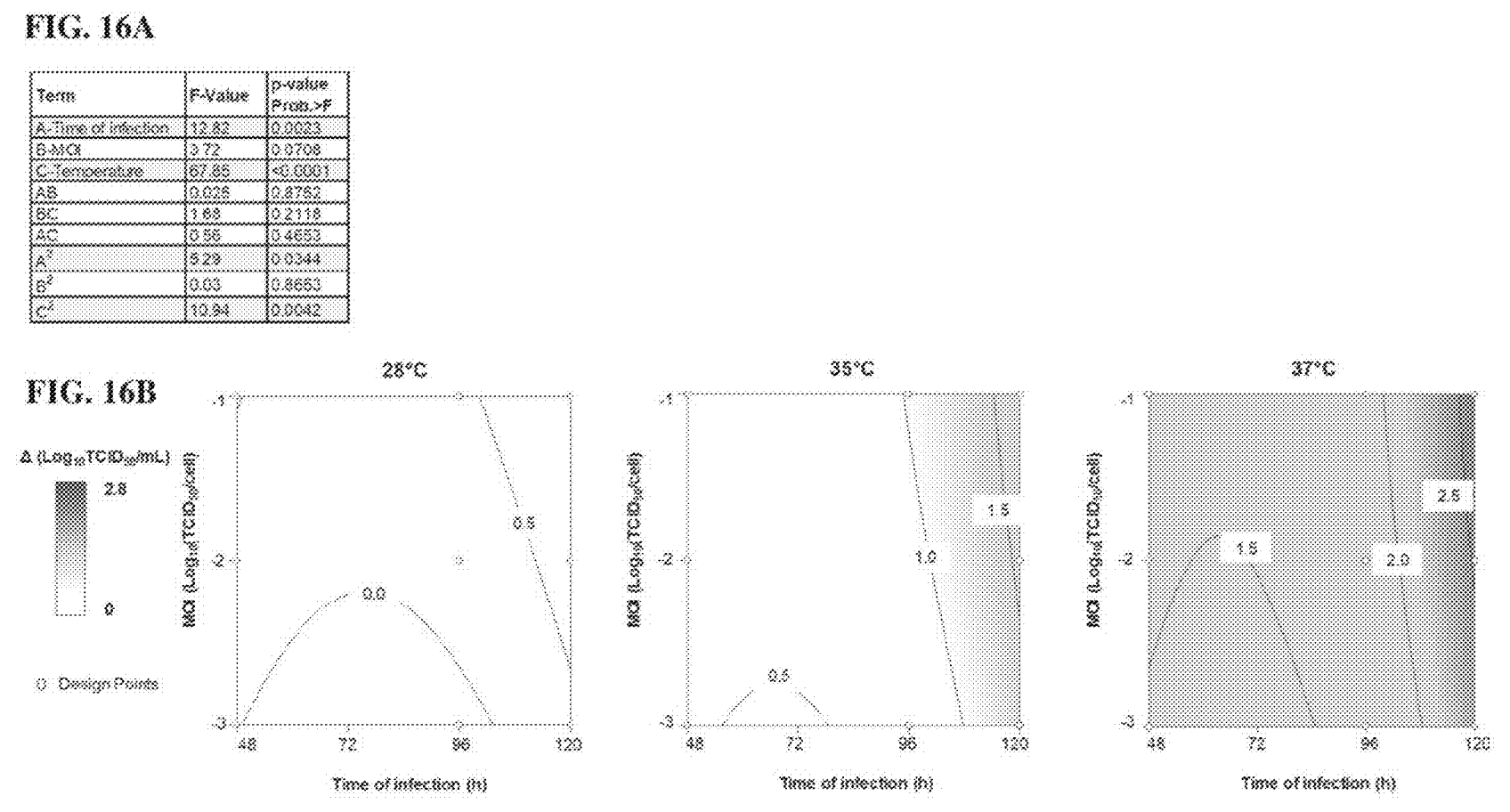

| Term | F-Value | p-value Prob.>F |
|---|---|---|
| A: Time of infection | 9.83 | 0.0041 |
| B: MOI | 3.72 | 0.0708 |
| C: Temperature | 67.85 | <0.0001 |
| AB | 0.026 | 0.8750 |
| BC | 1.68 | 0.2116 |
| AC | 0.56 | 0.4653 |
| A² | 5.29 | 0.0344 |
| B² | 0.03 | 0.8653 |
| C² | 10.94 | 0.0442 |

FIG. 16B

Pos. 8882 (E188K)

| Term | F-Value | p-value Prob.>F |
|------|---------|-----------------|
| A-MOI | 17.65 | 0.0057 |
| B-Temperature | 2.5 | 0.1651 |

Pos. 9119 (E247K)

| Term | F-Value | p-value Prob.>F |
|------|---------|-----------------|
| A-MOI | 2.42 | 0.1712 |
| B-Temperature | 61.73 | 0.0002 |

Pos. 9649 (Silent)

| Term | F-Value | p-value Prob.>F |
|------|---------|-----------------|
| A-MOI | 32.19 | 0.0024 |
| B-Temperature | 10.15 | 0.0249 |
| AB | 8.74 | 0.0317 |

METHOD OF PRODUCING PHARMACEUTICAL COMPOSITIONS COMPRISING IMMUNOGENIC CHIKUNGUNYA VIRUS CHIKV-Δ5nsP3

RELATED APPLICATIONS

This application is a Continuation of U.S. application Ser. No. 17/935,490, which is a Continuation of U.S. application Ser. No. 16/641,012, filed Feb. 21, 2020, entitled "METHOD OF PRODUCING PHARMACEUTICAL COMPOSITIONS COMPRISING IMMUNOGENIC CHIKUNGUNYA VIRUS CHIKV-DELTA5NSP3", issued as U.S. Pat. No. 11,484,587, which is a national stage filing under 35 U.S.C. § 371 of International Patent Application Serial No. PCT/EP2018/075392, filed Sep. 19, 2018. The entire contents of these applications are incorporated herein by reference in their entirety.

REFERENCE TO AN ELECTRONIC SEQUENCE LISTING

The contents of the electronic sequence listing (I042270131US03-SEQ-NTJ.xml; Size: 76,265 bytes; and Date of Creation: Jan. 2, 2024) are herein incorporated by reference in their entirety.

FIELD OF THE INVENTION

The invention relates to a process for producing an immunogenic live attenuated Chikungunya virus, as well as pharmaceutical compositions comprising the same.

BACKGROUND OF THE INVENTION

Chikungunya virus (CHIKV) is a positive-sense, single-stranded RNA virus from the genus *Alphavirus*, family Togaviridae. Chikungunya virus disease is mainly an outbreak disease and is associated with high attack rates. The virus is transmitted to humans via a mosquito vector and causes fever, rash, fatigue and severe polyarthralgia. Infections with CHIKV generally resolve spontaneously and are not usually fatal, except in rare cases involving CNS infection, where the death rate is between 10 to 30 percent. Particularly at risk for CHIKV CNS disease are infants under one year and adults over 65 years, with an infection rate 25-fold and 6-fold higher than the general population, respectively. The rate of persistent disabilities in children following CHIKV encephalitis is estimated at between 30 and 45 percent (Gerardin P, et al. Chikungunya virus-associated encephalitis A cohort study on La Réunion Island, 2005-2009 (2016) Neurology 86:1-9). Furthermore, about 30 percent of all Chikungunya patients experience arthralgia for months to years after recovery. In some cases, neurological, renal, cardiac, respiratory or hepatic complications can occur.

Currently no vaccines or medications are available for the prevention or treatment of Chikungunya virus disease. Outbreaks in the past have occurred mainly in Africa, but the East-Central South African (ECSA) genotype has recently expanded its geographical range, resulting in outbreaks in India, Asia, and even temperate Europe (Weaver, S., Arrival of Chikungunya Virus in the New World: Prospects for Spread and Impact on Public Health (2014) PLOS Neglected Tropical Diseases 8(6): e2921). Although CHIKV has been repeatedly imported into the Americas since 1995, autochthonous transmission had not been reported until 2013 in the Caribbean. By 2015, the epidemic had spread to the mainland and caused upwards of one million suspected cases in 27 countries in the Americas (Pan-American Health Organization (2015) Number of Cumulative Cases of Chikungunya Fever in the Americas). Further epidemics may been aided in part by the spread of the CHIKV mosquito vector into non-endemic regions, as well as the ability of CHIKV to adapt to local mosquito species (Vega-Rua A, et al., Chikungunya Virus Transmission Potential by Local Aedes Mosquitoes in the Americas and Europe (2015) PLOS Neglected Tropical Diseases DOI: 10.1371/journal.pntd.0003780). The high rate of contagion of Chikungunya virus, its geographical spread, and its potential for long-lasting complications underscore the need for developing preventative measures, such as vaccines.

Vaccines against Chikungunya virus may comprise live attenuated CHIKV particles; i.e., live CHIKV particles which have been altered to reduce virulence, but still maintain immunogenicity. One example of an attenuated CHIKV contains a deletion mutation in the non-structural protein 3 (CHIKV-Δ5nsP3; see FIG. 2). CHIKV-Δ5nsP3 has been shown to confer protective immunity in mice (Hallengärd D, et al. Novel attenuated Chikungunya vaccine candidates elicit protective immunity in C57Bl/6 mice (2014) J. Virol. 88:2858-2866) and non-human primates (Roques P, et al. Attenuated and vectored vaccines protect non-human primates against Chikungunya virus (2017) J. Clin. Invest. Insight 2(6):e83527). These preliminary in vivo studies in mice and non-human primates were done with CHIKV-Δ5nsP3 virus produced on BHK-21 cells—a cell type generally not favored for the production of human vaccines. It would be necessary, therefore, as disclosed herein, to adapt CHIKV-Δ5nsP3 virus production to a more suitable cell culture platform. Such adaptation is not a trivial process; for example, it is known in the art that the adaptation of viruses to a particular host cell can lead to mutations that change the surface charge of the virus particles. Such acquired mutations can serve to attenuate viruses; in fact, serial passaging has been used to develop such attenuated virus particles that are used in many vaccines against viruses. With regard to CHIKV, it has been shown that repeated in vitro passaging of virulent wild-type Chikungunya virus can lead to certain point mutations, resulting in partial or complete attenuation of the virus (Gardner C L, et al., Deliberate Attenuation of Chikungunya Virus by Adaptation to Heparan Sulfate-Dependent Infectivity: A Model for Rational Arboviral Vaccine Design (2014) PLOS Neglected Tropical Diseases 8(2): e2719).

It has now surprisingly been found that certain point mutations resulting in loss of immunogenicity can occur early during the cell substrate adaptation process of the attenuated CHIKV-Δ5nsP3, making control or reduction of said point mutations an essential consideration for the production of a successful vaccine candidate. Thus, the current invention provides a process with well-defined parameters for the propagation of the CHIKV-Δ5nsP3 vaccine candidate, allowing production of highly immunogenic virus particles, while simultaneously achieving high production titers in cell culture suitable for industrial application.

SUMMARY OF THE INVENTION

The present invention relates to a pharmaceutical composition comprising a sufficient amount of immunogenic Chikungunya virus to elicit a neutralizing immune response in a subject; i.e., an immune response that is protective against infection with and/or disease caused by Chikungunya virus. In particular, the invention provides a pharmaceutical composition comprising live attenuated CHIKV-Δ5nsP3 particles wherein the percentage of said viral particles with immunogenicity-reducing mutations, particularly immunogenicity-reducing mutations in the E2 protein, are minimized. The disclosure further provides a process for producing a pharmaceutical composition comprising a live attenuated CHIKV-Δ5nsP3, wherein the process minimizes the presence of immunogenicity-reducing mutations in the viral genome, particularly mutations at E168 of viral E2 protein and/or other E2 residues and/or residues in other structural or non-structural CHIKV proteins. The current disclosure further provides pharmaceutical compositions comprising an immunogenic live attenuated Chikungunya virus obtainable by the process of the invention.

Efforts to develop a vaccine against Chikungunya virus are currently underway. One of the most advanced vaccine candidates provides a chimeric construct in a measles virus platform (see themisbio.com/#/news). The vaccine, currently in Phase 2 trials, is delivered in two doses (clinicaltrials.gov/ct2/show/NCT02861586?term=themis&recrs=a&rank=2). A one-shot vaccine would represent a distinct advantage in the field.

Accordingly, in one embodiment, it is an object of the current invention to provide a stable, well-defined, safe and effective pharmaceutical composition such as, e.g. a vaccine, against Chikungunya virus, preferably an improved vaccine conferring protection with only one vaccination; i.e., a so called "one-shot" vaccine at industrial scale using common cell substrates, to provide processes to generate such a stable, well-defined, safe and effective vaccine and methods and uses for said stable, well-defined safe and effective vaccine.

BRIEF DESCRIPTION OF THE DRAWINGS

The accompanying drawings are not intended to be drawn to scale. The Figures are illustrative only and are not required for enablement of the disclosure. For purposes of clarity, not every component may be labeled in every drawing. In the drawings:

(FIG. 3A) Design schematic of synthesized polynucleotide fragments covering the full CHIKV-Δ5nsP3 genome. (FIG. 3B) Cloning strategy for assembly of CHIKV-Δ5nsP3 genome in pMA plasmid. 1. Cloning of CHIKV-Δ5nsP3 fragment 2 into pMA containing fragment 1 (pMA fragment 1) via EcoRI and PacI. 2. Assembly of fragment 4 and fragment 3 via ClaI and PacI.

3. Preparation of fragment 5 digested with XhoI and PacI in pMA for final full assembly. 4. Full assembly of CHIKV-Δ5nsP3 genome in pMA by fusion of AgeI/XhoI-digested fragments 3 and 4 and XhoI/PacI-digested fragment 5 with AgeI/PacI-linearized pMA fragments 1 and 2. Correct CHIKV-Δ5nsP3 genome assembly was verified via Sanger sequencing.

Figure 4A:
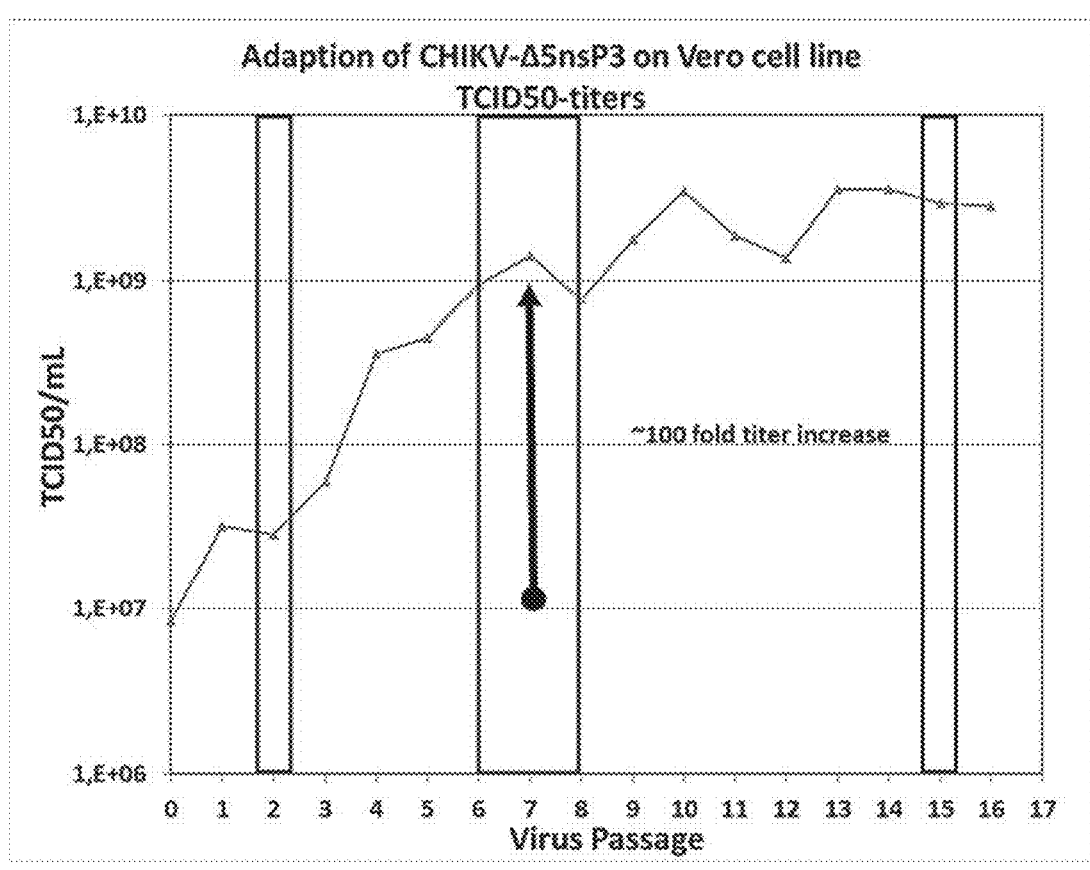
Figure 4B:
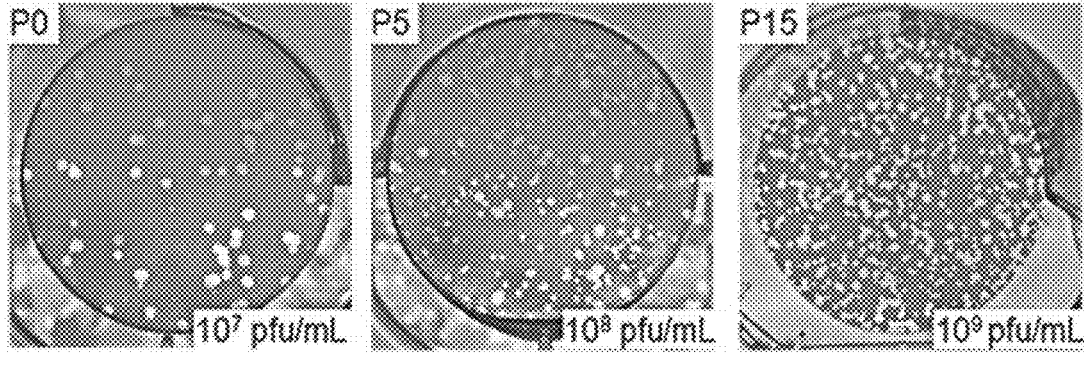
Figure 4C:
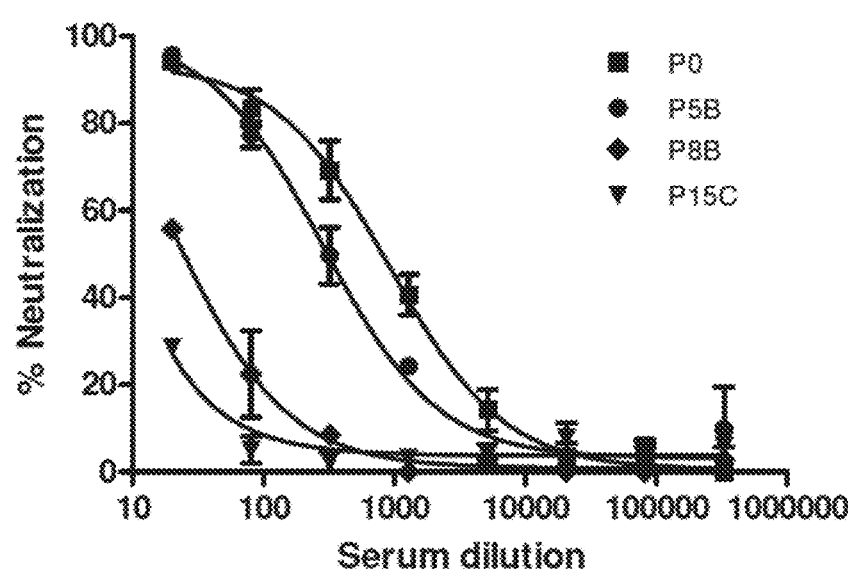

FIGS. 4A-4C Yield, plaque size and immunogenicity of CHIKV-Δ5nsP3 following passaging in Vero cells. Virus was passaged in three parallel replicates (A, B and C) starting from a common P0 (rescue) as detailed in Table 2. (FIG. 4A) Virus titers 24 h after infection of Vero cells from passage 0 to passage 16. The average titer of the three replicates (A, B and C) is shown. (FIG. 4B) Relative titers of P0, P5 and P15 CHIKV-Δ5nsP3 as assessed by plaque assay. Vero cells were seeded at a density of $4 \times 10^5$ cells per well in 6-well plates in MEM supplemented with 5% FBS, 2 mM L-Glutamine and 1% Antibiotic-Antimycotic (Anti-Anti) and were incubated overnight at 35° C. and 5% $CO_2$. On the next day, culture supernatant was removed from Vero cells and serial dilutions of CHIKV-Δ5nsP3 were added onto the cells. Following incubation for 1 hour at 35° C./5% $CO_2$, a methylcellulose overlay with a final concentration of 2% was added and cells were further incubated 3 days at 35° C./5% $CO_2$. Finally, plaques were counted after crystal violet staining (0.5% crystal violet in 5% formaldehyde) to assess virus titer (pfu/ml) and plaque morphologies. (FIG. 4C) Immunogenicity of P0, P5B, P8B and P15C CHIKV-Δ5nsP3 as assessed by neutralization of CHIKV-Δ5nsP3 (P0) in PRNT on Vero cells. Vero cells were seeded in 12-well plates at a density of $3 \times 10^5$ and incubated overnight at 35° C./5% $CO_2$. Groups of five C57Bl/6 mice were immunized once subcutaneously with a dose of $10^5$ $TCID_{50}$ of the respective CHIKV-Δ5nsP3 passages. CHIKV-Δ5nsP3 at P0 (virus rescue), also at $10^5$ $TCID_{50}$, was used as a positive control. Day 21 serum pools at 4-fold serial dilutions ranging from 1:20 to 1:327,680 were mixed with 560 pfu/ml CHIKV-Δ5nsP3 (at P0) and incubated for one hour. The CHIKV-Δ5nsP3/neutralization mixes were then added to the Vero cells and the plates were incubated for 2 hours at 35° C./5% $CO_2$. This step was followed by a 2% methylcellulose overlay and plates were incubated for ~60 hours at 35° C./5% $CO_2$. After removal of the overlay, cells were stained with crystal violet/5% formaldehyde and plaques were counted.

Figure 5A:
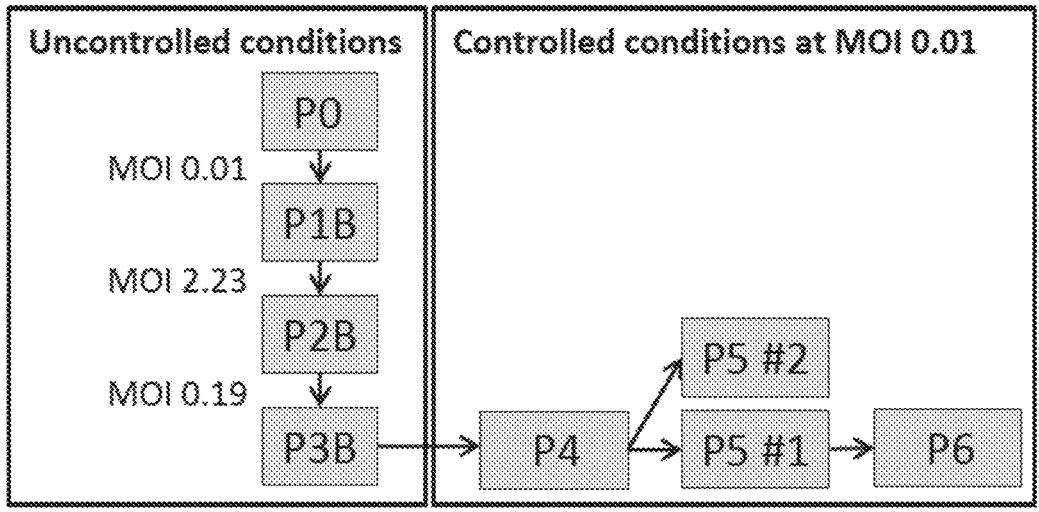
Figure 5B:
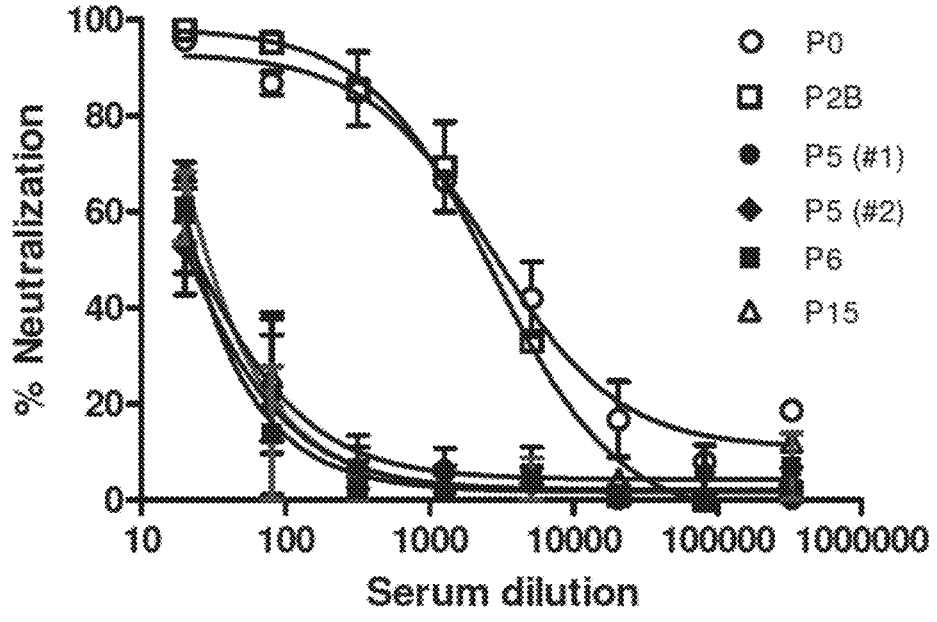

FIGS. 5A and 5B Effect of controlled MOI (0.01) during passaging of CHIKV-Δ5nsP3 on immunogenicity. (FIG. 5A) Schematic illustration of CHIKV-Δ5nsP3 passaging on Vero cells under uncontrolled and controlled conditions. CHIKV-Δ5nsP3 P0 was passaged on Vero cells to P3B under uncontrolled conditions with varying MOI (as outlined in Table 2; Replicate B). Using P3B as a starting material, a controlled infection process was carried out with all subsequent infections at the defined MOI of 0.01 to generate one P4 passage, two P5 passages and one P6 passage for analysis of immunogenicity in mice. (FIG. 5B) Immunogenicity of P0 (○), P2B (□), P5 #1 (○), P5 #2 (◆), P6 (■) and P15 (△) CHIKV-Δ5nsP3 as assessed by neutralization of CHIKV-Δ5nsP3 (P2) in PRNT on Vero cells. Groups of ten C57Bl/6 mice were subcutaneously immunized with a single dose of the respective CHIKV-Δ5nsP3 preparations at an intended dose of $10^5$ $TCID_{50}$ and at day 21 following immunization, pooled sera were assessed for CHIKV-Δ5nsP3 (560 pfu/ml) neutralization capacity at 4-fold serial dilutions ranging from 1:20 to 1:327,680 as described in FIGS. 4A-4C.

FIGS. 6A-6D Immunogenicity and observed genomic heterogeneities of single plaque isolates of CHIKV-Δ5nsP3 from P5B and P8B. Two CHIKV-Δ5nsP3 virus rescue harvests (4399gr1 P0 (#1) and 4415gr1 P0 (#2)) and a P15 CHIKV-Δ5nsP3 harvest (P15C-DS) served as immunogenic and non-immunogenic controls, respectively. (FIG. 6A) Immunogenicity of CHIKV-Δ5nsP3 single plaque isolates P5B-11, P5B-03 and P8B-05 as assessed by neutralization of CHIKV-Δ5nsP3 (P2) in PRNT on Vero cells. Groups of ten C57Bl/6 mice were subcutaneously immunized with a single dose of the respective CHIKV-Δ5nsP3 isolates at the indicated $TCID_{50}$ doses and at day 19 following immunization, pooled sera were assessed for CHIKV-Δ5nsP3 (560 pfu/ml) neutralization capacity at 4-fold serial dilutions ranging from 1:20 to 1:327,680 as described in FIGS. 4A-4C. (FIG. 6B) Schematic genomes of CHIKV-Δ5nsP3 single plaque isolates P5B-11, P5B-03 and P8B-05 derived from Sanger sequencing covering the full CHIKV-Δ5nsP3 genome with identified point mutations indicated. (FIG. 6C) Immunogenicity of further CHIKV-Δ5nsP3 single plaque isolates P5B-02, P5B-04, P5B-07 and P8B-01 was assessed as in (A). (FIG. 6D) Schematic genomes of CHIKV-Δ5nsP3 single plaque isolates P5B-02, P8B-01, P5B-04 and P5B-07 derived from Sanger sequencing covering the full CHIKV-Δ5nsP3 genome with identified point mutations indicated.

Figure 7:
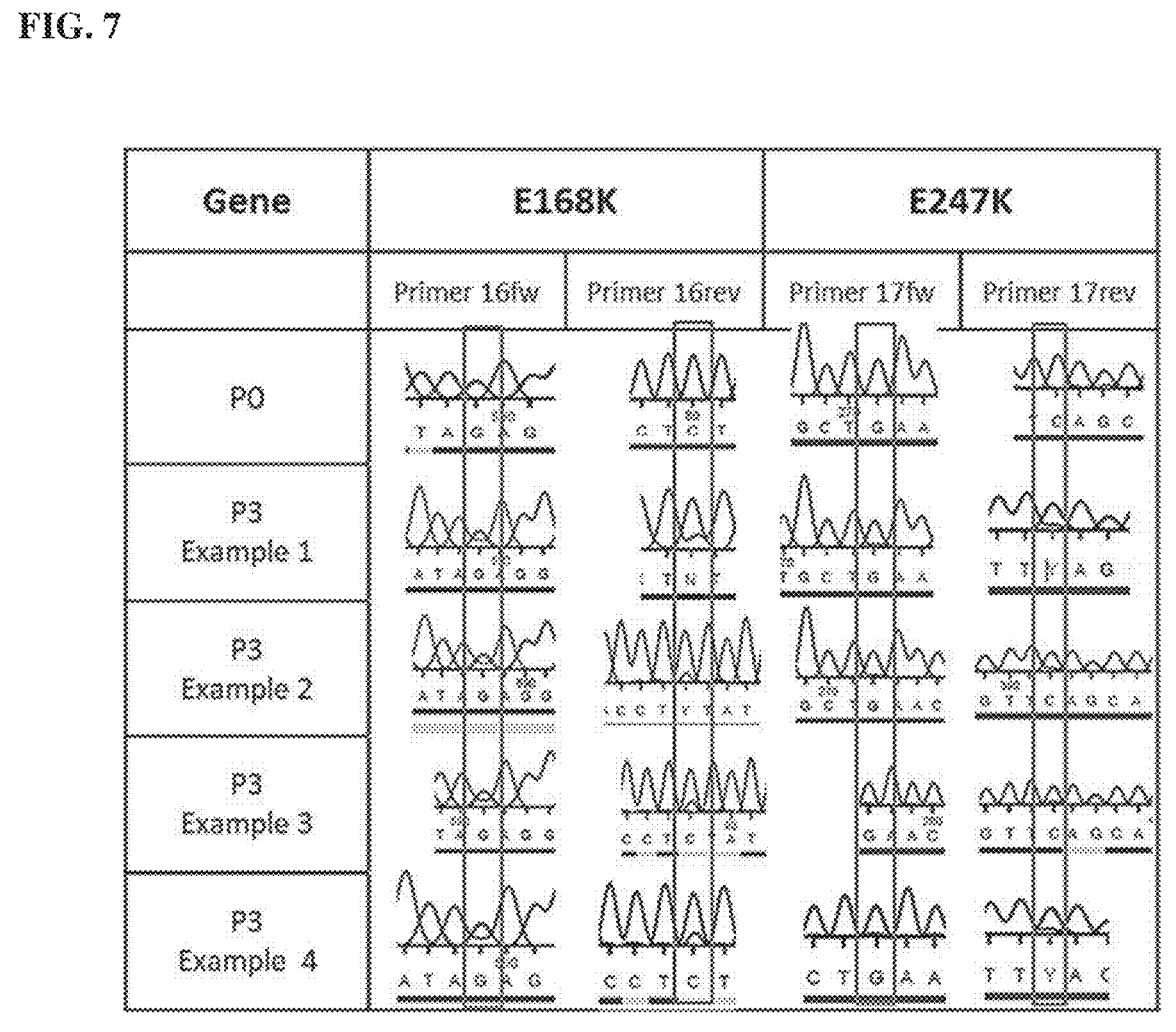

FIG. 7 Chromatograms from Sanger sequencing of CHIKV-Δ5nsP3 at passage 0 (P0) and four independently generated CHIKV-Δ5nsP3 samples at passage 3 (P3 Examples 1-4), revealing E168K and E247K heterogeneities in the E2 protein arising by passage 3. The four independently generated CHIKV-Δ5nsP3 samples at P3 (P3 Examples 1-4) were all derived from the same MVSB (P1). The regions shown cover genomic regions encoding amino acids 168 and 247 of the E2 protein and were sequenced with primer pairs 16 and 17 as indicated. (For primer sequences, see Table 1). For comparison, sequencing chromatograms of CHIKV-Δ5nsP3 at passage 0 (P0) are shown. Sites of sequence heterogeneities are indicated by boxes.

Figure 8A:
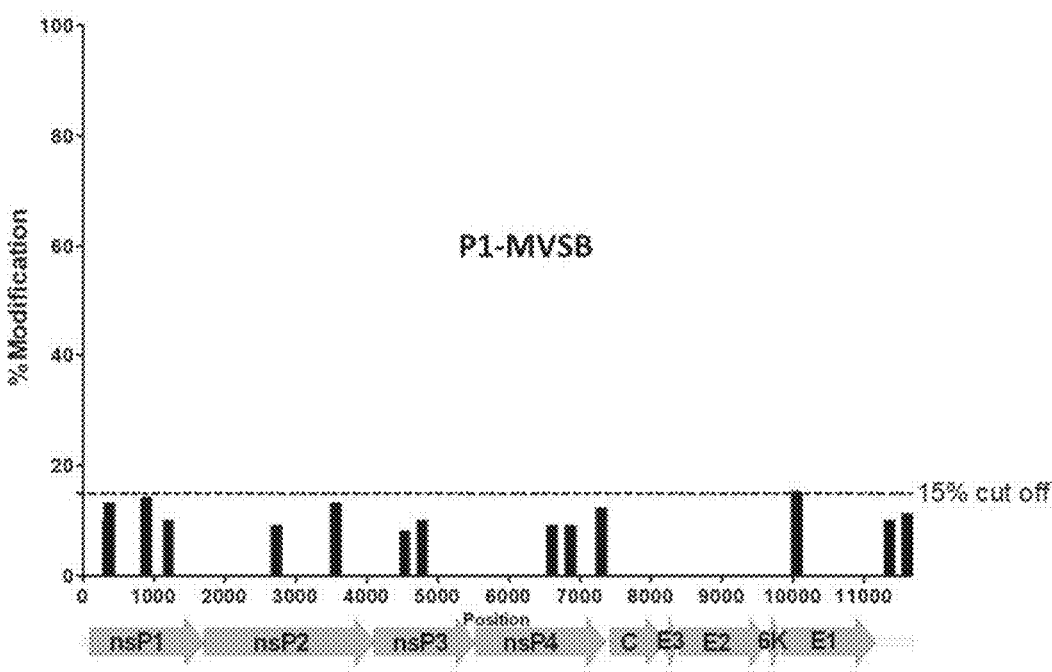
Figure 8B:
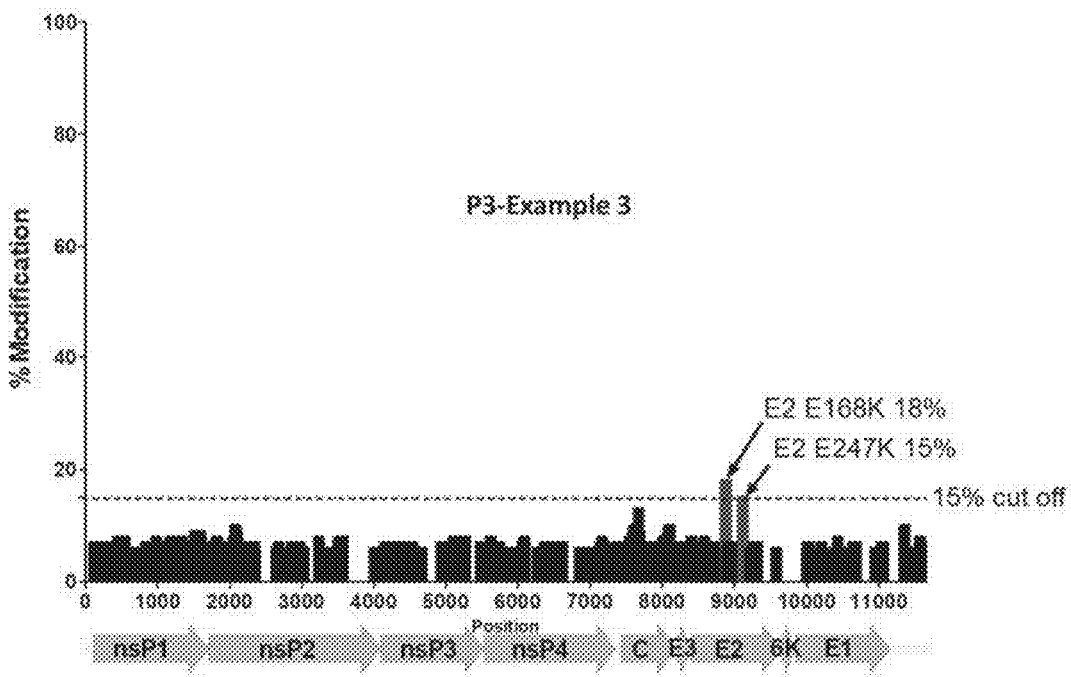
Figure 8C:
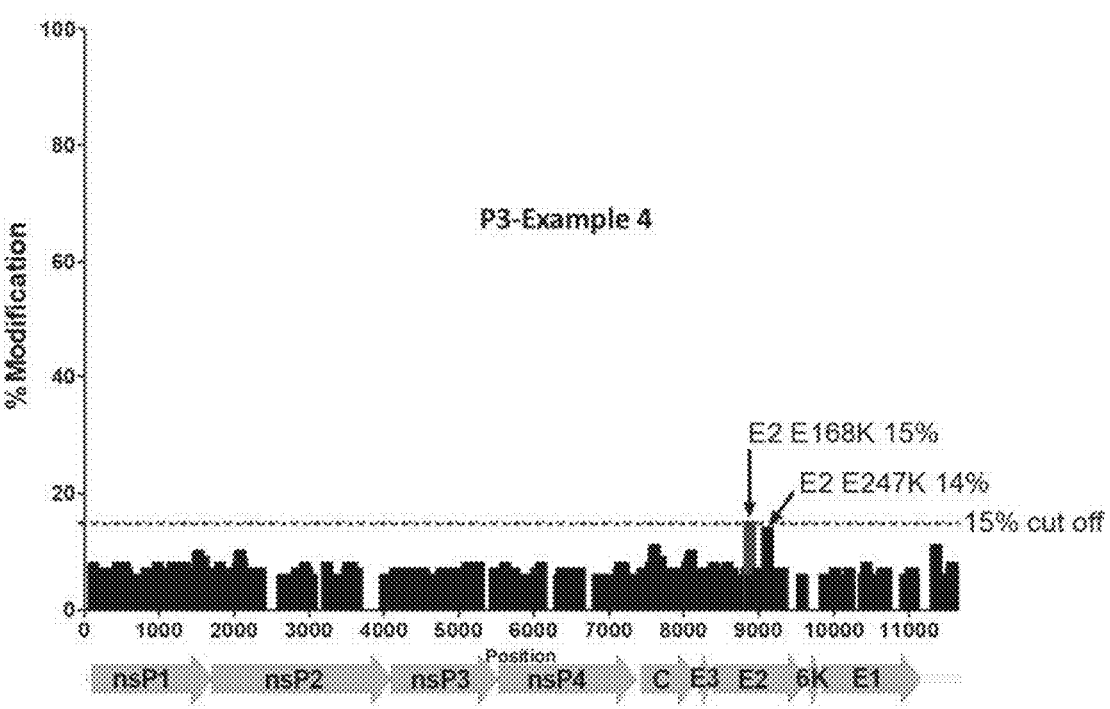

FIGS. 8A-8C Next generation sequencing (NGS) of a Master Virus Seed Bank (P1) and two independently generated passage three (P3) CHIKV-Δ5nsP3 preparations: (FIG. 8A) P1-MVSB; (FIG. 8B) P3-Example 3; (FIG. 8C) P3-Example 4. A background level of genomic heterogeneities is set at 15% as indicated by the dotted line. More frequent heterogeneities arising by passage 3 included point mutations at genomic nucleic acid positions 8882 and 9119, which correspond to E168K and E247K mutations, respectively, in the E2 protein as indicated in (FIG. 8B) and (FIG. 8C).

Figures 9A, 9B, 9C:
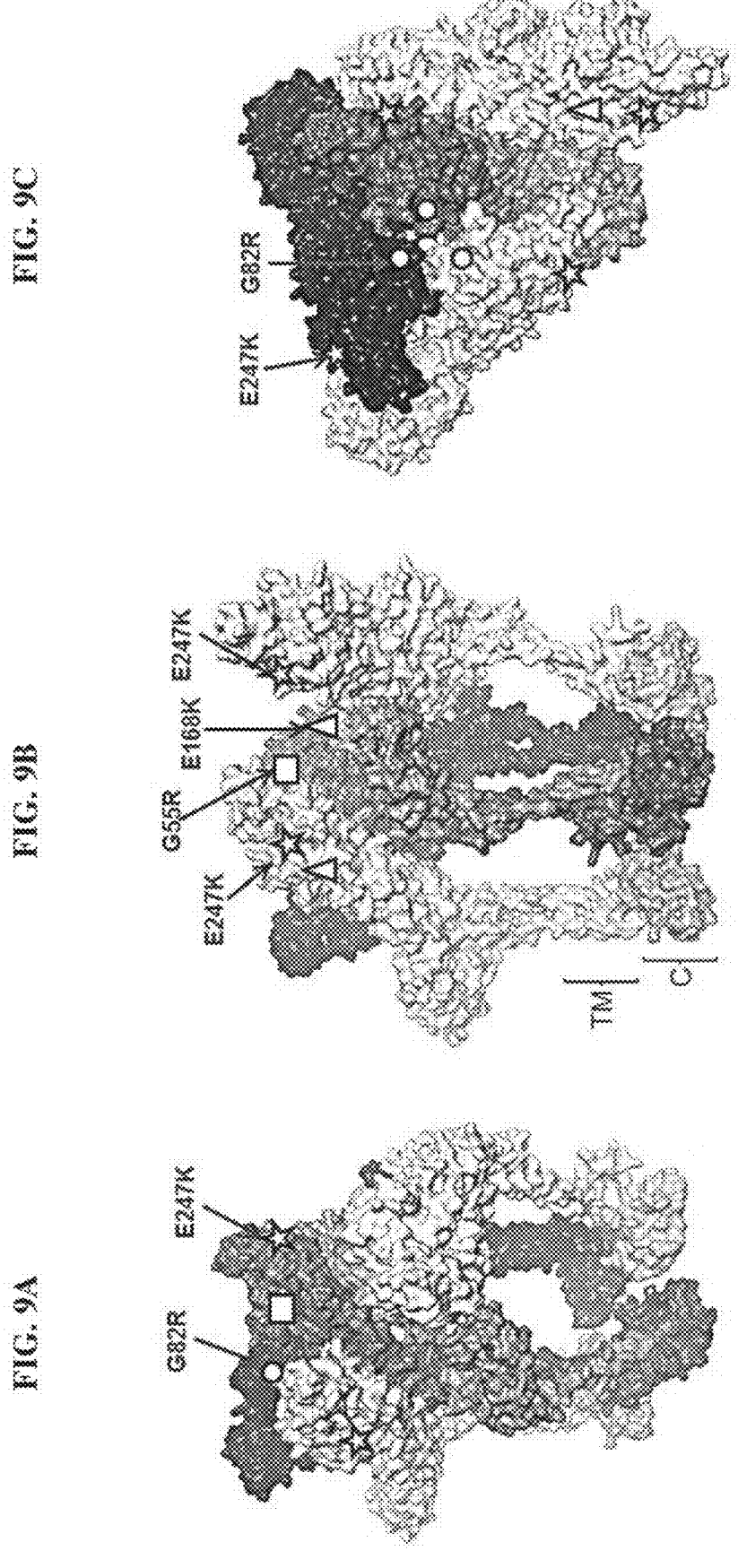

FIGS. 9A-9C Location of amino acid positions with frequently observed heterogeneities (G55R, G82R, E168K and E247K) within the E2 glycoprotein marked on equivalent positions on a cryo-EM structure of CHIKV VLPs of strain Senegal 37997 (PDB 3J2W; Sun S, et al., Structural analyses at pseudo atomic resolution of Chikungunya virus and antibodies show mechanisms of neutralization (2013) eLife 2: e00435. DOI: 10.7554/eLife.00435). G55R is indicated by a square, G82R is indicated by a circle, E168K is indicated by a triangle and E247K is indicated by a star. The figures show the CHIKV proteins of the unit-cell as they would be assembled in the viral membrane, composed of four copies of E1/E2 dimers with the transmembrane portion (TM) indicated by brackets, and the capsid protein (C) at the inner (bottom) side of the membrane. Three E1/E2/capsid-assemblies compose the trimeric q3-spike near the 5-fold axis and the fourth assembly is one of three elements of the i3-spike at the 3-fold axis, all in surface representation and viewed from three different angles: (FIG. 9A) CHIKV unit-cell side view; viewpoint above membrane plane. (FIG.

9B) CHIKV unit-cell side view; viewpoint below membrane plane (FIG. 9C) CHIKV unit-cell, top view.

FIG. 10 Groups for subcutaneous immunization of C57Bl/6 mice with virus preparations of different P3: P5B-07 (E168K) ratios to determine the threshold at which the presence of the E168K point mutation results in loss of CHIKV-Δ5nsP3 immunogenicity at a dose of approximately $3\times10^4$ $TCID_{50}$. The formulation ratios of P3 and P5B-07 (E168K mutant) for groups 1, 3 and 5 were 1:0.1, 1:1 and 1:10, respectively, with an intended dose of $3\times10^4$ $TCID_{50}$. Additionally, group 6 and group 7 represent P3 alone and P5B-07 (E168K) alone, respectively. The reference sequence (wild-type) in the heterogenic position (corresponding to nucleotide 8882) was G and depending on the ratio of either 1:0.1, 1:1 or 1:10, a shift towards the nucleotide A, i.e., G>A to G=A or G<A, was in accordance with sequencing chromatograms. The P3 viral population displayed ~20% E168K mutants. The P5B-07 (E168K) viral population did not show heterogeneity (i.e., ~100% contained the E2 protein E168K mutation).

FIGS. 11A-11D Effect on immunogenicity of different P3 to E168K-mutant CHIKV-Δ5nsP3 ratios assessed by VRP-based neutralization assay. Single mouse sera were generated by subcutaneous immunization of C57Bl/6 mice with an intended dose of $3\times10^4$ $TCID_{50}$ of CHIKV-Δ5nsP3 P3: E168K at ratios 1:0.1, 1:1 and 1:10 as outlined in FIG. 10. Day 21 single sera were analyzed for neutralization of LR-CHIKV virus replicon particles (VRPs) using a BHK-21 cell-based Luciferase assay. VRPs resemble a replication-deficient wild-type CHIKV displaying capsid and envelope proteins of the LR2006-OPY1 wild-type virus. Briefly, $2\times10^4$ BHK-21 cells were seeded in 96-well plates and incubated overnight at 35° C./5% $CO_2$. CHIKV-Δ5nsP3 VRPs were incubated with serial dilutions (starting at 1:20 to 1:312,500) of mouse sera for 1 hour at 35° C. CHIKV VRP/serum mixes were added to BHK-21 cells at an MOI of 5 and incubated for 1 hour at 35° C./5% $CO_2$. Cells were washed and fresh medium was added. Luciferase activity was measured in the supernatant 24 hours post-infection using the Renilla Luciferase Assay System (Promega). P-MVSB positive control (○), P5B-07 (E168K) negative control (□) and individual mouse sera immunized with respective P3: E168K ratio (filled circles). (FIG. 11A) Immunogenicity of CHIKV-Δ5nsP3 P3: E168K at a ratio of 1:0.1 (Group 1). (FIG. 11B) Immunogenicity of CHIKV-Δ5nsP3 P3: E168K at a ratio of 1:1 (Group 3). (FIG. 11C) Immunogenicity of CHIKV-Δ5nsP3 P3: E168K at a ratio of 1:10 (Group 5). (FIG. 11D) Summary of immunogenicity results shown in FIG. 11A, FIG. 11B, and FIG. 11C: strong immunogenic (++positive), low immunogenic (+low positive) and negative (−) in comparison to P3.

Figure 12:
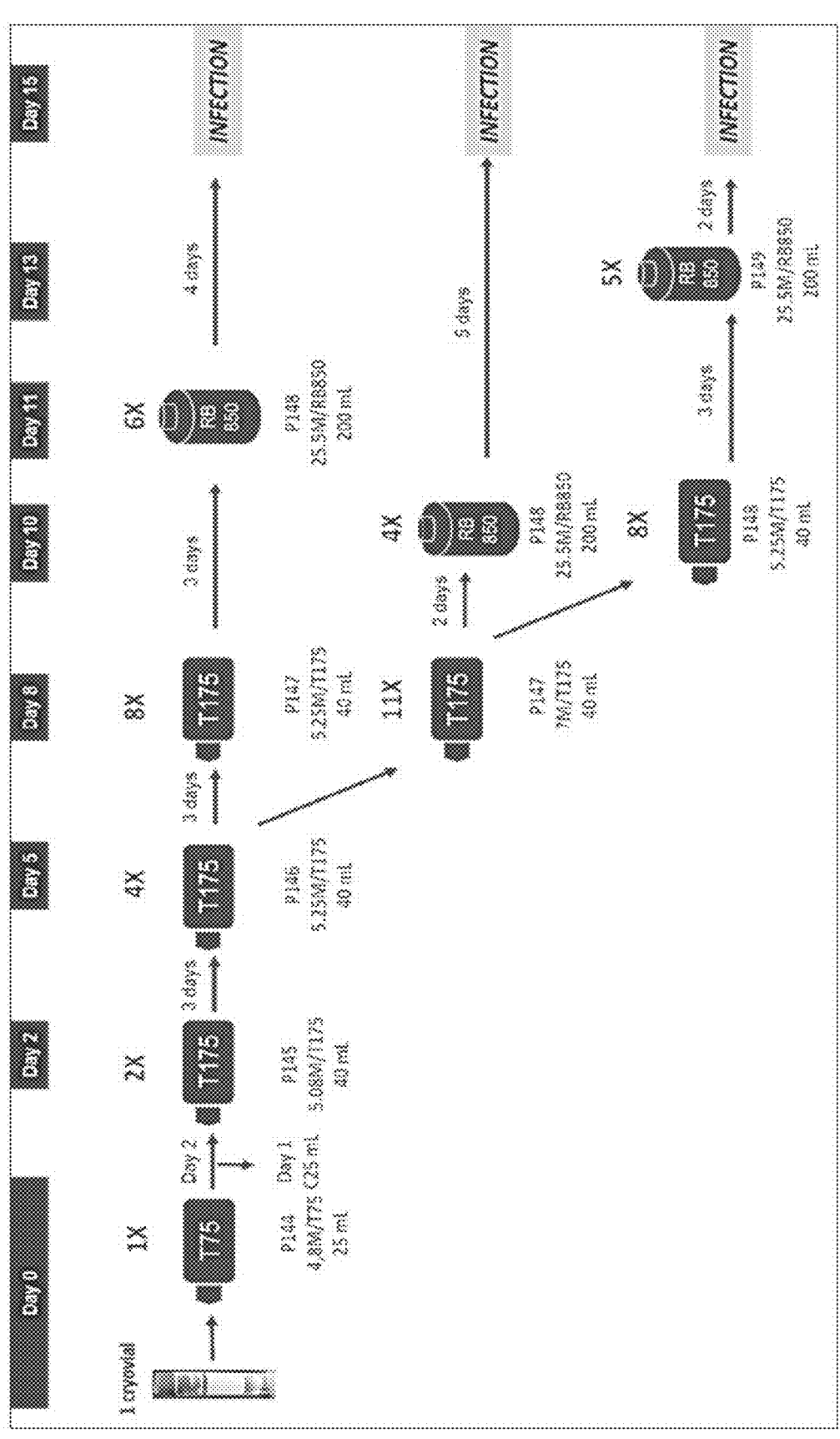

FIG. 12 Vero cell culture train from thawing to infection with CHIKV-Δ5nsP3 in 850 cm² roller bottles. P: Passage, M: Million, T75: T-Flask 75 cm², T175: T-Flask 175 cm², RB850: Roller Bottle CellBIND® 850 cm².

Figure 13A:
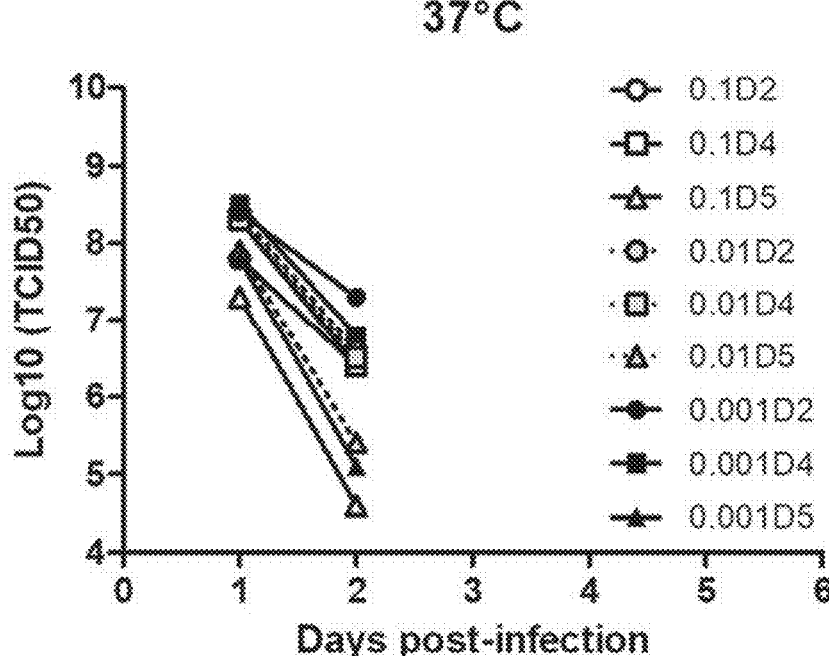
Figure 13B:
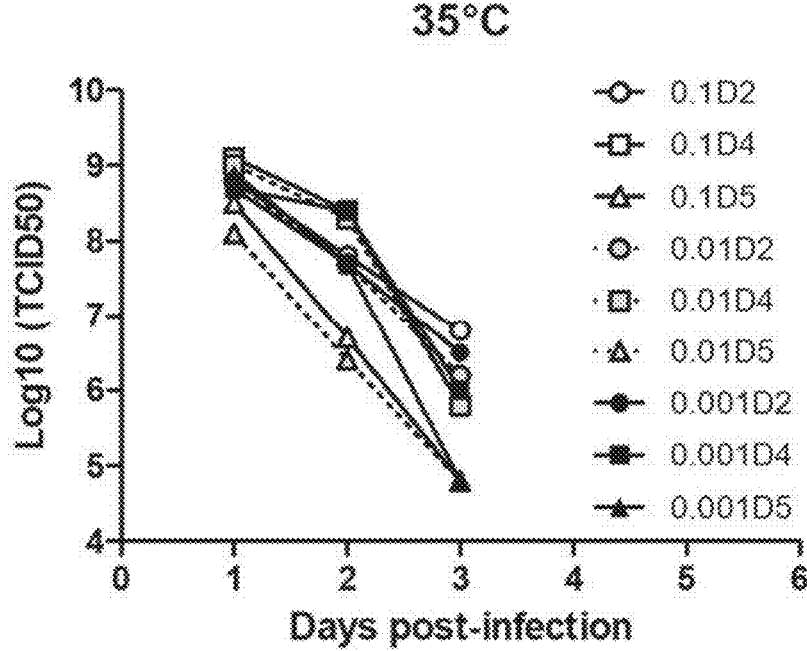
Figure 13C:
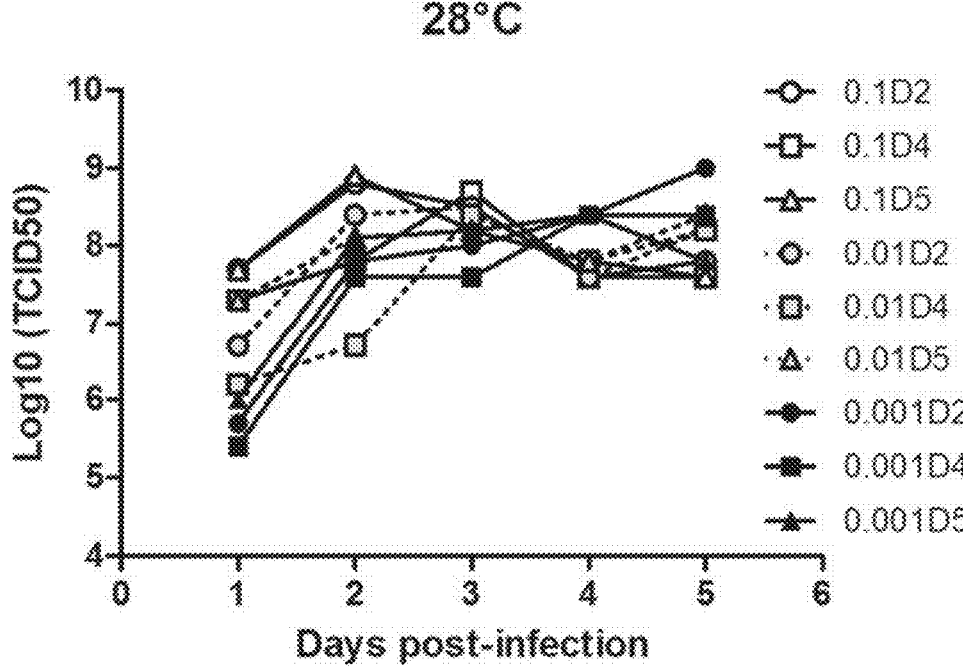

FIGS. 13A-13C Effect on virus titer of cell growth temperature, multiplicity of infection and post-seeding infection time during production of CHIKV-Δ5nsP3 in Vero cells. Vero cells were expanded at 35° C. in MEM, 2 mM glutamine and 10% FBS and seeded in 850 cm² roller bottles for cell infection. For virus production, different temperatures (37° C., 35° C., 28° C.), MOIs (0.1; 0.01; 0.001 $TCID_{50}$/cell) and times of cell infection post Vero cell seeding in days (D2, D4, D5) were tested in culture medium deprived of FBS. Shown are viral productivities measured on Vero cells according to the Reed & Muench method and expressed in $TCID_{50}$/mL. (FIG. 13A) 37° C.; (FIG. 13B) 35° C.; (FIG. 13C) 28° C.

Figure 14:
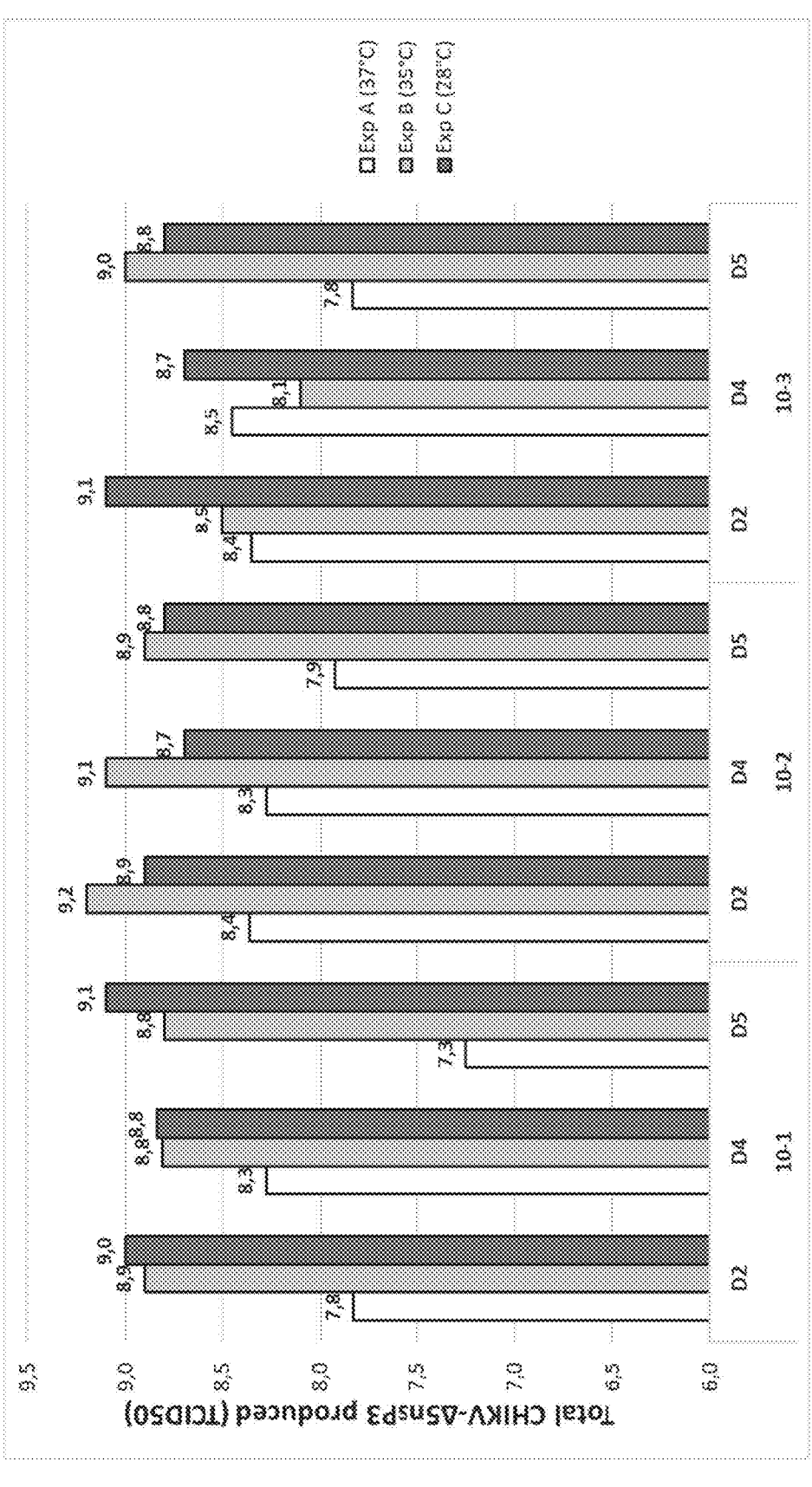

FIG. 14 Total CHIKV-Δ5nsP3 virus productivity from each of the conditions described in FIGS. 13A-13C.

FIGS. 15A and 15B Maximum CHIKV-Δ5nsP3 virus titers: Response surface quadratic model. (FIG. 15A) ANOVA analysis of the model. Grey line: significant model term (Prob(F)<0.05; values greater than 0.1 indicate the model term is not significant). (FIG. 15B) Contour Plot of the model.

FIGS. 16A and 16B CHIKV-Δ5nsP3 virus stability: Response surface quadratic model. (FIG. 16A) ANOVA analysis of the model. Grey line: significant model term (Prob(F)<0.05; values greater than 0.1 indicate the model term is not significant). (FIG. 16B) Contour Plot of the model.

Figure 17A:
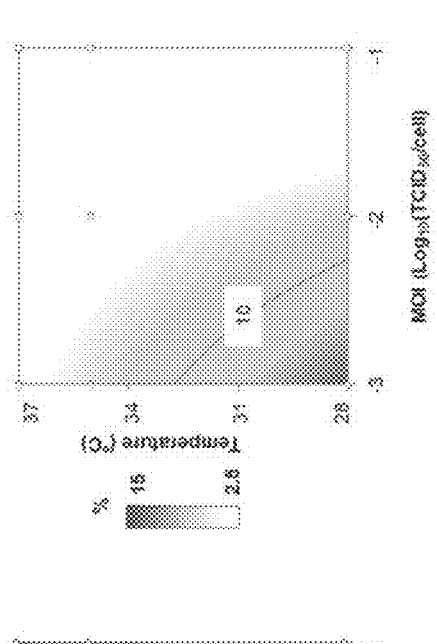
Figure 17A:
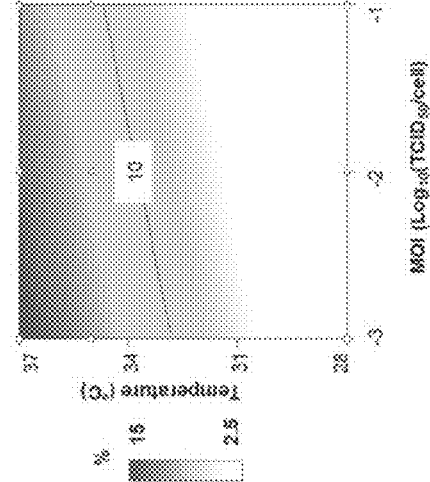
Figure 17B:
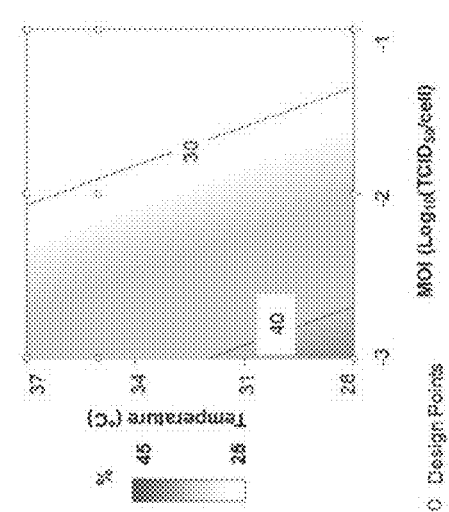

FIGS. 17A and 17B Heterogeneity of the CHIKV-Δ5nsP3 E2 viral protein at genomic nucleic acid positions 8882, 9112 and 9649, corresponding to E2 amino acids 168, 247 and 423, respectively: Model analysis from Day 2 CHIKV-Δ5nsP3 sample harvests. (FIG. 17A) ANOVA analysis of the model. Grey line: significant model term (Prob(F)<0.05). (FIG. 17B) Contour Plot of the model.

Figures 18A, 18B:
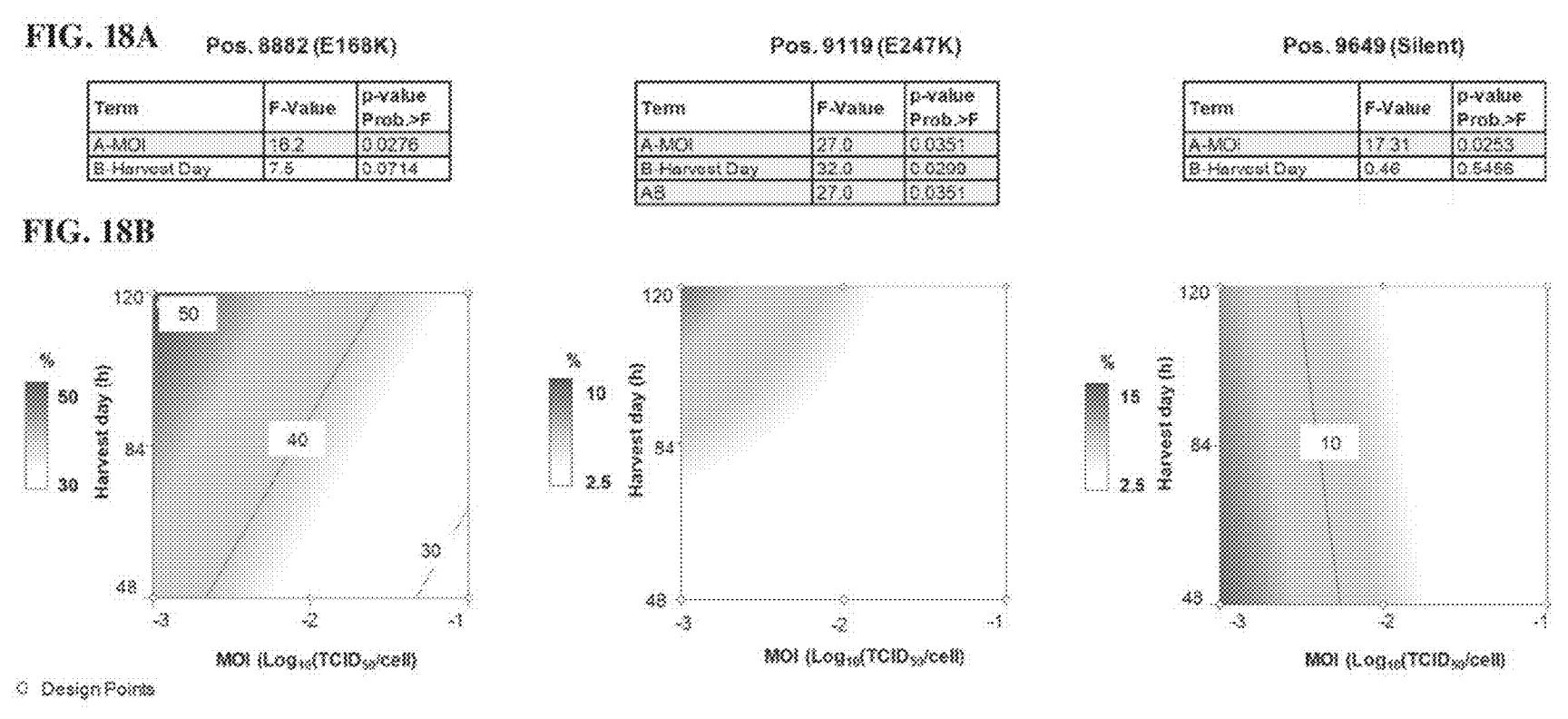

FIGS. 18A and 18B Heterogeneity of the CHIKV-Δ5nsP3 E2 viral protein at genomic nucleic acid positions 8882, 9112 and 9649; corresponding to E2 amino acids 168, 247 and 423, respectively: Model analysis from Day 2 and Day 5 CHIKV-Δ5nsP3 sample harvests (28° C.). (FIG. 18A) ANOVA analysis of the model. Grey line: significant model term (Prob(F)<0.05). (FIG. 18B) Contour Plot of the model.

DETAILED DESCRIPTION OF THE INVENTION

During the course of industrialization of the CHIKV-Δ5nsP3 attenuated virus vaccine candidate, it was observed that passaging of the virus on Vero cells resulted in higher virus titers with increasing passages; however, a concomitant increase in sequence heterogeneity of the CHIKV-Δ5nsP3 viral genome was also observed. Certain point mutations arising during passaging on Vero cells were found to be reproducible from batch to batch and appeared already in early passages on the new cell substrate. It was surprisingly observed that some of these mutations correlated with a significant loss of or decrease in neutralizing immunogenicity conferred by the CHIKV-Δ5nsP3 virus. Other reproducible mutations did not reduce immunogenicity and/or acted as "rescuing" mutations for the immunogenicity-reducing mutations. A correlation between a low multiplicity of infection ("MOI") and generation of increased sequence heterogeneity in CHIKV-Δ5nsP3 was identified; however, because of the need to have a single source of virus over years of manufacturing, high MOIs are generally not feasible for industrial use. It was therefore not clear at the outset whether culturing conditions allowing the generation of immunogenic CHIKV-Δ5nsP3 particles with a production yield sufficient for reproducible and reliable manufacturing could be found (problem of the invention).

Provided herein are methods to control and minimize the herein observed immunogenicity-reducing mutations while still enabling high production yields. Also provided herein are pharmaceutical compositions comprising an effective amount of an immunogenic Chikungunya virus with a residual amount of a non-immunogenic variant of Chikungunya virus. In a preferred embodiment, the pharmaceutical composition is produced using a low MOI such as an MOI of less than 0.1, e.g. 0.01 or 0.001, but produced under such controlled conditions (e.g., reduced passage numbers following rescue, optimized temperature and host cell confluency) to minimize amounts of non-immunogenic variant(s) of Chikungunya virus as described herein. In some embodiments, the virus particle is a live virus, a chimeric virus, an attenuated live virus, a modified live virus, or a recombinant live virus. In one embodiment, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus, such as a substitution or deletion. In some embodiments, the virus is a recombinant live virus, meaning a virus that is generated recombinantly and may contain nucleic acid sequences from different sources. In some aspects, the wild-type Chikungunya virus is inactivated. In a preferred embodiment, the virus is inactivated with formaldehyde.

In one embodiment, the immunogenic Chikungunya virus is a live attenuated virus. In a preferred embodiment, the live attenuated Chikungunya virus is the protective CHIKV-Δ5nsP3 as described by Hallengärd D, et al. (supra), referred to herein as CHIKV-Δ5nsP3 and defined by the nucleic acid sequence of SEQ ID NO: 1. Briefly, the wild-type CHIKV genome carries a positive-sense single-stranded RNA genome of 11 kb containing two open reading frames encoding nonstructural proteins (nsP1 to nsP4) and structural proteins (C, E3, E2, 6K, and E1), respectively. An attenuated CHIK virus, CHIKV-Δ5nsP3, based on the La Reunion CHIKV strain LR2006-OPY1, was constructed by substituting amino acid residues 1656 to 1717 of the P1234 polyprotein with a small linker (AA sequence AYRAAAG) in the hypervariable region of the nsP3 protein (see FIG. 2). CHIKV-Δ5nsP3 has been shown to be infectious, highly immunogenic and protective against challenge with wild-type CHIKV (Hallengärd D, et al., supra and Hallengärd D, et al., Prime-Boost Immunization Strategies against Chikungunya Virus (2014) J. Virology, 88(22):13333-13343, and Roques P, et al. 2017, supra). In one embodiment, the live attenuated Chikungunya virus may be a variant of the CHIKV-Δ5nsP3 attenuated mutant virus. In a preferred embodiment, the live attenuated Chikungunya virus as provided herein comprises the CHIKV-Δ5nsP3 as encoded by the nucleic acid sequence defined by SEQ ID NO: 1. As used herein, the term "CHIKV-Δ5nsP3" is used interchangeably with "CHIKV-Δ5nsP3 virus", "CHIKV-Δ5nsP3 particle", "CHIKV-Δ5nsP3 virus particle" or plural versions thereof.

Provided herein is a pharmaceutical composition comprising an effective amount of a CHIKV-Δ5nsP3. In one aspect, an effective amount of an immunogenic CHIKV-Δ5nsP3 virus is defined as an amount sufficient to elicit neutralizing antibodies to Chikungunya virus. In a further aspect, an effective amount of an immunogenic CHIKV-Δ5nsP3 virus is defined as an amount to elicit an immune response in a vaccinated subject which confers protective immunity against Chikungunya virus infection. In a preferred aspect, an effective amount of CHIKV-Δ5nsP3 is defined as at least $10^2$, at least $10^3$, at least $10^4$, at least $10^5$, at least $10^6$, preferably at least $10^3$ immunogenic CHIKV-Δ5nsP3 particles. In one aspect, immunogenic CHIKV-Δ5nsP3 particles are defined as CHIKV-Δ5nsP3 particles which express an E2 structural protein as defined by the polypeptide sequence of SEQ ID NO: 2. In one aspect, the E2 structural protein contains one or more point mutations that do not affect the immunogenicity of the virus, i.e., are not immunogenicity reducing. In one embodiment, the point mutations that do not affect the immunogenicity of the virus may be at amino acids 232 and/or 247 of the E2 protein, such as H232Y and/or E247K. In one embodiment, the E2 structural protein of the CHIKV-Δ5nsP3 contains no more than about ten point mutations. In one embodiment, the E2 structural protein of the CHIKV-Δ5nsP3 contains no more than 9, 8, 7, 6, 5 or 4 point mutations. In a preferred embodiment, the E2 structural protein of the CHIKV-Δ5nsP3 contains three or less point mutations, most preferably only one or two point mutations.

As defined herein, an immunogenic CHIKV-Δ5nsP3 is a CHIKV-Δ5nsP3 which is capable of stimulating an effective immune response in vivo when delivered e.g. at a dose of about $3\times10^4$ $TCID_{50}$, i.e., an immune response in which neutralizing antibodies are produced which are sufficient for reducing or preventing signs or symptoms of Chikungunya virus disease. In a preferred embodiment, the immunogenic CHIKV-Δ5nsP3 as defined herein is a CHIKV-Δ5nsP3 which expresses an E2 structural protein according to the amino acid sequence provided by SEQ ID NO: 2. In a further preferred embodiment, the immunogenic CHIKV-Δ5nsP3 as defined herein is defined by the polynucleotide sequence according to SEQ ID NO: 1. As an alternative or additional definition, the immunogenic CHIKV-Δ5nsP3 of the current invention stimulates the production of antibodies with neutralizing capacity in an immunized subject, i.e., neutralization of Chikungunya virus in an in vitro assay of at least 50%, preferably at least 60%, preferably at least 70%, more preferably at least 80%, even more preferably at least 90%, most preferably at least 95% at a 1:80 or higher serum dilution.

As defined herein, a non-immunogenic CHIKV-Δ5nsP3 is a CHIKV-Δ5nsP3 which elicits levels of neutralizing antibodies in a vaccinated subject inadequate to prevent signs or symptoms of Chikungunya virus disease. In a preferred embodiment, a non-immunogenic CHIKV-Δ5nsP3 is a CHIKV-Δ5nsP3 which expresses an E2 structural protein with at least one amino acid substitution, especially amino acid substitutions in the E2 structural protein, especially E168K and/or G55R substitutions, particularly an E168K substitution. A non-immunogenic CHIKV-Δ5nsP3 is further defined as eliciting antibodies in an immunized subject which show poor capacity to neutralize infection of cells with Chikungunya virus (wild-type or attenuated) in an in vitro assay. In particular, a non-immunogenic CHIKV-Δ5nsP3 is defined as eliciting levels of neutralizing antibodies in an immunized subject which provide less than 60%, less than 50%, less than 40%, less than 30%, less than 20%, especially less than 10%, neutralization of Chikungunya virus in an in vitro neutralization assay at a 1:80 or higher serum dilution.

In a further aspect, the effective amount of CHIKV-Δ5nsP3 is defined as an amount sufficient to elicit neutralizing antibodies against wild-type Chikungunya virus. In one aspect, the pharmaceutical composition is a two-shot pharmaceutical composition. In a preferred aspect, the pharmaceutical composition is a one-shot pharmaceutical composition. In a preferred aspect, the pharmaceutical composition comprises at least $10^2$, at least $10^3$, at least $10^4$, at least $10^5$, at least $10^6$, preferably between about $10^3$ to $10^5$ total CHIKV-Δ5nsP3 viral particles, especially about $10^3$ or $10^4$ CHIKV-Δ5nsP3 comprised in a total pool of particles with and without point mutations, especially immunogenicity-reducing point mutations. In a preferred aspect, the pharmaceutical composition comprises a detectable amount of non-immunogenic CHIKV-Δ5nsP3 as defined herein; preferably a non-immunogenic CHIKV-Δ5nsP3 with at least one point mutation compared with the wild-type E2 protein as defined by SEQ ID NO: 2.

In a preferred embodiment, the pharmaceutical composition comprises CHIKV-Δ5nsP3 and comprises an increased amount of a non-immunogenic variant(s) of CHIKV-Δ5nsP3, e.g. compared to a vaccine composition comprising CHIKV-Δ5nsP3 produced in BHK-21 cells as used in mouse studies described in Hallengärd D, et al. 2014, supra, but still comprises sufficient immunogenic particles of CHIKV-Δ5nsP3 to produce protective immunity in a vaccinated subject. For instance, the pharmaceutical composition may comprise (i) CHIKV-Δ5nsP3 which expresses an E2 structural protein as defined by the polypeptide sequence of SEQ ID NO: 2 in an amount sufficient to produce protective immunity in a vaccinated subject; (ii) an increased amount of CHIKV-Δ5nsP3 having at least one mutation in said E2 structural protein, e.g. compared to a vaccine composition comprising CHIKV-Δ5nsP3 produced in BHK-21 as used in mouse studies described in Hallengärd D, et al. 2014, supra; and (iii) optionally a pharmaceutically acceptable excipient.

It is demonstrated herein that production of CHIKV-Δ5nsP3 by serial passaging five or more times in Vero cells results in high levels of sequence heterogeneity, particularly in the E2 structural protein (see e.g. Example 2 below). For instance, E168K and/or G55R mutations of the E2 protein often appeared by passage 5 (see e.g. Table 3 below), and both correlated with a drop in immunogenicity. Accordingly, production of CHIKV-Δ5nsP3 using five or more passages in Vero cells as described in Hallengärd D, et al. 2014 supra can unfavorably result in high levels of non-immunogenic mutants of CHIKV-Δ5nsP3 (such as E168K[E2]) in the vaccine composition. In contrast, it is demonstrated below that sequence heterogeneity in the E2 structural protein after fewer than five passages was much lower (see e.g. Example 3—although the E168K mutation was present after three passages, its frequency was only 18%).

Accordingly, in one aspect the pharmaceutical composition comprises (i) CHIKV-Δ5nsP3; and (ii) optionally a pharmaceutically acceptable excipient; wherein at least 30% of the CHIKV-Δ5nsP3 particles present in the composition express an E2 structural protein as defined by the polypeptide sequence of SEQ ID NO: 2. In this embodiment, at least 30% of the CHIKV-Δ5nsP3 particles are non-mutants with respect to the E2 structural protein, i.e. express the E2 structural protein of SEQ ID NO: 2. In other words, the frequency of sequence heterogeneity (i.e. mutant CHIKV-Δ5nsP3 particles expressing at least one mutation in the E2 structural protein of SEQ ID NO: 2) is 70% or less. Unless specified otherwise, when referring to "CHIKV-Δ5nsP3" or "CHIKV-Δ5nsP3 particles" in general it is intended to encompass both non-mutant and mutant forms of CHIKV-Δ5nsP3, i.e. CHIKV-Δ5nsP3 which express an E2 structural protein of SEQ ID NO: 2 and CHIKV-Δ5nsP3 which express an E2 structural protein having one or more mutations in SEQ ID NO: 2. In one embodiment, the E2 structural protein of the CHIKV-Δ5nsP3 contains no more than about ten point mutations. In one embodiment, the E2 structural protein of the CHIKV-Δ5nsP3 contains no more than 9, 8, 7, 6, 5 or 4 point mutations. In a preferred embodiment, the E2 structural protein of the CHIKV-Δ5nsP3 contains three or less point mutations, most preferably only one or two point mutations.

In preferred embodiments, at least 35%, 40%, 45%, 50%, 55%, 60%, 65%, 70%, 75%, 80%, 85%, 90%, 95%, 96%, 97%, 98% or 99% of the CHIKV-Δ5nsP3 particles present in the composition are non-mutants, i.e. express an E2 structural protein as defined by the polypeptide sequence of SEQ ID NO: 2.

In one aspect, the pharmaceutical composition comprises (i) CHIKV-Δ5nsP3; and (ii) optionally a pharmaceutically acceptable excipient; wherein less than 70% of the CHIKV-Δ5nsP3 particles present in the composition express an E2 structural protein having one or more mutations with respect to the polypeptide sequence of SEQ ID NO: 2.

In one aspect, the pharmaceutical composition comprises (i) CHIKV-Δ5nsP3; and (ii) optionally a pharmaceutically acceptable excipient; wherein less than 70% of the CHIKV-Δ5nsP3 particles present in the composition express an E2 structural protein having the mutation E168K in the polypeptide sequence of SEQ ID NO: 2.

In a preferred embodiment, the mutations (e.g. the mutation E168K) in the E2 structural protein are present at a frequency of 70% or less, e.g., less than 70% of the total CHIKV-Δ5nsP3 particles comprise one or more mutations (or the mutation E168K) and 30% or more of the total CHIKV-Δ5nsP3 particles express a non-mutated E2 structural protein or an E2 structural protein that does not comprise the mutation E168K.

In a preferred embodiment, less than 65%, 60%, 55%, 50%, 45%, 40%, 35%, 30%, 25%, 20%, 15%, 10%, 5%, 4%, 3%, 2% or 1% of the CHIKV-Δ5nsP3 particles present in the composition express an E2 structural protein having one or more mutations (such as, e.g., E168K) with respect to the polypeptide sequence of SEQ ID NO: 2. For instance, the composition may comprise 1-70%, 1-50%, 1-30%, 1-20%, 5-70%, 5-50%, 5-30%, 5-20%, 10-70%, 10-50%, 10-30% or 10-20% of mutant particles (i.e. CHIKV-Δ5nsP3 particles expressing an E2 structural protein having one or mutations (such as, e.g., E168K) with respect to the polypeptide sequence of SEQ ID NO: 2), compared to the total number of CHIKV-Δ5nsP3 particles (mutant and non-mutant) present in the composition. In one embodiment, the CHIKV-Δ5nsP3 particles expressing an E2 structural protein having an E168K mutation further comprise a mutation which mitigates the loss of immunogenicity conferred by the E168K mutation. In one embodiment, the mutation is in the nsP1 protein, especially at residue A38. In a preferred embodiment, the CHIKV-Δ5nsP3 particles expressing an E2 structural protein with an E168K mutation also express an nsP1 with an A38S mutation.

Also provided herein is a process for producing a pharmaceutical composition of the invention, comprising the steps of 1) growing a CHIKV-Δ5nsP3 virus on a cell line, and 2) minimizing the presence of immunogenicity-reducing mutations of the CHIKV-Δ5nsP3 virus. In one embodiment, the immunogenic CHIKV-Δ5nsP3 virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

In one embodiment, the presence of immunogenicity-reducing mutations is minimized by passaging CHIKV-Δ5nsP3 less than 5 times, preferably less than 4 times, preferably less than 3 times, preferably less than 2 times, more preferably only one time, most preferably at most 3 times. As used herein, the passage numbers refer to the number of in vitro passages following virus rescue (P0). In a preferred embodiment, the virus is passaged on Vero cells. In one aspect, the virus is grown at an optimal temperature. In a preferred embodiment, said optimal temperature is between about 28° C. and 37° C., preferably about 35° C.

In one embodiment, the host cell culture is infected with CHIKV-Δ5nsP3 at an optimal MOI. In one aspect, an optimal MOI is defined as an MOI low enough as to not require excessive amounts of working virus seed bank culture, but high enough to minimize immunogenicity-reducing mutations as described herein. In a preferred aspect, the optimized MOI is an MOI of less than 0.1, preferably an MOI of between about 0.1 and 0.001, more preferably an MOI of between about 0.09 to 0.0011, even more preferably an MOI of about 0.05 to 0.005, most preferably an MOI of about 0.01. In one aspect, the host cell confluency is assessed before infection. In one aspect, the host cell confluency is between about 20 and 90%, preferably between about 30 and 75%, more preferably between about 40 and 60%, especially about 50 to 60%. In one aspect, the cell culture is infected at an optimal timepoint post-host cell seeding; i.e., at between day 2 and day 5 after host cell seeding, preferably at about 4 days after host cell seeding. In one aspect, the virus particles are harvested between day one and day 6 after host cell infection, preferably between day one and day 4, preferably on day one or day 2 after host cell infection, preferably on both day one and day 2 after host cell infection.

In one aspect, immunogenicity-reducing mutations are point mutations at any location in the genome of CHIKV-Δ5nsP3 as defined by the polynucleotide sequence of SEQ ID NO: 1. In one embodiment, the immunogenicity-reducing mutations are present in the genome at a location other than the E2 protein. In a preferred embodiment, the immunogenicity-reducing mutations are located in the E2 protein, preferably at amino acid residues 55 and/or 168, e.g., G55R and/or E168K mutations, especially E168K. In some embodiments, the immunogenicity-reducing mutations as described herein are mitigated or "rescued" by other mutations in the genome. In one embodiment, a mitigating mutation of E168K is an A38S mutation of nonstructural protein 1 (nsP1).

In one aspect, the frequency of the E168K mutation of the E2 protein of the CHIKV-Δ5nsP3 is less than 90%, less than 80%, less than 70%, less than 60%, less than 50%, less than 40%, less than 30%, less than 20%, less than 10%, preferably less than 50% in the total pool of harvested CHIKV-Δ5nsP3.

In one aspect, the current invention provides an immunogenic CHIKV-Δ5nsP3 obtainable by the process provided herein. In another aspect, the current invention provides a pharmaceutical composition comprising an immunogenic CHIKV-Δ5nsP3 obtainable by the process provided herein.

Aspects of the invention provide a use of the process described herein for manufacturing a composition for immunization against a Chikungunya virus infection. In a preferred embodiment, the composition is a vaccine. In one embodiment, the vaccine is administered to the subject once, twice or three or more times. In one aspect, CHIKV-Δ5nsP3 viral particles isolated from immunized subjects have a similar point mutation profile to the vaccine composition administered, particularly with regard to point mutations in the E2 structural protein. In one embodiment, the vaccine is administered once or twice. In a preferred embodiment, the vaccine is administered only once; e.g., a one-shot vaccine. In one aspect, a booster vaccination is optionally administered. In certain preferred aspects, the pharmaceutical composition is provided in lyophilized form.

Other aspects provide compositions comprising the virus particles obtainable by the process described herein for treating and/or preventing a Chikungunya virus infection. In one aspect, the compositions are for use in a method of stimulating an immune response in a subject and/or in a method of treating or preventing a Chikungunya virus infection. As used herein, the term "preventing" also means "protecting from". The Chikungunya virus infection in one aspect may be caused by West African, East/Central/South African (ECSA) and/or Asian genotypes of Chikungunya virus.

Virus preparations produced using any of the processes described herein may be further subjected to additional processing steps, including additional filtration steps and/or lyophilization. The virus preparation may be subjected to analysis for purity of the preparation. For example, the virus preparations may be assessed for the presence of impurities and contaminants, such as, e.g., host cell genomic DNA, and/or host cell proteins. The purity of a virus preparation may be assessed using any method known in the art, such as size exclusion chromatography (SEC), optical density at different wavelengths, protein gel electrophoresis (e.g., SDS-PAGE), Western Blotting, ELISA, PCR, and/or qPCR.

In some embodiments, the virus preparation is assessed for residual impurities or contaminants. In some embodiments, the amount of residual impurities or contaminants is compared to the amount of impurities or contaminants at an earlier stage in the purification process, such as, e.g., directly after viral harvest. In some embodiments, the relative reduction of impurities in the final virus preparation is between 60-95% relative to the presence of impurities at an earlier stage in the purification process. In some embodiments, the relative reduction of impurities in the final virus preparation is approximately 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%. In some embodiments, the final virus preparation contains less than 5% impurities or contaminants. In some embodiments, the final virus preparation contains less than 5, 4, 3, 2, 1, 0.9, 0.8, 0.7, 0.6, 0.5, 0.4, 0.3, 0.2, or less than 0.1% impurities. In a preferred embodiment, the final virus preparation contains less than 1% impurities.

Any of the processes described herein may be used in the manufacture of a composition comprising purified virus for administration to a subject. In some embodiments, the subject is a mammalian subject, such as a human or a non-human animal, including livestock, pets or companion animals. In some embodiments, the composition is administered to a subject in need of immunization against the virus or similar virus as that of the virus preparation. In some embodiments, the virus preparations or compositions comprising viruses purified using the processes described herein are for treating or preventing infection with the virus or a similar virus as that of the virus preparation. In a preferred embodiment, the virus preparations or compositions comprising viruses purified using the processes described herein are for treating or preventing a Chikungunya virus infection, particularly a Chikungunya virus infection caused by West African, East/Central/South African (ECSA) and/or Asian genotypes of Chikungunya virus.

The CHIKV-Δ5nsP3 pharmaceutical compositions or CHIKV-Δ5nsP3 viruses purified using the processes described herein may be administered to a subject by any route known in the art. In some embodiments, the preparations or compositions may be administered via conventional routes, such as parenterally or orally. As used herein, "parenteral" administration includes, without limitation, subcutaneous, intracutaneous, intradermal, intravenous, intramuscular, intraarticular, intraperitoneal, intrathecal or by infusion.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

TABLE A-1

| Abbreviations | | | |
| --- | --- | --- | --- |
| Abbreviation | Definition | Abbreviation | Definition |
| CHIKV | Chikungunya virus | MVSB or P1-MVSB | Master virus seed bank (Passage 1 after rescue) |
| CHIKV-Δ5nsP3 | CHIKV with a defined deletion mutation in nsP3 (SEQ ID NO: 1) | WVSB or P2-WVSB | Working virus seed bank (Passage 2 after rescue) |
| ECSA | East-central south African | VRP | Virus replicon particle |
| E (1, 2, 3) proteins | Envelope proteins | TCID$_{50}$ | Tissue culture infective dose |
| C protein | Capsid protein | LR-VRP | VRP based on the La Reunion CHIKV isolate |
| 6K protein | 6 kilodalton protein | BHK(-21) | Baby hamster kidney cells |
| nsP | Non-structural protein | MOI | Multiplicity of infection |
| MEM | Minimum essential medium | M | Million |
| EMEM | Eagle's MEM | T75, T150, T175 | T flask 75, 150, 175 cm$^2$ |
| FBS | Fetal bovine serum | RB850 | Roller bottle 850 cm$^2$ |
| PBS | Phosphate buffered saline | Prob. F | Probability as determined by the F-test in one-way analysis of variance |
| Pfu | Plaque forming unit | ANOVA | Analysis of variance |
| PRNT | Plaque reduction neutralization test | DS | Drug substance |
| NGS | Next generation sequencing | GLuc | Gaussia luciferase |
| h | hour | GMP | Good manufacturing practice |
| d | Day | R&D | Research and development |
| AA | Amino acid | SEC | Size exclusion chromatography |
| PCR | Polymerase chain reaction | SDS-PAGE | Sodium dodecyl sulfate-polyacrylamide gel electrophoresis |

TABLE A-1-continued

| | Abbreviations | | |
|---|---|---|---|
| Abbreviation | Definition | Abbreviation | Definition |
| qPCR | Quantitative PCR | ELISA | Enzyme-linked Immunosorbant Assay |
| s.c. | Subcutaneous | w/w | Weight/weight |
| TSE | Transmissible Spongiform Encephalopathy | mL | Milliliter |
| p.i. | Post-infection | CPE | Cytopathic effect |
| PP | Polypropylene | V | Volts |
| μF | Micro-Farad | mM | millimolar |
| μm | micrometer | TBS | Tris-buffered saline |
| kDa | kilodalton | NaCl | Sodium chloride |
| mg | milligram | LR2006-OPY1 | La Reunion CHIKV isolate |
| RNA | Ribonucleic acid | D-PBS | Dulbecco's phosphate buffered saline |
| Anti-anti | Antibiotic-antimycotic | RPM | Rotations per minute |
| SINV | Sindbis virus | RRV | Ross River virus |
| SFV | Semliki Forest virus | MCB | Master cell bank |
| WHO | World Health Organization | ATCC | American Type Culture Collection |

EXAMPLES

Example 1. Initial Trials for CHIKV-Δ5nsP3 Drug Substance (DS) Production

Assembly of Synthesized CHIKV-Δ5nsP3 Genome

Figure 1:
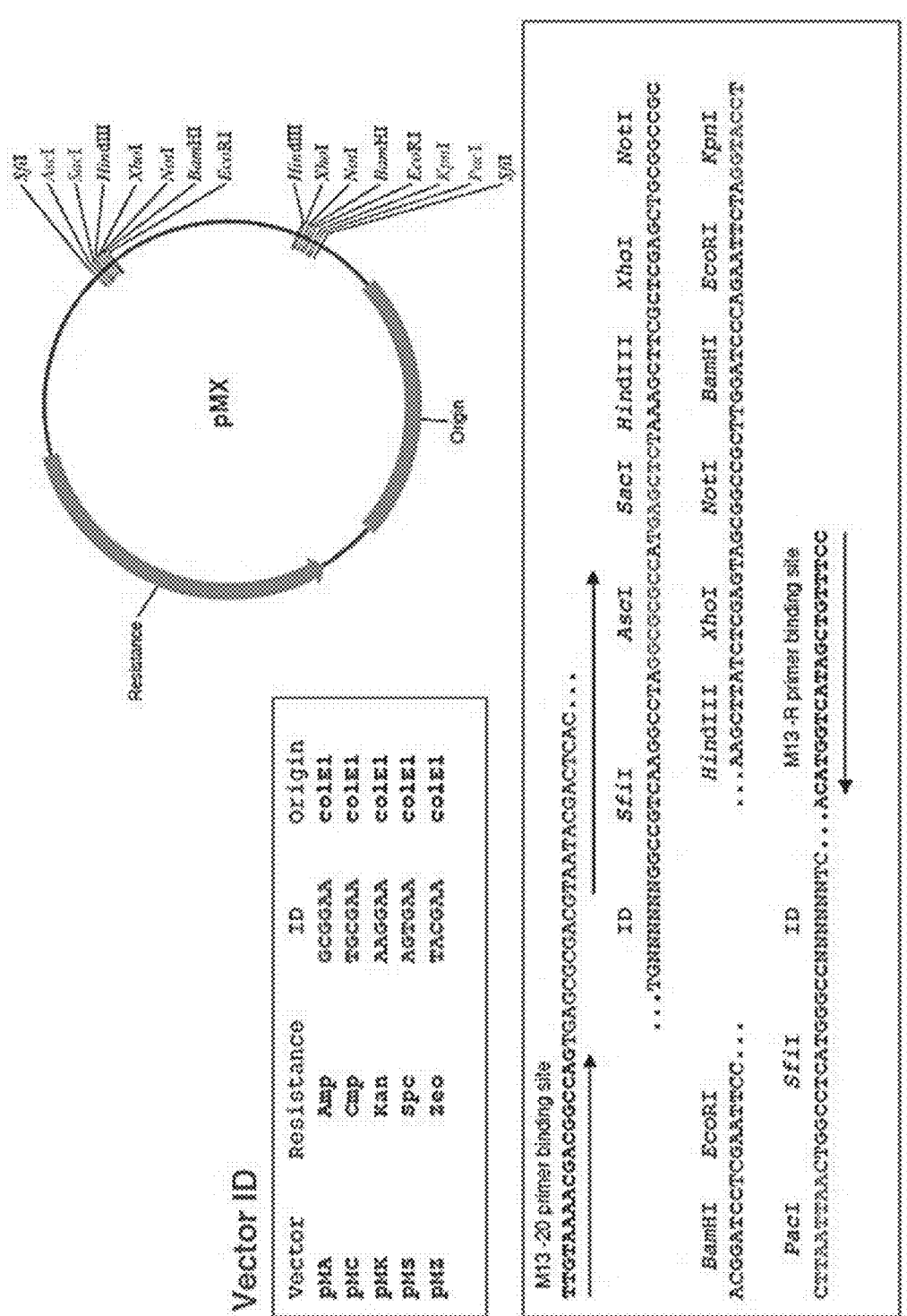
FIG. 1 Map of pMX plasmid used for full assembly of the CHIKV-Δ5nsP3 genome from synthesized fragments. For the full assembly of the CHIKV-Δ5nsP3 sequence, the pMX plasmid with an Ampicillin resistance cassette (pMA) was used. The pMX vector series is based on pUC-like cloning vectors, but leaves out unnecessary promoters (biosafety level 1).
Figure 3A:
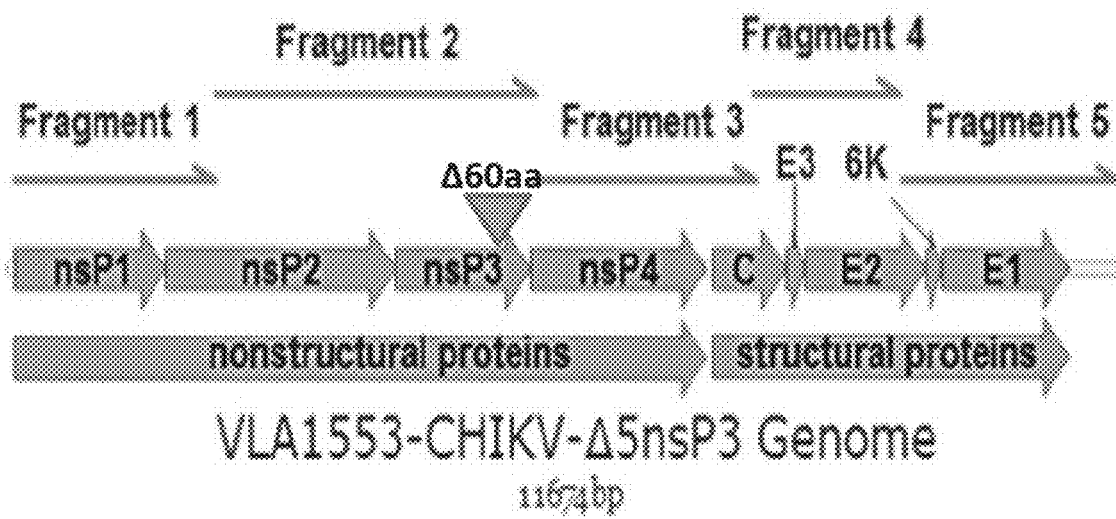
FIGS. 3A and 3B Cloning strategy for assembly of the CHIKV-Δ5nsP3 genome in pMA.
Figure 3B:
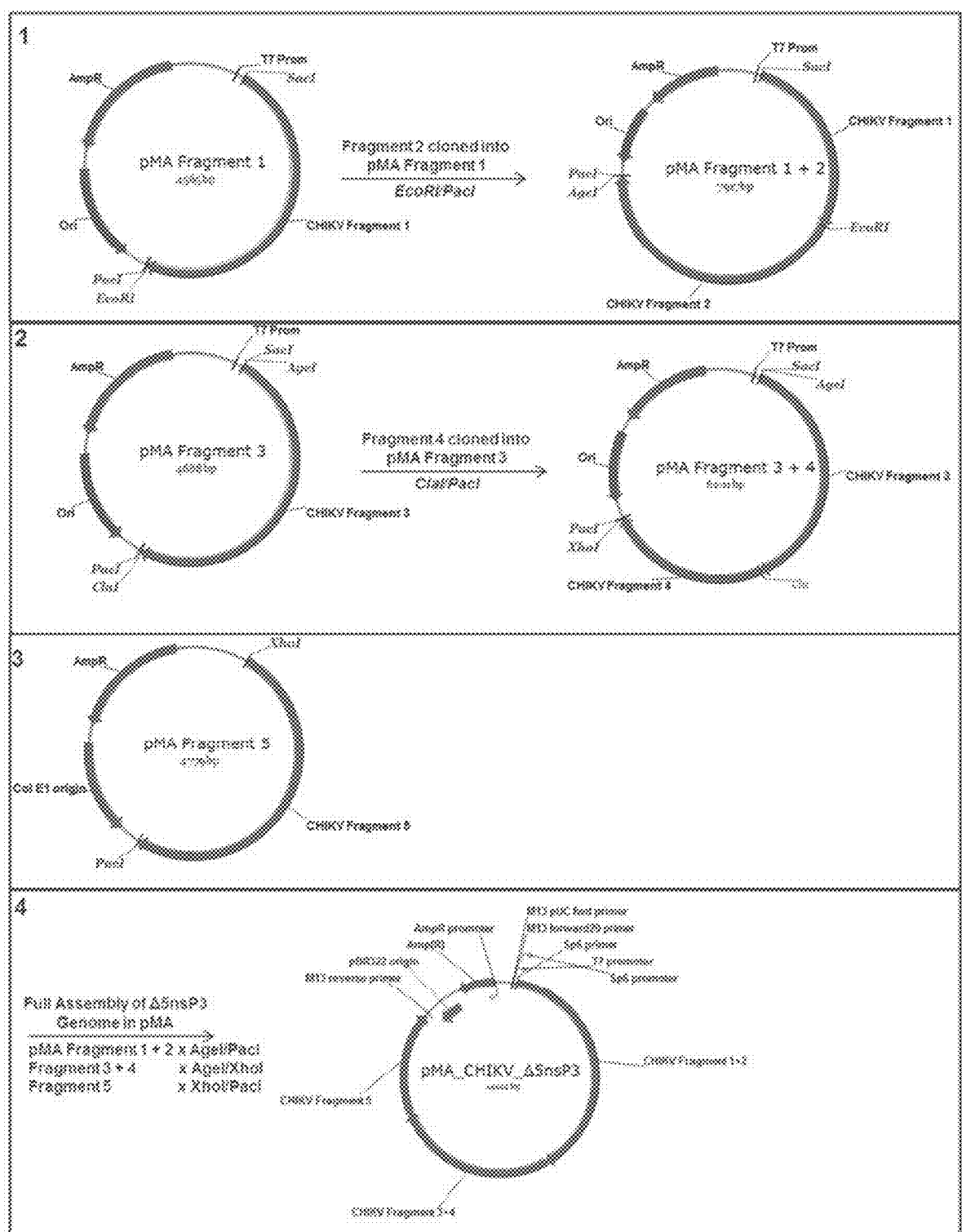

The CHIKV-Δ5nsP3 virus genome was synthesized in five fragments at MWG Eurofins (Germany) and was fully assembled in the pMA plasmid (pMX vector with ampicillin resistance), a standard cloning vector. The pMX vector backbone is shown in FIG. 1. All cloning and plasmid preparation procedures were carried out under TSE-free conditions using electro-competent NEB10β *E. coli* cells. The cloning strategy used for the full assembly of the CHIKV-Δ5nsP3 genome in pMA is outlined in FIG. 3B. Briefly, the pMA plasmid containing fragment 1, which covers nsP1 and part of nsP2 (as shown in FIG. 3A), was linearized via EcoRI/PacI restriction digestion and fragment 2 covering parts of nsP2 and nsP3 was fused to fragment 1. In parallel, fragment 3 (covering nsP4 and C) was fused to fragment 4 (covering C and E2) via ClaI/PacI cloning. In a third cloning step, fragments 3 and 4 were cloned via AgeI/XhoI and fragment 5 via XhoI/PacI into the AgeI/PacI-linearized pMA already containing fragments 1 and 2. The cloning resulted in the pMA_CHIKV-Δ5nsP3 vector encoding CHIKV-Δ5nsP3, as verified by sequencing.

CHIKV-Δ5nsP3 Rescue From Vero Cells ("Virus Rescue")

Figure 2:
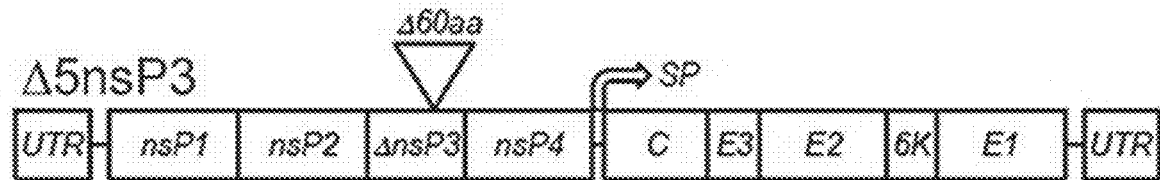
FIG. 2 Schematic illustration of the CHIKV-Δ5nsP3 genome structure. The Chikungunya virus genome encodes two polyproteins: non-structural proteins 1-4 (nsP1-4) and structural proteins (C, E3, E2, 6K, E1). Compared with the wild-type genomic sequence, the CHIKV-Δ5nsP3 sequence contains a 183-bp deletion in the 3' part of the sequence encoding nsP3 (amino acids 1656 to 1717 in the nsP1-4 polyprotein), which results in a 60 amino acid deletion in the nsP3 replicase protein (indicated by Δ60aa). SP, subgenomic promoter; UTR, untranslated region. (Figure adapted from Hallengärd D, et al., 2014, supra.)

For the production of CHIKV-Δ5nsP3 virus particles from the engineered pMA_CHIKV-Δ5nsP3 vector on Vero cells (virus rescue), the pMA_CHIKV-Δ5nsP3 plasmid was linearized by NotI restriction digestion and subjected to in vitro transcription using Ambion's mMessage mMachine SP6 Kit (AM130). RNA integrity was confirmed via gel electrophoresis (not shown). In parallel, Vero cells were prepared for electroporation with viral RNA. Briefly, Vero cells were detached from cell culture flasks using TrypLESelect (Gibco) and washed twice with PBS. All centrifugation steps were performed at 300 g at room temperature. Viral RNA was mixed with $8 \times 10^6$ Vero cells in 800 μl PBS and the Vero cell/RNA mix was transferred into 0.4 cm electroporation cuvettes. Two pulses were performed at 850 V, 25 μF, 200 Ohm. After electroporation, Vero cells were kept at room temperature for 10 minutes and finally resuspended in MEM/5% FCS/1% Antibiotic-Antimycotic (Anti-Anti)/2 mM L-Glutamine and incubated in T75 flasks for 48 hours at 35° C./5% $CO_2$. Cell culture supernatant containing rescued CHIKV-Δ5nsP3 (passage 0; P0) was harvested and centrifuged at 3,000 g for 10 minutes at 4° C. The virus titer was determined by plaque and $TCID_{50}$ assay on Vero cells. The rescued CHIKV-Δ5nsP3 (P0) was stored at −80° C. The genomic structure of the thus obtained CHIKV-Δ5nsP3 virus vaccine candidate, also referred to as VLA1553, is shown in FIG. 2.

Verification of CHIKV-Δ5nsP3 Sequence

In order to verify the viral genome sequence, viral nucleic acids were extracted from harvested cell culture supernatant using the QIAamp MinElute Virus Spin Kit (QIAGEN #57704) and cDNA-synthesis was done using the SuperScript III First-Strand Synthesis System (Life Technologies, Catalog #18080-051) using random hexamers. PCR with Phusion High Fidelity Polymerase was performed with primers amplifying overlapping regions of the CHIKV-Δ5nsP3 genome, and the PCR products were subjected to Sanger sequencing at MWG Eurofins, Germany. The sequences of primer pairs used for PCR and sequencing are shown in Table 1.

TABLE 1

Primer pairs used for CHIKV-Δ5nsP3 genome sequencing.

| Primer | Forward primer sequence (5'-3') restriction sites (lower case) | SEQ ID NO: | Reverse primer sequence (5'-3') restriction sites (lower case) | SEQ ID NO: |
|---|---|---|---|---|
| 1 | ttaggatccGATGGCTGCG TGAGACAC | 8 | taactcgagCCGTCAGGTCT GTTGAACAT | 9 |
| 2 | ttaggatccTACCACCAGG CGATTAAAG | 10 | taactcgagCTTTGCCCACT TACTGAAGG | 11 |
| 3 | ttaggatccTGCTACAGAA GTCACGCC | 12 | taactcgagGCCAAAGCGTG AATCAG | 13 |
| 4 | ttaggatccAACAGCTTGA GGACAGAGCG | 14 | taactcgagCTCTGTCTCAT CACGTCGG | 15 |
| 5 | ttaggatccAAAATTGCAGT CATAGGAGTCTTC | 16 | taactcgagAGTACGTTGAC GTGCTCTGA | 17 |

TABLE 1-continued

Primer pairs used for CHIKV-Δ5nsP3 genome sequencing.

| Primer | Forward primer sequence (5'-3') restriction sites (lower case) | SEQ ID NO: | Reverse primer sequence (5'-3') restriction sites (lower case) | SEQ ID NO: |
|---|---|---|---|---|
| 6 | ttaggatccGTGGGTTAAA CAACTGCAAA | 18 | taactcgagGGTTAAAGTCT TCTATCCTCCTGG | 19 |
| 7 | ttaggatccGGATAACCAC TGGGATAATAGG | 20 | taactcgagAGTTGTGAAAT TCCTTCTGCC | 21 |
| 8 | ttaggatccCGCAGATAGA ACCAGTGAAC | 22 | taactcgagCAGCAGCTCTA CTTGGGTC | 23 |
| 9 | ttaggatccAGGAGGGAA AGACAGGCT | 24 | taactcgagCCCTCGCCTTC TTCTG | 25 |
| 10 | ttaggatccCAAAATAGAA GGAGTGCAAAAG | 26 | taactcgagCCTGGAGTTTC TTAAGTAATAGTTGC | 27 |
| 11 | ttaggatccACCGGTCCAG GTCATTTA | 28 | taactcgagGCAGCAAATTC TTCCCAG | 29 |
| 12 | ttaggatccCCATTCCAGA ACACACTACAG | 30 | taactcgagATACCTGATTT CATCATGGC | 31 |
| 13 | ttaggatccCCTTTGATAA GAGCCAAGATG | 32 | taactcgagTACAAAGTTAT GACGGGTCCT | 33 |
| 14 | ttaggatccCAACGAACAG GGCTAATTG | 34 | taactcgagGACCGCTTAAA GGCCAG | 35 |
| 15 | ttaggatccGTGCATGAAA ATCGAAAATG | 36 | taactcgagTGGTCTTGTGG CTTTATAGACA | 37 |
| 16 | ttaggatccAACCGGAGG AAACCCTAC | 38 | taactcgagGTACCGCACCG TCTGG | 39 |
| 17 | ttaggatccAGCTACCTTG CAGCACGT | 40 | taactcgagCCCACCATCGA CAGG | 41 |
| 18 | ttaggatccCGAGCCGTAT AAGTATTGGC | 42 | taactcgagCGCCGGTGAAG ACCTTAC | 43 |
| 19 | ttaggatccACTACTGTCA GTCACTTTGGAGC | 44 | taactcgagTACCGGGTTTG TTGCTATTT | 45 |
| 20 | ttaggatccCACAACTGGT ACTGCAGAGAC | 46 | taactcgagGCGTAGCCCTT TGATCTATAG | 47 |
| 21 | ttaggatccGGTGCTATGC GTGTCGT | 48 | taactcgagATCTCCTACGT CCCTGTGGG | 49 |

Passaging of CHIKV-Δ5nsP3 on Vero Cells

Following rescue of CHIKV-Δ5nsP3, Vero cells were infected and the virus was serially passaged in three replicates (see Table 2). For passaging. Vero cells seeded in T150 flasks and grown to confluency (1-3 days) were washed twice with 1×DPBS before the addition of 20 mL infection medium (EMEM w/o serum). Inoculum was added directly to the flask at the indicated volume and the cells were incubated for 24 h at 35° C., 5% $CO_2$. Passaging was done in three replicates (A, B and C) with infection of Vero cells at an MOI of 0.01 for the first passage from virus rescue (P0). The 20 mL harvests were transferred to a 50 mL PP tube 24 h p.i., cell debris was removed by centrifugation (3000 g, 10 min) and the supernatant transferred to a fresh 50 mL PP tube. A 49% (w/w) sucrose solution was added to a final concentration of 10% (w/w) and 1 mL aliquots of stabilized harvest were stored at ≤−70° C.

Subsequent infections were carried out with harvest without sucrose. The infections were carried out using different volumes of harvest which were roughly calculated based on the observed cytopathic effect in the previous passage and in parallel replicates. Volumes of harvest used for infection varied between 5 μL and 1 mL. Infections were followed by a single harvest after 24 h. Note that the MOI used for production of passages 2-16 was determined retrospectively after $TCID_{50}$ results were available, resulting in a wide ("uncontrolled") range of MOIs throughout the experiment (See Table 2). This procedure was performed up to 16 passages in the three parallel replicates (replicates A, B and C) allowing systematic observation of various parameters during adaptation of CHIKV-Δ5nsP3 to Vero cell passaging. During this experiment, yield ($TCID_{50}$/mL), volume of infection, number of Vero cells per flask, Vero cell passage number and cytopathic effect (CPE) were recorded. The multiplicity of infection (MOI) was determined retrospectively based on the measured $TCID_{50}$ and also recorded. The CHIKV-Δ5nsP3 passages were simultaneously assessed for plaque size in all three replicates.

TABLE 2

Serial passaging of CHIKV-Δ5nsP3 on Vero cells following virus rescue, performed in triplicate. Data shown include harvest yield (24 h; TCID$_{50}$), infection volume (mL), number of cells/flask, Vero cell passage number, multiplicity of infection (MOI) and observed cytopathic effect (CPE) at 24 h post-infection.

| Passage | TCID$_{50}$/ mL | In- fection (mL) | Cells @ T150 | Vero passage | MOI (TCID$_{50}$) | CPE @ 24 h |
|---|---|---|---|---|---|---|
| | | | Replicate A | | | |
| P0 | 9.77E+06 | | | | | n.a. |
| P1A | 2.59E+07 | 0.02 | 2.00E+07 | 149 | 0.010 | 50 |
| P2A | 1.90E+07 | 1 | 2.90E+07 | 149 | 0.893 | 50 |
| P3A | 2.92E+07 | 0.1 | 2.80E+07 | 149 | 0.068 | 20 |
| P4A | 2.14E+08 | 0.37 | 2.00E+07 | 150 | 0.540 | 90 |
| P5A | 1.01E+08 | 0.1 | 2.70E+07 | 150 | 0.792 | 60 |
| P6A | 3.50E+08 | 0.1 | 2.60E+07 | 150 | 0.390 | 60 |
| P7A | 7.43E+08 | 0.037 | 1.30E+07 | 151 | 0.997 | 50 |
| P8A | 8.02E+08 | 0.05 | 1.60E+07 | 151 | 2.323 | 90 |
| P9A | 1.51E+09 | 0.01 | 2.40E+07 | 151 | 0.334 | 60 |
| P10A | 3.60E+09 | 0.005 | 1.98E+07 | 152 | 0.381 | 80 |
| P11A | 1.88E+09 | 0.005 | 1.84E+07 | 152 | 0.982 | 90 |
| P12A | 6.94E+08 | 0.005 | 1.30E+07 | 152 | 0.724 | 90 |
| P13A | 4.22E+09 | 0.01 | 1.44E+07 | 153 | 0.482 | 60 |
| P14A | 3.05E+09 | 0.01 | 1.90E+07 | 153 | 2.219 | 90 |
| P15A | 3.03E+09 | 0.01 | 2.20E+07 | 153 | 1.384 | 90 |
| P16A | 2.91E+09 | 0.01 | 1.70E+07 | 154 | 1.781 | 90 |
| | | | Replicate B | | | |
| P0 | 9.77E+06 | | | | | n.a. |
| P1B | 6.47E+07 | 0.02 | 2.00E+07 | 149 | 0.010 | 50 |
| P2B | 5.32E+07 | 1 | 2.90E+07 | 149 | 2.232 | 50 |
| P3B | 2.27E+07 | 0.1 | 2.80E+07 | 149 | 0.190 | 20 |
| P4B | 1.65E+08 | 0.08 | 2.00E+07 | 150 | 0.091 | 80 |
| P5B | 1.65E+08 | 0.1 | 2.70E+07 | 150 | 0.613 | 60 |
| P6B | 4.06E+08 | 0.1 | 2.60E+07 | 150 | 0.636 | 60 |
| P7B | 9.19E+08 | 0.092 | 1.30E+07 | 151 | 2.875 | 60 |
| P8B | 7.43E+08 | 0.1 | 1.60E+07 | 151 | 5.744 | 90 |
| P9B | 2.14E+09 | 0.025 | 2.40E+07 | 151 | 0.774 | 75 |
| P10B | 4.06E+09 | 0.01 | 1.98E+07 | 152 | 1.080 | 90 |
| P11B | 2.09E+09 | 0.01 | 1.84E+07 | 152 | 2.214 | 90 |
| P12B | 8.76E+08 | 0.01 | 1.30E+07 | 152 | 1.608 | 90 |
| P13B | 2.91E+09 | 0.01 | 1.44E+07 | 153 | 0.609 | 60 |
| P14B | 4.22E+09 | 0.01 | 1.90E+07 | 153 | 1.530 | 90 |
| P15B | 3.79E+09 | 0.01 | 2.20E+07 | 153 | 1.917 | 95 |
| P16B | 3.79E+09 | 0.01 | 1.70E+07 | 154 | 2.232 | 90 |
| | | | Replicate C | | | |
| P0 | 9.77E+06 | | | | | n.a. |
| P1C | 3.24E+07 | 0.02 | 2.00E+07 | 149 | 0.010 | 50 |
| P2C | 3.29E+07 | 1 | 2.90E+07 | 149 | 1.117 | 50 |
| P3C | 2.54E+07 | 0.1 | 2.80E+07 | 149 | 0.118 | 20 |
| P4C | 1.29E+08 | 0.15 | 2.00E+07 | 150 | 0.191 | 90 |
| P5C | 4.13E+08 | 0.1 | 2.70E+07 | 150 | 0.477 | 60 |
| P6C | 5.91E+08 | 0.1 | 2.60E+07 | 150 | 1.587 | 60 |
| P7C | 1.85E+09 | 0.185 | 1.30E+07 | 151 | 8.415 | 70 |
| P8C | 4.83E+08 | 0.2 | 1.60E+07 | 151 | 23.073 | 90 |
| P9C | 1.03E+09 | 0.1 | 2.40E+07 | 151 | 2.013 | 90 |
| P10C | 5.14E+09 | 0.015 | 1.98E+07 | 152 | 0.783 | 90 |
| P11C | 1.51E+09 | 0.015 | 1.84E+07 | 152 | 4.205 | 90 |
| P12C | 1.15E+09 | 0.015 | 1.30E+07 | 152 | 1.738 | 90 |
| P13C | 4.22E+09 | 0.01 | 1.44E+07 | 153 | 0.802 | 65 |
| P14C | 3.81E+09 | 0.01 | 1.90E+07 | 153 | 2.219 | 90 |
| P15C | 1.07E+09 | 0.01 | 2.20E+07 | 153 | 1.730 | 90 |
| P16C | 2.48E+09 | 0.01 | 1.70E+07 | 154 | 0.631 | 90 |

Trends Observed During Serial Passaging Under "Uncontrolled" MOI Conditions

During CHIKV-Δ5nsP3 adaptation to Vero cell passaging, it was observed that total CHIKV-Δ5nsP3 virus yield increased substantially with increased passage number on Vero cells as shown in Table 2. As shown in FIG. 4A, passages 6 and above yielded an approximately 100-fold increase in titer compared with virus rescue (P0) and early passages. Also observed was a concomitant decrease in CHIKV-Δ5nsP3 plaque size (FIG. 4B). The effect of in vitro passaging of wild-type Chikungunya virus on plaque size in other cell lines has been previously described by Gardner C L, et al. (Gardner C L, et al., 2014, supra). A high virus yield would be highly desirable for industrial production of the inactivated virus; however, it was also herein observed that CHIKV-Δ5nsP3 became less immunogenic with increased passaging as shown in FIG. 4C. Briefly, to determine the immunogenicity of different passages of CHIKV-Δ5nsP3 as generated in Table 2, above, groups of five C57Bl/6 mice were immunized once subcutaneously with a dose of 10$^5$ TCID$_{50}$ CHIKV-Δ5nsP3 passage 5 (P5B), passage 8 (P8B) or P15 (P15C). CHIKV-Δ5nsP3 at P0 (virus rescue), also at 10$^5$ TCID$_{50}$, was used as a positive control. Day 21 serum pools were assessed for their capacity to neutralize CHIKV-Δ5nsP3 (P0) in a PRNT assay on Vero cells, by testing 4-fold serial serum dilutions ranging from 1:20 to 1:327,680. As shown in FIG. 4C, the immunogenicity in mice of the P5B CHIKV-Δ5nsP3 showed slightly shifted immunogenicity compared with the unpassaged CHIKV-Δ5nsP3 (P0), whereas a P8B virus showed substantially reduced immunogenicity comparable to the P15C virus. (As the P15C virus was non-immunogenic, it served as a negative control in subsequent PRNT assays.)

Finally, selected passages of the CHIKV-Δ5nsP3 were tested for genetic stability by Sanger sequencing. Upon passaging of CHIKV-Δ5nsP3 on Vero cells up to 16 times, it was verified that the 60 amino acid deletion in the nsP3 gene responsible for the attenuation of the virus was genetically stable, indicating that the virus does not revert back to wild-type, an important safety consideration for live attenuated vaccines.

Trends Observed During Serial Passaging Under Controlled MOI Conditions

The use of high MOIs (e.g., higher than 0.1) is not conducive to an industrial scale process as too much starting material is needed. In this regard, the use of a lower MOI (0.01) over three passages was tested and the immunogenicity of the resulting passages was determined. As shown in FIG. 5A, three passages from Replicate B in Table 2, were passaged under uncontrolled conditions, with MOIs ranging from 0.01 to 2.23. From the thus-obtained passage 3 (P3B), further passages were done up to P6 using an MOI of 0.01 for each passage and shown as "controlled conditions at MOI 0.01" in FIG. 5A. Under conditions using an MOI of 0.01, the immunogenicity of the resulting virus was lost very quickly as shown in FIG. 5B. By passage 5, the CHIKV-Δ5nsP3 was rendered non-immunogenic. This result was in contrast to the results seen with P5B in FIG. 4C, which was produced with a much higher MOI (see Table 2, Replicate B) and was still immunogenic. This observation seemed to indicate that a lower MOI leads to faster selection during Vero cell passaging for mutations that affect the immunogenicity of CHIKV-Δ5nsP3.

Example 2. Defining Sequence Heterogeneities of CHIKV-Δ5nsP3 Which Affect Immunogenicity Due to the observed reduction/loss of immunogenicity (neutralizing antibody titer) and decreased plaque size at higher CHIKV-Δ5nsP3 passages, it was of interest to analyze possible sequence heterogeneities within the viral populations at different passage numbers. In addition, it was of interest to analyze the sequence of individual plaques of the viral population. Unpassaged CHIKV-Δ5nsP3 (P0) did not show sequence heterogeneities based on Sanger sequencing. In general, with increased passage numbers an increase in sequence heterogeneities for all 3 replicates was observed (Replicates A, B and C; Table 3). In the case of passaging replicate C at passage 8 (P8C), the virus population was still heterogeneous (sequence heterogeneities shown in Table 3), whereas the P15C passage showed a more homogenous virus population with defined point mutations (indicated by *). The immunogenicity data shown in FIG. 4C (Example 1, above) focused on P5B and P8B, which showed sequence heterogeneities in the CHIKV-Δ5nsP3 non-structural proteins (nsP) and envelope protein E2 as shown in Table 3 below.

22

0.01 was added and the cells were incubated for 24 h at 35° C., 5% $CO_2$. The 100 mL harvests were transferred to 50 mL PP tubes 24 h p.i. and the cell debris was removed by centrifugation, followed by a 0.2 μm filtration using Steri-flip® vacuum filtration devices (Merck). Individual clarified virus harvests were first concentrated using Amicon® Centrifugal Filter devices, diafiltrated to TBS buffer and purified by protamine sulphate and Capto™ Core700 treatment. Purified CHIKV-Δ5nsP3 clones were then used for further studies.

TABLE 3

Sequence heterogeneities in CHIKV-Δ5nsP3 at passages P5, P8 and P15 (Replicates A, B and C as produced in Table 2). Sequence heterogeneities were determined by Sanger sequencing. For that purpose, viral nucleic acids were extracted from harvested cell culture supernatant using the QIAamp MinElute Virus Spin Kit (Qiagen). The cDNA was synthesized using the SuperScript III First-Strand Synthesis System (ThermoFischer) using random hexamers. PCR with Phusion High Fidelity Polymerase was performed with primers amplifying overlapping regions of the CHIKV-Δ5nsP3 genome (Table 1), which were sequenced by Sanger sequencing at MWG Eurofins, Germany. The readout shows results of automated base calling (>20%) as well as heterogeneities detected by visual analyses of sequencing chromatograms.

| | Replicate A | | | Replicate B | | | Replicate C | | |
|---|---|---|---|---|---|---|---|---|---|
| Gene | P5A | P8A | P15A | P5B | P8B | P15B | P5C | P8C | P15C |
| | | | | Sequence Heterogeneities | | | | | |
| nsP2 | | | | | | L4941 | | | |
| | | G577W | G577W | | G577W | G577W | | G577W | G577W* |
| | | | | | | G621R | | | |
| nsP3 | | | | | R470S | R470S | | | |
| nsP4 | | | | | V113I | | | | |
| E2 | | G55R | G55R | | G55R | G55R | G55R | G55R | G55R* |
| | | | | | H99Y | H99Y | | | |
| | E168K | | | E168K | E168K | E168K | | | |
| | | | M171V | | | | | | |
| | | T230I | T230I | | T230I | T230I | | T230I | T230I* |
| | | H232Y | H232Y | | | | | | |
| | E247K | | | | | | E247K | | |
| | | E247D | | | E247D | | | E247D | |
| | A423A | | | A423A | | | | | |

*Full mutations (i.e., 100%) are indicated by an asterisk.

Expansion and Sequencing of Single CHIKV-Δ5nsP3 Plaques

To understand the effect of individual mutations on immunogenicity and consequently develop a controlled and reproducible production process for a highly immunogenic CHIKV-Δ5nsP3 vaccine, individual plaques from CHIKV-Δ5nsP3 isolates P5B and P8B were picked. Briefly, serial dilutions of P5B and P8B CHIKV-Δ5nsP3 were used for infection of Vero cells in a plaque assay (described under FIGS. 4A-4C) and after an incubation of 72 hours, single plaques of different morphologies were picked (small plaques were preferentially picked, since they began to appear after several passages on Vero cells) and expanded via re-infection of Vero cells ($5 \times 10^5$) in 6-well plates. The different CHIKV-Δ5nsP3 samples that derived from single plaques were selected based on mutations in the E2 gene sequence prior to one further expansion on Vero cells. Clones P5B-02, P5B-03, P5B-04, P5B-07, P5B-11, P8B-01 and P8B-05 were expanded and purified for in vivo immunogenicity experiments. Individual plaques were expanded on Vero cells grown in Roller Bottles using a single 850 cm² Roller Bottle with CellBIND® surface for each isolate. Upon reaching confluency, cells were washed twice with 100 mL D-PBS+Ca+Mg before 100 mL infection medium (EMEM w/o serum) containing the inoculum at an MOI of The full genome sequences of the expanded CHIKV-Δ5nsP3 samples, P5B+1 and P8B+1; namely P5B-02, P5B-03, P5B-04, P5B-07, P5B-11, P8B-01 and P8B-05 as described above, derived from single plaques, P5B and P8B, respectively, were assessed by Sanger sequencing. The observed point mutations of the individual plaques are summarized in Table 4 and schematic genomic sequences are shown in FIG. 6B and FIG. 6D.

In order to assess the effect of specific point mutations on the immunogenicity of CHIKV-Δ5nsP3, day 19 mouse sera from mice immunized with the individual plaque-derived viruses were generated and analyzed in PRNT. Briefly, a single dose of CHIKV-Δ5nsP3 at an intended $TCID_{50}$ dose of $10^5$ was administered subcutaneously to C57Bl/6 mice (10 per treatment group) and pools of day 19 sera were analyzed in a PRNT assay at 4-fold serial dilutions ranging from 1:20 to 1:327,680 for their virus neutralization capacity. The virus that was neutralized in the PRNT corresponded to a passage 2 CHIKV-Δ5nsP3 (P2, 560 pfu/ml) which did not show sequence heterogeneities and therefore was identical in sequence to the unpassaged CHIKV-Δ5nsP3 (P0). The neutralization mix (560 pfu/ml CHIKV-Δ5nsP3 P2 and serial serum dilutions) was incubated for 1 hour at room temperature and added onto Vero cells, followed by incubation for 2 hours. Finally, a methylcellulose overlay (0.8%) was added followed by incubation for 72 hours. The plaque readout was done following crystal violet staining (0.5% crystal violet in 5% Formaldehyde).

TABLE 4

Mutations in single picked plaques of P5 and P8 CHIKV-Δ5nsP3 passages. Sequencing of the full CHIKV-Δ5nsP3 genome was performed at MWG Eurofins, Germany, using the primers in Table 1. All P5B and P8B clones corresponded to a P6 (P5B + 1) and P9 (P8 + 1) CHIKV-Δ5nsP3, respectively, expanded on Vero cells. The PRNT$_{50}$ titers were calculated in GraphPad Prism using non-linear fit—3 parameter calculations. The viral protein in which the respective point mutations were identified are shown in brackets. PRNT$_{50}$ values for non-immunogenic isolates were not measurable as indicated.

| Experiment # | Isolate | Passage | Point mutation(s) | Immunogenicity | PRNT$_{50}$ |
|---|---|---|---|---|---|
| 4399gr1 | P0 #1 | 0 | N/A | Positive control | 386 |
| 4415gr1 | P0 #2 | 0 | N/A | Positive control | 4215 |
| 4415gr2 | P5B-02 | 5 + 1 | E168K[E2] + A38S[nsP1] | retained | 373 |
| 4415gr3 | P5B-03 | 5 + 1 | H232Y[E2] | retained | 112 |
| 4415gr4 | P5B-04 | 5 + 1 | E168K[E2] | lost | — |
| 4415gr5 | P5B-07 | 5 + 1 | E168K[E2] | lost | — |
| 4415gr6 | P5B-11 | 5 + 1 | E247K[E2] | retained | 219 |
| 4415gr7 | P8B-01 | 8 + 1 | H99Y/ E168K[E2] + R470S[nsP3] | lost | — |
| 4415gr8 | P8B-05 | 8 + 1 | G55R/ H232Y[E2] + G577W[nsP2] | lost | — |
| 4399gr2 | P15C-DS | 15 | G55R/ T230I[E2] + G577W[nsP2] | Negative control | — |

— = not measurable

Figure 6A:
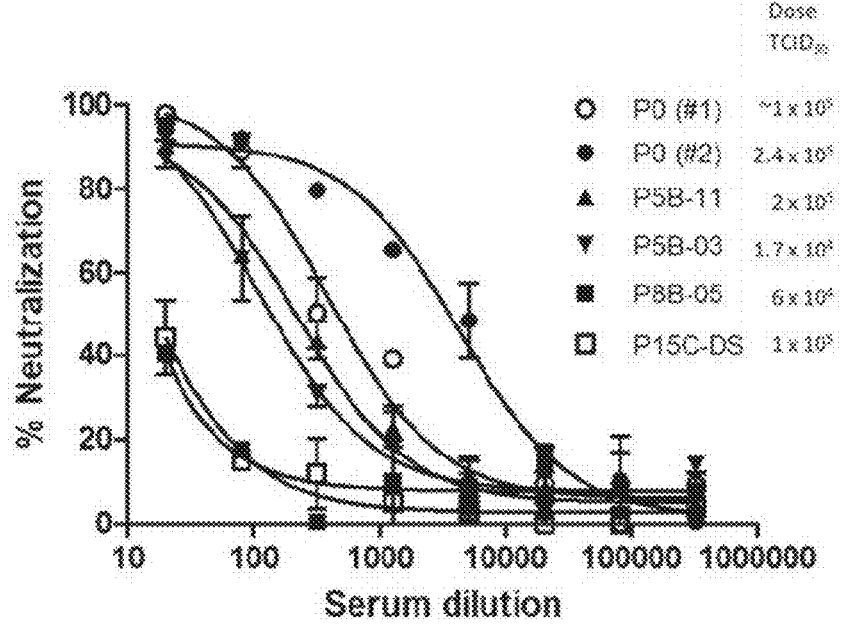
Figure 6B:
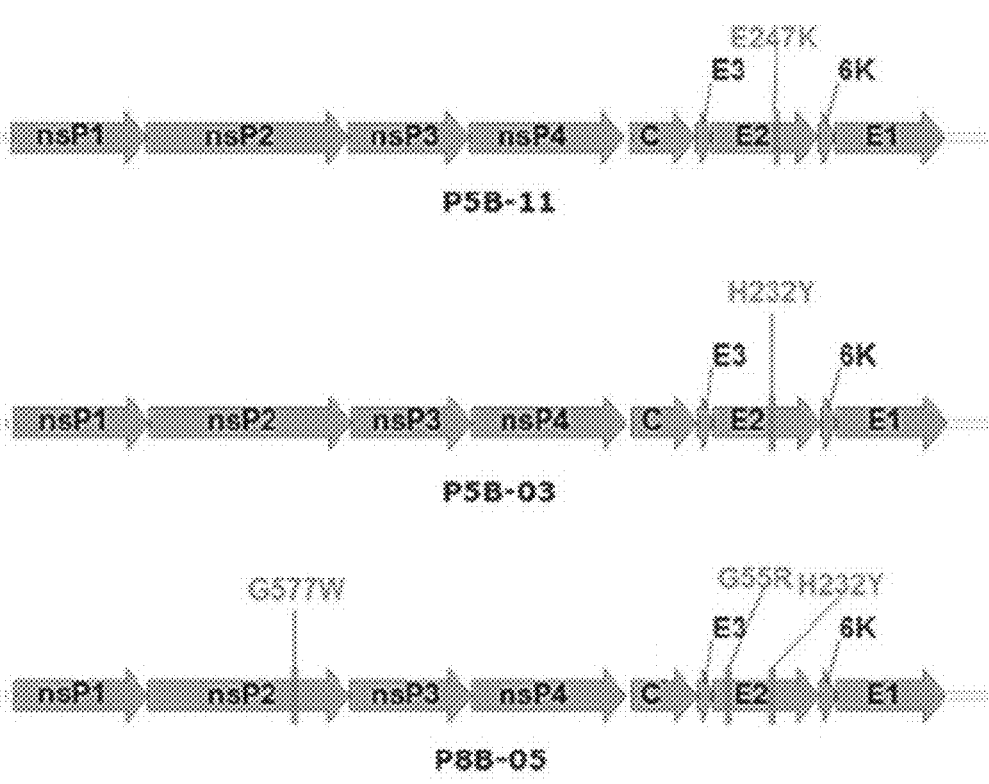

As can be seen in FIG. 6A, the immunogenicity of CHIKV-Δ5nsP3 P5B-11 and P5B-03, both with single point mutations in the E2 protein, E247K and H232Y (FIG. 6B), respectively, is not affected when compared to the immunogenicity of P0 CHIKV-Δ5nsP3. The neutralization capacity of P0 serum is shown from two independent mouse experiments (4415; P0 #2 and 4399; P0 #1) delineating the acceptable range of immunogenicity. On the other hand, P8B-05, characterized by 3 point mutations, G577W, G55R and H232Y in nsP2 and E2, respectively, is non-immunogenic in mice. The G55R mutation was already described in literature by Gardner C L, et al., as being a result of passaging CHIKV in vitro. The viral particle is affected by an increased dependence on heparan sulfate binding in vitro which leads to an attenuation in vivo (Gardner C L, et al., 2014, supra).

Figure 6C:
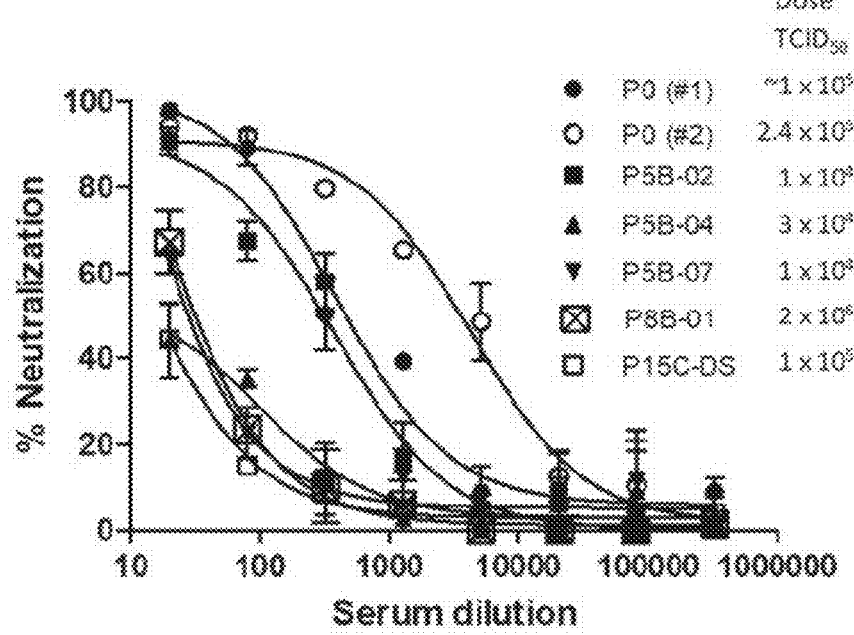
Figure 6D:
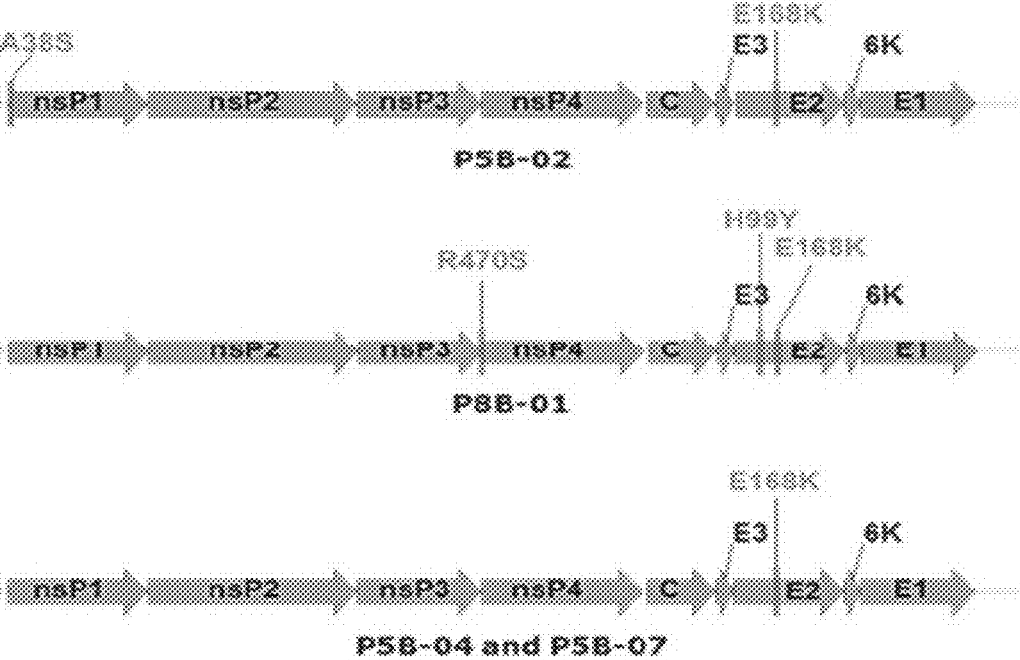

As can be seen in FIG. 6C, only one of the four CHIKV-Δ5nsP3 samples derived from single plaques (P5B-02) was still immunogenic and was characterized by two point mutations, A38S and E168K in nsP1 and E2 (FIG. 6D), respectively. Also, P8B-01 with three point mutations, R470S in the nsP3 and H99Y and E168K in the E2 protein, was non-immunogenic in mice and was comparable to the negative control P15C. P5B-04 and P5B-07 each had single point mutations in E2, i.e., Glutamic acid 168 was mutated to a Lysine (E168K), which was also shown to have a direct effect on immunogenicity, since CHIKV-Δ5nsP3 neutralization capacity was lost.

In summary, it was observed that many of the mutations arising during passaging on Vero cells were located in the E2 protein. Some of the identified point mutations in the E2 protein and/or other parts of the genome did not substantially affect immunogenicity of the virus; particularly the H232Y[E2] and E247K[E2] mutations. However, some of the other identified mutations in the CHIKV-Δ5nsP3 resulted in loss of immunogenicity; particularly the frequently-occurring E168K[E2] mutation, whether alone or in combination with other mutations. An interesting exception was the mutant with both E168K[E2] and A38S[nsP1] mutations, which maintained immunogenicity. This observation suggests that the A38S[nsP1] mutation has a mitigating effect on the reduced immunogenicity conferred by the E168K[E2] mutation. Furthermore, an isolate with G55R/ H232Y[E2] and G577W[nsP2] mutations also demonstrated poor immunogenicity, perhaps mainly due to the G55R mutation in E2, as the H232Y mutation alone had little effect (sec P5B-03).

The E168K and G55R mutations in Chikungunya virus E2 protein were previously described as conferring increased positive surface charge, leading to increased interaction with heparan sulfate and/or other Glycosaminoglycans (GAGs), ultimately resulting in increased specific infectivity. On the background of wild-type CHIKV, the mutations were shown to cause a smaller plaque size, due to lower spread on plates mediated by binding to heparan sulfate. Furthermore, the mutations resulted in attenuation of CHIKV in a mouse model of musculoskeletal disease (MSD), with decreased spread in mice to organs and thus lower levels of viremia (Gardner C L, et al., 2014, supra; Silva L A, et al., A single-amino-acid polymorphism in Chikungunya virus E2 glycoprotein influences glycosaminoglycan utilization (2014) J Virol.; 88(5):2385-97). The fact that the presence of E168K and G55R mutations in an otherwise wild-type CHIKV resulted in intermediate attenuation is consistent with the present disclosure with regard to reduced plaque size or reduced immunogenicity in vivo. However, it was unexpected that the said two mutations on the background of the attenuated CHIKV-Δ5nsP3 would result in loss of immunogenicity in mice as reported herein.

It has also been reported as a common phenomenon for other cell culture passaged alphaviruses such as Sindbis virus (SINV; Klimstra W B, et al., Infection of neonatal mice with Sindbis virus results in a systemic inflammatory response syndrome (1999) J. Virol.; 73(12):10387-98; Klimstra W B, et al., The furin protease cleavage recognition sequence of Sindbis virus PE2 can mediate virion attachment to cell surface heparan sulfate (1999) J. Virol.; 73(8): 6299-306; Byrnes and Griffin, Binding of Sindbis virus to cell surface heparan sulfate (1998) J. Virol.; 72(9):7349-56), Ross River virus (RRV; Heil M L, et al., An amino acid substitution in the coding region of the E2 glycoprotein adapts Ross River virus to utilize heparan sulfate as an attachment moiety (2001) J. Virol.; 75(14):6303-9) and Semliki Forest virus (SFV; Smit J M, et al., Adaptation of alphaviruses to heparan sulfate: interaction of Sindbis and Semliki forest viruses with liposomes containing lipid-conjugated heparin (2002) J. Virol.; 76(20):10128-37) that substitutions for positively-charged residues in E2 confer enhanced heparan-sulfate dependent infectivity in vitro and that these mutations can be selected within a few serial in vitro passages. Further, it was shown that such mutations led to attenuation of the viruses in vivo (Byrnes A P and D E Griffin, Large-plaque mutants of Sindbis virus show reduced binding to heparan sulfate, heightened viremia, and slower clearance from the circulation (2000) J. Virol.; 74(2):644-51; Klimstra W B, et al. 1999, supra).

Because sequence heterogeneities, with a concomitant drop in immunogenicity, were already apparent at passages P5 and P8 of CHIKV-Δ5nsP3, sequence heterogeneities at earlier passages, as well as their effects on immunogenicity, were examined more closely as outlined below.

Example 3. Defining Sequence Heterogeneities and Immunogenicity of CHIKV-Δ5nsP3 at Passage P3

The occurrence at later passages of sequence heterogeneities with adverse effects on the immunogenicity of CHIKV-Δ5nsP3 as measured by neutralizing antibody titers warranted finding the optimal passage which was characterized by both high immunogenicity as well as a viral titer sufficient for production of an effective vaccine.

To determine genetic stability of the CHIKV-Δ5nsP3 during MVSB (P1), WVSB (P2) and CHIKV-Δ5nsP3 drug substance ("VLA1553") (P3) production, independently generated passages 1, 2 and 3 were sequenced. As determined by Sanger sequencing, P0 (virus rescue), P1 (MVSB) and P2 (WVSB) did not show any obvious sequence heterogeneities. The next step was to demonstrate reproducibility of genetic stability of P3 derived purified drug substance (DS) using P2 (WVSB) for infection. In total, four independent P3 harvests, consisting of combined day 1 and day 2 harvests, were produced in two T150 T-flasks using P2 (WVSB) for infection (MOI 0.01). For each replicate, the individual harvests at day 1 and day 2 were pooled (total volume~50 mL) and concentrated approximately 10-fold (Amicon 100 kDa ultrafiltration device). Diafiltration was done against 25 mM Tris/150 mM NaCl, pH 7.4, followed by protamine sulfate treatment (2 mg/mL final concentration) to precipitate host cell DNA. The clear supernatant was then further purified by batch adsorption chromatography using CaptoCore 700 resin (addition of ~1 mL of 50% slurry in Tris/NaCl buffer). The resin was removed by centrifugation and sucrose was added to a final concentration of 10% to allow freezing and thawing of CHIKV-Δ5nsP3. The final formulation was then 0.2 μm sterile filtered and stored frozen (<−65° C.) until further processing.

At passage 3 (P3), no heterogeneities by automatic base calling were detected (Eurofins—all <20%). However, by visual inspection, a small fraction of the viral population showed a consistent increase in the E168K and E247K sequence heterogeneities in the gene for the CHIKV glycoprotein E2, which was absent in the rescued CHIKV-Δ5nsP3 (P0) as well as the MVSB and WVSB samples. FIG. 7 shows sequencing chromatograms for the four independently generated P3 DS samples (Examples 1-4) compared with the virus at passage 0 (P0). As indicated by the box outlines, a G/A heterogeneity at the codon for amino acid 168 (genomic nucleic acid position 8882) was detectable in all four replicates and verified by the reverse sequencing reaction, which revealed the same heterogeneity. The same position in the P0 sample showed a sharp peak for G in the forward sequencing reaction (and C in the reverse sequencing reaction). The E247K heterogeneity (genomic nucleic acid position 9119), on the other hand, was present but barely detectable in the sequencing chromatograms.

Additionally, next generation sequencing of P3 was carried out and compared with sequencing of passage 1 (P1-MVSB) in order to quantify the amount of E168K and E247K within the viral population. As can be seen in FIGS. 8A-8C, at the stage of P1-MVSB, only a very low level of sequence heterogeneities was detectable (all below background; 15% cut-off indicated by the dotted line). The two representative P3 sample, however, showed an overall increase in sequence heterogeneities, with two mutations in the E2 gene that reached or rose above background (E168K in 18% and 15% of the viral population—genomic nucleic acid position 8882 and, to a lower extent, E247K—genomic nucleic acid position 9119).

In summary, the presence of an E168K mutation in the E2 protein of CHIKV-Δ5nsP3 was identified by Sanger sequencing and NGS in eight independently-generated P3 samples, demonstrating the reproducibility of this result. Representative sequencing examples are shown in FIG. 7 and FIGS. 8A-8C. These data demonstrate that the emergence of an E168K mutation in the E2 protein of CHIKV-Δ5nsP3 virus was highly reproducible upon passaging in Vero cells and that it diminished the immunogenicity of the attenuated CHIKV-Δ5nsP3 virus as shown in Example 2 where P5B plaque-derived viruses (P5B-04 and P5B-07 in FIGS. 6A-6D) were non-immunogenic. Two additional mutations, G55R and G82R, which were observed during passaging of CHIKV-Δ5nsP3 on Vero cells, like E168K have been reported to affect the virulence of CHIKV (Gardner C L, et al., 2014, supra, Silva L A, et al., 2014, supra and Gorchakov R, et al., Attenuation of Chikungunya virus vaccine strain 181/clone 25 is determined by two amino acid substitutions in the E2 envelope glycoprotein (2012) J. Virol.; 86(11):6084-96; Epub 2012 Mar. 30), leading to attenuation of the virus. Since these two mutations also negatively impacted the immunogenicity of CHIKV-Δ5nsP3, their emergence should be avoided for the production of a highly immunogenic CHIKV-Δ5nsP3 vaccine candidate.

The locations of amino acids prone to mutation within the E1/E2 dimer are shown in FIGS. 9A-9C. The three E2 amino acids G55, G82 and E168 are all accessible on the surface and therefore their mutation may potentially affect interactions of CHIKV with its cellular receptors. In contrast, E247[E2] is more buried within the protein structure and thus may not be surface exposed to the same extent. The position of E247 may be one reason why the E247K mutation did not noticeably affect the immunogenicity of CHIKV-Δ5nsP3 as shown above.

Example 4. Determining the Threshold of the E168K Mutation for Loss of Immunogenicity of a Heterogeneous CHIKV-Δ5nsP3 Virus Population The above observations indicated that the E168K[E2] mutation appears early and frequently during passaging of CHIKV-Δ5nsP3 on Vero cells and is associated with lost immunogenicity. In order to develop a process for the reliable manufacture of an effective, immunogenic live-attenuated Chikungunya virus vaccine, the tolerance for this mutation in a sample of the CHIKV-Δ5nsP3 vaccine was tested by preparing different ratios of the P3 drug substance and the virus P5B-07 (E168K single mutant; see Table 3).

Passage 3 (P3) drug substance, which displayed about 20% E168K heterogeneity (data not shown), was mixed with a preparation of CHIKV-Δ5nsP3 from the P5B-07 isolate (E168K mutant) at ratios of 1:0.1, 1:1 and 1:10. The mixtures were sequenced to verify the approximate frequency of the E168K mutation in each virus preparation. As shown in FIG. 10 (see row labeled heterogeneity), the relative amount of nucleotide A, compared with the wild-type nucleotide G, was shown to increase with increasing levels of added P5B-07 isolate (up to 100% A in the E168K control group 7).

Figures 11A, 11B, 11C, 11D:
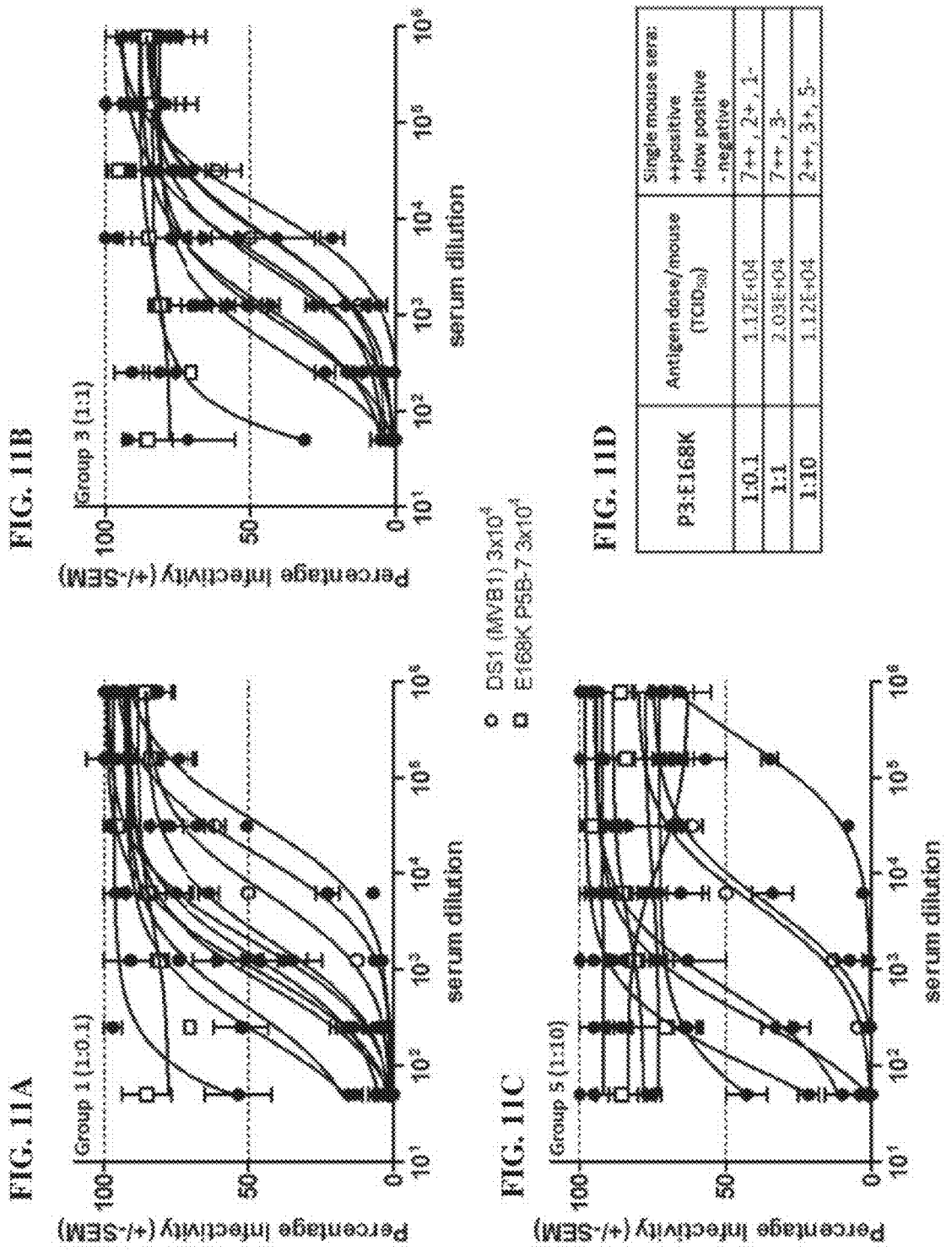

In order to determine the effect of the E168K mutation on immunogenicity, C57Bl/6 mice were immunized s.c. with the different CHIKV-Δ5nsP3 samples specified in FIG. 10 with an intended dose of $3 \times 10^4$ $TCID_{50}$ (actual dose shown in FIG. 11D). Day 21 mouse sera were collected and individual sera from the 1:0.1, 1:1 and 1:10 groups were tested and compared with pooled sera from the two control groups, P3 (Group 6) and P5B-07 (E168K; Group 7) using a virus replicon particle (VRP)-based neutralization assay (FIGS. 11A-11D). VRPs resemble a replication deficient wild-type CHIKV displaying capsid and envelope proteins of the LR2006-OPY1 virus. The method was carried out essentially as described by Gläsker S, et al. (Virus replicon particle based Chikungunya virus neutralization assay using Gaussia luciferase as readout (2013) Virol. J.; 10:235). The VRPs were produced by co-transfecting BHK-21 cells with a CHIKV replicon expressing Gaussia luciferase (GLuc) and two helper RNAs expressing wild-type CHIKV capsid protein and the remaining structural proteins (E3, E2, 6K and E1), respectively. The resulting single round infectious particles were used in the CHIKV neutralization assay using secreted GLuc as a readout. Upon neutralization of VRPs in the Luciferase assay, a reduction of GLuc expression by BHK-21 cells can be measured. It was observed that the capacity for eliciting neutralizing immunity dropped with higher amounts of the E168K mutant (FIGS. 11A, 11B and 11C, respectively). The number of individual mice showing either positive, low positive or negative immune responses to Chikungunya virus is shown in FIG. 11D.

This finding confirms that, as the ratio of E168K mutant to wild-type viral particles in a virus population increases, the immunogenicity of CHIKV-Δ5nsP3 in mice is diminished. It is therefore crucial to closely monitor position E168 in E2 to ensure high immunogenicity of the CHIKV-Δ5nsP3 vaccine. Based on previous passaging processes and quantification of E168K within the viral population at passage 8, it was observed that at a rate of about 70% of the E168K mutation within the CHIKV-Δ5nsP3 population, the immunogenicity was lost when analyzing mouse serum pools in PRNT.

Example 5. Upstream Process for Reducing E168K Mutations in CHIKV-Δ5nsP3

The aim of this example was to characterize an optimized Vero cell culture based process for the production of CHIKV-Δ5nsP3 in roller bottles. The impact of several upstream process parameters (MOI, day of Vero cell infection following plating and incubation temperature) on viral productivity and sequence heterogeneity of the E2 protein were tested using the GMP Working Virus Seed Bank (GMP WVSB B3005044; passage 2, also referred to herein as "P2 CHIKV-Δ5nsP3") and the R&D Vero working cell bank to produce drug substance (DS; passage 3, i.e. also referred to herein as "P3 CHIKV-Δ5nsP3").

Preparation of GMP WVSB B3005044

A characterized Pre-Master Virus Seed Bank (PMVSB, Pre-Master Virus Seed Bank AFR886/197579 from virus rescue from Vero cells) was established under R&D conditions and a Pre-Master Virus Seed Bank was used to generate the Master Seed Banks of the CHIKV-Δ5nsP3 under GMP conditions. The GMP Working Virus Seed Bank, VLA78-1553-WVSB-2016, batch B3005044 was produced at Halix B.V. under the same production method and GMP conditions as described for the VLA78-1553-MVSB-2016, batch #B3005567. Briefly, the VERO Working Cell Bank (internal designation: ICB 2014/002) was expanded in four stages in a seed train using T75 cm² flasks (1×), then T175 cm² flasks (3×) and in the last stage 6×850 cm² roller bottles as shown in FIG. 12. Four of the six roller bottles were used for production of the CHIKV-Δ5nsP3 seed banks. The total amount of cells in the four roller bottles was determined. The Pre-Master Virus Seed Bank was used to generate the CHIKV-Δ5nsP3 Master Virus Seed Bank. Subsequently, the CHIKV-Δ5nsP3 Master Virus Seed Bank was used to generate the CHIKV-Δ5nsP3 Working Virus Seed Bank. Infection was done at all stages at an MOI of 0.01. After 24 hours of infection (35° C.; 5% $CO_2$; 0.5 RPM) the CHIKV-Δ5nsP3 was harvested. Tris and sucrose stock solution was added to a final concentration of 5% Sucrose and 25 mM Tris in the harvest pool. After formulation, the pool was filtered through a steam sterilized 0.22 μm filter into a sterile 500 mL bio process container by using a peristaltic pump. Filling of vials was done one by one with 0.7 mL formulated and filtered harvest using a peristaltic filling pump. A ThermoFisher capper/decapper device was used to open and close the 2D Matrix Cryo vials. Filled vials of the GMP seed banks were stored at <−65° C.

Culture of Vero Cells

Culturing of Vero cells was performed at 35° C. and 5% $CO_2$ in T75 cm² (T75), T175 cm² (T175) T-Flasks and 850 cm² roller bottles (850RB). Vero cells used in the different experiments were derived from the GMP master cell bank MCB ICB/2014/001. The internal designation of this research working cell bank was Bk5685. The GMP master cell bank was derived from the WHO Vero cell bank 10-87 P134 which originated from the Institut Merieux (Aventis Pasteur) P129 bank and ultimately from the original ATCC CCL 81 P113 bank. More detail regarding the cell culture train is shown in FIG. 12. Cells were maintained in MEM medium supplemented with 10% FBS and 2 mM L-glutamine.

Virus Production in 850 cm² Roller Bottles

Following two, four or five days of cell expansion at 35° C. in 850RB, cells were washed with PBS and infected with the CHIKV-Δ5nsP3 (WVSB B3005044) at MOIs of 0.1, 0.01 or 0.001 $TCID_{50}$/cell. For virus production, infected cells were incubated at 37° C., 35° C. or 28° C. in 100 mL of MEM medium supplemented with 2 mM glutamine.

Virus Titration

Virus titers were determined on Vero cells using the $TCID_{50}$ assay. Cells were seeded in microplates and infected with 10-fold serially diluted virus samples in EMEM supplemented with 0.5% FBS and 2 mM glutamine. After a one week incubation at 35° C./5% $CO_2$, virus-induced cytopathic effects were monitored and viral titers were calculated according to the Reed and Muench method (Reed, L. J.; Muench, H. A simple method of estimating fifty percent endpoints (1938) The American Journal of Hygiene 27:493-497).

Virus Genome Extraction and Sequencing

Viral nucleic acid was extracted and purified from Vero cell culture supernatant at the indicated timepoints using QIAamp MinElute Virus Spin Kit (Qiagen) and cDNA synthesis was performed using SuperScript III First-Strand Synthesis System (ThermoFischer) using random hexamers. For sequencing of the E2 gene region, first, PCRs with Phusion High Fidelity Polymerase (ThermoFischer) were done using primers 16F, 16R, 17F, 17R, 18F and 18R (for primer sequences see Table 1) to amplify overlapping regions of the CHIKV E2 gene. After purification of PCR amplicons, Sanger sequencing was performed at MWG Eurofins, Germany. In addition to analyses of sequence heterogeneities that were detected by automatic base calling (>20%), all sequencing chromatograms were manually read to detect also heterogeneities below the detection limit (<20%).

Optimization of a Process for Producing an Immunogenic P3 CHIKV-Δ5nsP3 Drug Substance To optimize the process for producing passage 3 CHIKV-Δ5nsP3 on Vero cells, different MOIs, times of Vero cell infection post-seeding and temperatures of incubation were tested in all combinations as shown in Table 5. Additionally, yields were analyzed at different days following infection. Three aspects of the harvested virus were monitored: viral productivity, stability of the titer as well as the level of sequence heterogeneity of the E2 structural protein.

TABLE 5

Parameters tested for production of CHIKV-Δ5nsP3 on Vero cells in 850 cm² roller bottles and the parameters of the identified optimized process.

|  | Tested* | Optimized Process |
| --- | --- | --- |
| MOI (TCID$_{50}$/cell) | 0.1, 0.01, 0.001 | 0.01 |
| Time of cell infection (post cell seeding) | D 2, D 4, D 5 | D 4 |
| Temperature (° C.) | 37, 35, 28 | 35 |

*all combinations were performed.

Virus Production

CHIKV-Δ5nsP3 production kinetics achieved for all the conditions tested are shown in FIGS. 13A-13C. The optimal process currently used to produce CHIKV-Δ5nsP3 (35° C., MOI 0.01, infection on day 4 after Vero cell seeding) was also included in the experiment, showing virus productivity at the expected level of $10^{8.0-8.5}$/mL 24 h after infection (FIG. 13B).

Compared to MOI and time of infection, temperature had the most impact on viral production kinetics. At 37° C. and 35° C. (FIG. 13A and FIG. 13B, respectively), maximum productivity was achieved at day one post-infection. The CHIKV-Δ5nsP3 infectivity dropped substantially during the subsequent 24 hours, with a slightly less pronounced viral titer loss at 35° C. Temperature reduction to 28° C. resulted in a striking change of the viral kinetics. Maximal viral productivity was delayed one to four days depending on the MOI used; and significantly improved virus titer stability was observed (FIG. 13C). The total virus yield produced from all of the harvests is shown in FIG. 14. For the 28° C. condition as shown in FIG. 13A, the yield of two harvests were combined (day 1 and day 2 post-infection); for the 35° C. condition (FIG. 13B), the yield of all three harvests were combined (days 1-3) and for the 37° C. condition (FIG. 13C), the yield of five harvests (days 1-5) were combined.

To complete initial observations, viral productivity and titer stability data were analyzed using a response surface quadratic model (FIGS. 15A-15B and FIGS. 16A-16B). For viral productivity, the maximum virus titer values were used. For virus titer stability, the delta value resulting from the subtraction of the maximum titer from the titer measured one day later in the production process was calculated and used. For total virus productivity, the individual titers at each time point were added.

With ANOVA analysis of both models, it was possible to indicate the statistically significant influencing factors (FIGS. 15A and 16A). Confirming previous observations, temperature was the strongest factor affecting viral productivity and stability. In particular, low temperatures (28° C.) enabled higher viral titers while keeping the virus titer reasonably stable over time. However, there was not a significantly higher overall total virus productivity at this temperature compared with 35° C. (see esp. FIG. 14).

Time of infection after Vero cell seeding also influenced the response, but to a lower extent. MOI did not have a significant impact. For both models, infection at 72 h post cell seeding was an adequate time for cell infection. Conversely, a single temperature did not allow combining optimal virus production and titer stability since the highest viral yields were found at 35° C. and the most stabilized titers were observed at 28° C. (FIGS. 15B and 16B). Maximumal total virus productivity within the shortest time post infection was achieved at 35° C. (see FIG. 14).

Analysis of E2 Protein Gene Sequence

Virus samples collected at either day 2 or day 5 after infection of Vero cells (infected at day 4 post-seeding) were selected to conduct an analysis of genomic RNA sequence of the viral E2 structural protein. These samples are most representative for Vero cell confluence on roller bottles. Tables 6 and 7 below summarize the percentage of heterogeneities estimated for four amino acid (AA) positions based on the nucleic acid sequence determined by Sanger sequencing. Table 6 shows data for CHIKV-Δ5nsP3 grown at three different temperatures and harvested two days post-infection and Table 7 shows data for CHIKV-Δ5nsP3 grown at 28° C. and harvested 5 days post-infection.

TABLE 6

Analysis of RNA genome sequence for E2 viral protein from D 2 post-infection sample harvests. Shown are the estimated percentages of nucleic acid heterogeneities corresponding to four AA positions (indicated in parentheses), as determined by Sanger sequencing. The heterogeneity at nucleic acid position 9649 is a silent mutation.

| | Time post seeding in roller bottles D 4 Temperature | | | | | | | | |
| --- | --- | --- | --- | --- | --- | --- | --- | --- | --- |
| | 28° C. | | | 35° C. | | | 37° C. | | |
| MOI (TCID$_{50}$/cell) | 0.1 | 0.01 | 0.001 | 0.1 | 0.01 | 0.001 | 0.1 | 0.01 | 0.001 |
| Pos. 8543 (G55R) | 0 | 0 | 0 | 0-5 | 0-5 | 0-5 | 0 | 0 | 0 |
| Pos. 8882 (E168K) | 30 | 30 | 40-50 | 25 | 25 | 30-50 | 25 | 25 | 30-50 |
| Pos. 9119 (E247K) | 0-5 | 0-5 | 0-5 | 5-10 | 10 | 10-20 | 10-20 | 10-20 | 10-20 |
| Pos. 9649 (A423, Silent) | 0-5 | 5-10 | 10-20 | 5 | 5 | 5-10 | 0-5 | 0-5 | 5-10 |

TABLE 7

Analysis of RNA genome sequence for E2 viral protein from D 5 post-infection sample harvests. Shown are the estimated percentages of nucleic acid heterogeneities corresponding to four AA positions (indicated in parentheses), as determined by Sanger sequencing. The heterogeneity at nucleic acid position 9649 is a silent mutation.

| | Time post seeding in roller bottles D 4 Temperature 28° C. MOI (TCID$_{50}$/cell) | | |
| --- | --- | --- | --- |
| | 0.1 | 0.01 | 0.001 |
| Pos. 8543 (G55R) | 0 | 0 | 0 |
| Pos. 8882 (E168K) | 30-40 | 40-50 | 50 |
| Pos. 9119 (E247K) | 0-5 | 0-10 | 10 |
| Pos. 9649 (A423, Silent) | 0-5 | 0-5 | 10-20 |

MOI, temperature, day of infection post-Vero cell seeding and day of sample harvest all influenced the productivity and the quality of CHIKV-Δ5nsP3 when produced in Vero cells. The strength of each parameter, however, was of different importance. For example, the results suggested a correlation between MOI and heterogeneity levels; i.e., the lower the viral input at infection, the higher the observed level of heterogeneity at harvest. The incubation temperature did not appear to impact the stability of the nucleotide sequence, with the exception of Pos. 9119 (E247K) where a higher level of heterogeneity was observed at 37° C. (Table 6). Also, the sample harvest collected later in the viral kinetic triggered a slightly higher level of heterogeneity for the same AA position.

To complete this first analysis, mathematical modelling of the raw data was also performed (FIGS. 17A-17B and FIGS. 18A-18B). Only three nucleic acid positions (Pos. 8882, 9119, 9649) could be analyzed as no significant model was calculated for the position 8543. As indicated in FIGS. 17A-17B, temperature and MOI had different impacts depending on the nucleic acid position considered. The MOI significantly influenced the heterogeneities observed for nucleic acid positions 8882 and 9649, but not for 9112. The temperature affected positions 9112 and 9649, but not 8882 (FIGS. 17A-17B). MOI was shown to consistently influence the level of heterogeneity when D2 and D5 post-infection harvest samples from 28° C.-produced virus were compared—minimized levels of AA heterogeneity were observed when cells were inoculated with a high quantity of virus (MOI 0.1 TCID$_{50}$/cell). This observation might prompt the establishment of new process parameter settings with a higher MOI as a means to achieve maximal virus production/titer stability while ensuring a low level of heterogeneity within the E2 protein. However, an MOI of 0.1 results in significantly higher consumption of GMP working virus seed bank, thus limiting its practical industrial applicability.

Post-infection harvest day only impacted the variation of nucleic acid position 9119 (FIGS. 18A-18B).

```
SEQUENCES
Nucleotide sequence of the CHIKV-Δ5nsP3
                                        SEQ ID NO: 1
GATGGCTGCGTGAGACACACGTAGCCTACCAGTTTCTTACTGCTCTACTCTGCAAAG

CAAGAGATTAATAACCCATCATGGATCCTGTGTACGTGGACATAGACGCTGACAGC

GCCTTTTTGAAGGCCCTGCAACGTGCGTACCCCATGTTTGAGGTGGAACCAAGGCAG

GTCACACCGAATGACCATGCTAATGCTAGAGCGTTCTCGCATCTAGCTATAAAACTA

ATAGAGCAGGAAATTGACCCCGACTCAACCATCCTGGATATCGGCAGTGCGCCAGC

AAGGAGGATGATGTCGGACAGGAAGTACCACTGCGTCTGCCCGATGCGCAGTGCGG

AAGATCCCGAGAGACTCGCCAATTATGCGAGAAAGCTAGCATCTGCCGCAGGAAAA

GTCCTGGACAGAAACATCTCTGGAAAGATCGGGGACTTACAAGCAGTAATGGCCGT

GCCAGACACGGAGACGCCAACATTCTGCTTACACACAGACGTCTCATGTAGACAGA

GAGCAGACGTCGCTATATACCAAGACGTCTATGCTGTACACGCACCCACGTCGCTAT

ACCACCAGGCGATTAAAGGGGTCCGAGTGGCGTACTGGGTTGGGTTCGACACAACC

CCGTTCATGTACAATGCCATGGCGGGTGCCTACCCCTCATACTCGACAAACTGGGCA

GATGAGCAGGTACTGAAGGCTAAGAACATAGGATTATGTTCAACAGACCTGACGGA

AGGTAGACGAGGCAAGTTGTCTATTATGAGAGGGAAAAAGCTAAAACCGTGCGACC

GTGTGCTGTTCTCAGTAGGGTCAACGCTCTACCCGGAAAGCCGCAAGCTACTTAAGA

GCTGGCACCTGCCATCGGTGTTCCATTTAAAGGGCAAACTCAGCTTCACATGCCGCT

GTGATACAGTGGTTTCGTGTGAGGGCTACGTCGTTAAGAGAATAACGATGAGCCCA

GGCCTTTATGGAAAAACCACAGGGTATGCGGTAACCCACCACGCAGACGGATTCCT

GATGTGCAAGACTACCGACACGGTTGACGGCGAAAGAATGTCATTCTCGGTGTGCA

CATACGTGCCGGCGACCATTTGTGATCAAATGACCGGCATCCTTGCTACAGAAGTCA

CGCCGGAGGATGCACAGAAGCTGTTGGTGGGGCTGAACCAGAGAATAGTGGTTAAC
```

33

34

-continued

GGCAGAACGCAACGGAATACGAACACCATGAAAAATTATCTGCTTCCCGTGGTCGC

CCAAGCCTTCAGTAAGTGGGCAAAGGAGTGCCGGAAAGACATGGAAGATGAAAAA

CTCCTGGGGGTCAGAGAAAGAACACTGACCTGCTGCTGTCTATGGGCATTCAAGAA

GCAGAAAACACACACGGTCTACAAGAGGCCTGATACCCAGTCAATTCAGAAGGTTC

AGGCCGAGTTTGACAGCTTTGTGGTACCGAGTCTGTGGTCGTCCGGGTTGTCAATCC

CTTTGAGGACTAGAATCAAATGGTTGTTAAGCAAGGTGCCAAAAACCGACCTGATC

CCATACAGCGGAGACGCCCGAGAAGCCCGGGACGCAGAAAAAGAAGCAGAGGAAG

AACGAGAAGCAGAACTGACTCGCGAAGCCCTACCACCTCTACAGGCAGCACAGGAA

GATGTTCAGGTCGAAATCGACGTGGAACAGCTTGAGGACAGAGCGGGCGCAGGAAT

AATAGAGACTCCGAGAGGAGCTATCAAAGTTACTGCCCAACCAACAGACCACGTCG

TGGGAGAGTACCTGGTACTCTCCCCGCAGACCGTACTACGTAGCCAGAAGCTCAGTC

TGATTCACGCTTTGGCGGAGCAAGTGAAGACGTGCACGCACAACGGACGAGCAGGG

AGGTATGCGGTCGAAGCGTACGACGGCCGAGTCCTAGTGCCCTCAGGCTATGCAAT

CTCGCCTGAAGACTTCCAGAGTCTAAGCGAAAGCGCAACGATGGTGTATAACGAAA

GAGAGTTCGTAAACAGAAAGCTACACCATATTGCGATGCACGGACCAGCCCTGAAC

ACCGACGAAGAGTCGTATGAGCTGGTGAGGGCAGAGAGGACAGAACACGAGTACG

TCTACGACGTGGATCAGAGAAGATGCTGTAAGAAGGAAGAAGCCGCAGGACTGGTA

CTGGTGGGCGACTTGACTAATCCGCCCTACCACGAATTCGCATATGAAGGGCTAAAA

ATCCGCCCTGCCTGCCCATACAAAATTGCAGTCATAGGAGTCTTCGGAGTACCGGGA

TCTGGCAAGTCAGCTATTATCAAGAACCTAGTTACCAGGCAGGACCTGGTGACTAGC

GGAAAGAAAGAAAACTGCCAAGAAATCACCACCGACGTGATGAGACAGAGAGGTC

TAGAGATATCTGCACGTACGGTTGACTCGCTGCTCTTGAATGGATGCAACAGACCAG

TCGACGTGTTGTACGTAGACGAGGCGTTTGCGTGCCACTCTGGAACGCTACTTGCTT

TGATCGCCTTGGTGAGACCAAGGCAGAAAGTTGTACTTTGTGGTGACCCGAAGCAGT

GCGGCTTCTTCAATATGATGCAGATGAAAGTCAACTATAATCACAACATCTGCACCC

AAGTGTACCACAAAAGTATCTCCAGGCGGTGTACACTGCCTGTGACCGCCATTGTGT

CATCGTTGCATTACGAAGGCAAAATGCGCACTACGAATGAGTACAACAAGCCGATT

GTAGTGGACACTACAGGCTCAACAAAACCTGACCCTGGAGACCTCGTGTTAACGTG

CTTCAGAGGGTGGGTTAAACAACTGCAAATTGACTATCGTGGATACGAGGTCATGA

CAGCAGCCGCATCCCAAGGGTTAACCAGAAAAGGAGTTTACGCAGTTAGACAAAAA

GTTAATGAAAACCCGCTCTATGCATCAACGTCAGAGCACGTCAACGTACTCCTAACG

CGTACGGAAGGTAAACTGGTATGGAAGACACTTTCCGGCGACCCGTGGATAAAGAC

GCTGCAGAACCCACCGAAAGGAAACTTCAAAGCAACTATTAAGGAGTGGGAGGTGG

AGCATGCATCAATAATGGCGGGCATCTGCAGTCACCAAATGACCTTCGATACATTCC

AAAATAAAGCCAACGTTTGTTGGGCTAAGAGCTTGGTCCCTATCCTCGAAACAGCGG

GGATAAAACTAAATGATAGGCAGTGGTCTCAGATAATTCAAGCCTTCAAAGAAGAC

AAAGCATACTCACCTGAAGTAGCCCTGAATGAAATATGTACGCGCATGTATGGGGT

GGATCTAGACAGCGGGCTATTTTTCTAAACCGTTGGTGTCTGTGTATTACGCGGATAA

CCACTGGGATAATAGGCCTGGAGGGAAAATGTTCGGATTTAACCCCGAGGCAGCAT

CCATTCTAGAAAGAAAGTATCCATTCACAAAAGGGAAGTGGAACATCAACAAGCAG

-continued

```
ATCTGCGTGACTACCAGGAGGATAGAAGACTTTAACCCTACCACCAACATCATACC

GGCCAACAGGAGACTACCACACTCATTAGTGGCCGAACACCGCCCAGTAAAAGGGG

AAAGAATGGAATGGCTGGTTAACAAGATAAACGGCCACCACGTGCTCCTGGTCAGT

GGCTATAACCTTGCACTGCCTACTAAGAGAGTCACTTGGGTAGCGCCGTTAGGTGTC

CGCGGAGCGGACTACACATACAACCTAGAGTTGGGTCTGCCAGCAACGCTTGGTAG

GTATGACCTAGTGGTCATAAACATCCACACACCTTTTCGCATACACCATTACCAACA

GTGCGTCGACCACGCAATGAAACTGCAAATGCTCGGGGGTGACTCATTGAGACTGC

TCAAACCGGGCGGCTCTCTATTGATCAGAGCATATGGTTACGCAGATAGAACCAGTG

AACGAGTCATCTGCGTATTGGGACGCAAGTTTAGATCGTCTAGAGCGTTGAAACCAC

CATGTGTCACCAGCAACACTGAGATGTTTTTCCTATTCAGCAACTTTGACAATGGCA

GAAGGAATTTCACAACTCATGTCATGAACAATCAACTGAATGCAGCCTTCGTAGGAC

AGGTCACCCGAGCAGGATGTGCACCGTCGTACCGGGTAAAACGCATGGACATCGCG

AAGAACGATGAAGAGTGCGTAGTCAACGCCGCTAACCCTCGCGGGTTACCGGGTGG

CGGTGTTTGCAAGGCAGTATACAAAAAATGGCCGGAGTCCTTTAAGAACAGTGCAA

CACCAGTGGGAACCGCAAAAACAGTTATGTGCGGTACGTATCCAGTAATCCACGCT

GTTGGACCAAACTTCTCTAATTATTCGGAGTCTGAAGGGGACCGGGAATTGGCAGCT

GCCTATCGAGAAGTCGCAAAGGAAGTAACTAGGCTGGGAGTAAATAGTGTAGCTAT

ACCTCTCCTCTCCACAGGTGTATACTCAGGAGGGAAAGACAGGCTGACCCAGTCACT

GAACCACCTCTTTACAGCCATGGACTCGACGGATGCAGACGTGGTCATCTACTGCCG

CGACAAAGAATGGGAGAAGAAAATATCTGAGGCCATACAGATGCGGACCCAAGTA

GAGCTGCTGGATGAGCACATCTCCATAGACTGCGATATTGTTCGCGTGCACCCTGAC

AGCAGCTTGGCAGGCAGAAAAGGATACAGCACCACGGAAGGCGCACTGTACTCATA

TCTAGAAGGGACCCGTTTTCATCAGACGGCTGTGGATATGGCGGAGATACATACTAT

GTGGCCAAAGCAAACAGAGGCCAATGAGCAAGTCTGCCTATATGCCCTGGGGGAAA

GTATTGAATCGATCAGGCAGAAATGCCCGGTGGATGATGCAGACGCATCATCTCCCC

CCAAAACTGTCCCGTGCCTTTGCCGTTACGCTATGACTCCAGAACGCGTCACCCGGC

TTCGCATGAACCACGTCACAAGCATAATTGTGTGTTCTTCGTTTCCCCTCCCAAAGTA

CAAAATAGAAGGAGTGCAAAAAGTCAAATGCTCTAAGGTAATGCTATTTGACCACA

ACGTGCCATCGCGCGTAAGTCCAAGGGCTTATAGAGGTGCCGCTGCCGGTAACCTTG

CGGCCGTGTCTGATTGGGTAATGAGCACCGTACCTGTCGCGCCGCCCAGAAGAAGG

CGAGGGAGAAACCTGACTGTGACATGTGACGAGAGAGAAGGGAATATAACACCCAT

GGCTAGCGTCCGATTCTTTAGGGCAGAGCTGTGTCCGGTCGTACAAGAAACAGCGG

AGACGCGTGACACAGCAATGTCTCTTCAGGCACCACCGAGTACCGCCACGGAACCG

AATCATCCGCCGATCTCCTTCGGAGCATCAAGCGAGACGTTCCCCATTACATTTGGG

GACTTCAACGAAGGAGAAATCGAAAGCTTGTCTTCTGAGCTACTAACTTTCGGAGAC

TTCTTACCAGGAGAAGTGGATGACTTGACAGACAGCGACTGGTCCACGTGCTCAGA

CACGGACGACGAGTTAAGACTAGACAGGGCAGGTGGGTATATATTCTCGTCGGACA

CCGGTCCAGGTCATTTACAACAGAAGTCAGTACGCCAGTCAGTGCTGCCGGTGAAC

ACCCTGGAGGAAGTCCACGAGGAGAAGTGTTACCCACCTAAGCTGGATGAAGCAAA

GGAGCAACTATTACTTAAGAAACTCCAGGAGAGTGCATCCATGGCCAACAGAAGCA

GGTATCAGTCGCGCAAAGTAGAAAACATGAAAGCAGCAATCATCCAGAGACTAAAG
```

-continued

```
AGAGGCTGTAGACTATACTTAATGTCAGAGACCCCAAAAGTCCCTACTTACCGGACT

ACATATCCGGCGCCTGTGTACTCGCCTCCGATCAACGTCCGATTGTCCAATCCCGAG

TCCGCAGTGGCAGCATGCAATGAGTTCTTAGCTAGAAACTATCCAACTGTCTCATCA

TACCAAATTACCGACGAGTATGATGCATATCTAGACATGGTGGACGGGTCGGAGAG

TTGCCTGGACCGAGCGACATTCAATCCGTCAAAACTCAGGAGCTACCCGAAACAGC

ACGCTTACCACGCGCCCTCCATCAGAAGCGCTGTACCGTCCCCATTCCAGAACACAC

TACAGAATGTACTGGCAGCAGCCACGAAAAGAAACTGCAACGTCACACAGATGAGG

GAATTACCCACTTTGGACTCAGCAGTATTCAACGTGGAGTGTTTCAAAAAATTCGCA

TGCAACCAAGAATACTGGGAAGAATTTGCTGCCAGCCCTATTAGGATAACAACTGA

GAATTTAGCAACCTATGTTACTAAACTAAAAGGGCCAAAAGCAGCAGCGCTATTCG

CAAAAACCCATAATCTACTGCCACTACAGGAAGTACCAATGGATAGGTTCACAGTA

GATATGAAAAGGGACGTAAAGGTGACTCCTGGTACAAAGCATACAGAGGAAAGAC

CTAAGGTGCAGGTTATACAGGCGGCTGAACCCTTGGCGACAGCATACCTATGTGGG

ATTCACAGAGAGCTGGTTAGGAGGCTGAACGCCGTCCTCCTACCCAATGTACATACA

CTATTTGACATGTCTGCCGAGGATTTCGATGCCATCATAGCCGCACACTTTAAGCCA

GGAGACACTGTTTTGGAAACGGACATAGCCTCCTTTGATAAGAGCCAAGATGATTCA

CTTGCGCTTACTGCTTTGATGCTGTTAGAGGATTTAGGGGTGGATCACTCCCTGCTGG

ACTTGATAGAGGCTGCTTTCGGAGAGATTTCCAGCTGTCACCTACCGACAGGTACGC

GCTTCAAGTTCGGCGCCATGATGAAATCAGGTATGTTCCTAACTCTGTTCGTCAACA

CATTGTTAAACATCACCATCGCCAGCCGAGTGCTGGAAGATCGTCTGACAAAATCCG

CGTGCGCGGCCTTCATCGGCGACGACAACATAATACATGGAGTCGTCTCCGATGAAT

TGATGGCAGCCAGATGTGCCACTTGGATGAACATGGAAGTGAAGATCATAGATGCA

GTTGTATCCTTGAAAGCCCCTTACTTTTGTGGAGGGTTTATACTGCACGATACTGTGA

CAGGAACAGCTTGCAGAGTGGCAGACCCGCTAAAAAGGCTTTTTAAACTGGGCAAA

CCGCTAGCGGCAGGTGACGAACAAGATGAAGATAGAAGACGAGCGCTGGCTGACG

AAGTGATCAGATGGCAACGAACAGGGCTAATTGATGAGCTGGAGAAAGCGGTATAC

TCTAGGTACGAAGTGCAGGGTATATCAGTTGTGGTAATGTCCATGGCCACCTTTGCA

AGCTCCAGATCCAACTTCGAGAAGCTCAGAGGACCCGTCATAACTTTGTACGGCGGT

CCTAAATAGGTACGCACTACAGCTACCTATTTTGCAGAAGCCGACAGCAAGTATCTA

AACACTAATCAGCTACAATGGAGTTCATCCCAACCCAAACTTTTTACAATAGGAGGT

ACCAGCCTCGACCCTGGACTCCGCGCCCTACTATCCAAGTCATCAGGCCCAGACCGC

GCCCTCAGAGGCAAGCTGGGCAACTTGCCCAGCTGATCTCAGCAGTTAATAAACTG

ACAATGCGCGCGGTACCACAACAGAAGCCACGCAGGAATCGGAAGAATAAGAAGC

AAAAGCAAAAACAACAGGCGCCACAAAACAACACAAATCAAAAGAAGCAGCCACC

TAAAAAGAAACCGGCTCAAAAGAAAAAGAAGCCGGGCCGCAGAGAGAGGATGTGC

ATGAAAATCGAAAATGATTGTATTTTCGAAGTCAAGCACGAAGGTAAGGTAACAGG

TTACGCGTGCCTGGTGGGGGACAAAGTAATGAAACCAGCACACGTAAAGGGGACCA

TCGATAACGCGGACCTGGCCAAACTGGCCTTTAAGCGGTCATCTAAGTATGACCTTG

AATGCGCGCAGATACCCGTGCACATGAAGTCCGACGCTTCGAAGTTCACCCATGAG

AAACCGGAGGGGTACTACAACTGGCACCACGGAGCAGTACAGTACTCAGGAGGCCG
```

-continued

```
GTTCACCATCCCTACAGGTGCTGGCAAACCAGGGGACAGCGGCAGACCGATCTTCG

ACAACAAGGGACGCGTGGTGGCCATAGTCTTAGGAGGAGCTAATGAAGGAGCCCGT

ACAGCCCTCTCGGTGGTGACCTGGAATAAAGACATTGTCACTAAAATCACCCCCGA

GGGGGCCGAAGAGTGGAGTCTTGCCATCCCAGTTATGTGCCTGTTGGCAAACACCAC

GTTCCCCTGCTCCCAGCCCCCTTGCACGCCCTGCTGCTACGAAAAGGAACCGGAGGA

AACCCTACGCATGCTTGAGGACAACGTCATGAGACCTGGGTACTATCAGCTGCTACA

AGCATCCTTAACATGTTCTCCCCACCGCCAGCGACGCAGCACCAAGGACAACTTCAA

TGTCTATAAAGCCACAAGACCATACTTAGCTCACTGTCCCGACTGTGGAGAAGGGCA

CTCGTGCCATAGTCCCGTAGCACTAGAACGCATCAGAAATGAAGCGACAGACGGGA

CGCTGAAAATCCAGGTCTCCTTGCAAATCGGAATAAAGACGGATGACAGCCACGAT

TGGACCAAGCTGCGTTATATGGACAACCACATGCCAGCAGACGCAGAGAGGGCGGG

GCTATTTGTAAGAACATCAGCACCGTGTACGATTACTGGAACAATGGGACACTTCAT

CCTGGCCCGATGTCCAAAAGGGGAAACTCTGACGGTGGGATTCACTGACAGTAGGA

AGATTAGTCACTCATGTACGCACCCATTTCACCACGACCCTCCTGTGATAGGTCGGG

AAAAATTCCATTCCCGACCGCAGCACGGTAAAGAGCTACCTTGCAGCACGTACGTG

CAGAGCACCGCCGCAACTACCGAGGAGATAGAGGTACACATGCCCCCAGACACCCC

TGATCGCACATTAATGTCACAACAGTCCGGCAACGTAAAGATCACAGTCAATGGCC

AGACGGTGCGGTACAAGTGTAATTGCGGTGGCTCAAATGAAGGACTAACAACTACA

GACAAAGTGATTAATAACTGCAAGGTTGATCAATGTCATGCCGCGGTCACCAATCAC

AAAAAGTGGCAGTATAACTCCCCTCTGGTCCCGCGTAATGCTGAACTTGGGGACCGA

AAAGGAAAAATTCACATCCCGTTTCCGCTGGCAAATGTAACATGCAGGGTGCCTAA

AGCAAGGAACCCCACCGTGACGTACGGGAAAAACCAAGTCATCATGCTACTGTATC

CTGACCACCCAACACTCCTGTCCTACCGGAATATGGGAGAAGAACCAAACTATCAA

GAAGAGTGGGTGATGCATAAGAAGGAAGTCGTGCTAACCGTGCCGACTGAAGGGCT

CGAGGTCACGTGGGGCAACAACGAGCCGTATAAGTATTGGCCGCAGTTATCTACAA

ACGGTACAGCCCATGGCCACCCGCATGAGATAATTCTGTATTATTATGAGCTGTACC

CCACTATGACTGTAGTAGTTGTGTCAGTGGCCACGTTCATACTCCTGTCGATGGTGG

GTATGGCAGCGGGGATGTGCATGTGTGCACGACGCAGATGCATCACACCGTATGAA

CTGACACCAGGAGCTACCGTCCCTTTCCTGCTTAGCCTAATATGCTGCATCAGAACA

GCTAAAGCGGCCACATACCAAGAGGCTGCGATATACCTGTGGAACGAGCAGCAACC

TTTGTTTTGGCTACAAGCCCTTATTCCGCTGGCAGCCCTGATTGTTCTATGCAACTGT

CTGAGACTCTTACCATGCTGCTGTAAAACGTTGGCTTTTTTAGCCGTAATGAGCGTC

GGTGCCCACACTGTGAGCGCGTACGAACACGTAACAGTGATCCCGAACACGGTGGG

AGTACCGTATAAGACTCTAGTCAATAGACCTGGCTACAGCCCCATGGTATTGGAGAT

GGAACTACTGTCAGTCACTTTGGAGCCAACACTATCGCTTGATTACATCACGTGCGA

GTACAAAACCGTCATCCCGTCTCCGTACGTGAAGTGCTGCGGTACAGCAGAGTGCA

AGGACAAAAACCTACCTGACTACAGCTGTAAGGTCTTCACCGGCGTCTACCCATTTA

TGTGGGGCGGCGCCTACTGCTTCTGCGACGCTGAAAACACGCAGTTGAGCGAAGCA

CACGTGGAGAAGTCCGAATCATGCAAAACAGAATTTGCATCAGCATACAGGGCTCA

TACCGCATCTGCATCAGCTAAGCTCCGCGTCCTTTACCAAGGAAATAACATCACTGT

AACTGCCTATGCAAACGGCGACCATGCCGTCACAGTTAAGGACGCCAAATTCATTGT
```

GGGGCCAATGTCTTCAGCCTGGACACCTTTCGACAACAAAATTGTGGTGTACAAAGG

TGACGTCTATAACATGGACTACCCGCCCTTTGGCGCAGGAAGACCAGGACAATTTGG

CGATATCCAAAGTCGCACACCTGAGAGTAAAGACGTCTATGCTAATACACAACTGG

TACTGCAGAGACCGGCTGTGGGTACGGTACACGTGCCATACTCTCAGGCACCATCTG

GCTTTAAGTATTGGCTAAAAGAACGCGGGGCGTCGCTGCAGCACACAGCACCATTT

GGCTGCCAAATAGCAACAAACCCGGTAAGAGCGGTGAACTGCGCCGTAGGGAACAT

GCCCATCTCCATCGACATACCGGAAGCGGCCTTCACTAGGGTCGTCGACGCGCCCTC

TTTAACGGACATGTCGTGCGAGGTACCAGCCTGCACCCATTCCTCAGACTTTGGGGG

CGTCGCCATTATTAAATATGCAGCCAGCAAGAAAGGCAAGTGTGCGGTGCATTCGA

TGACTAACGCCGTCACTATTCGGGAAGCTGAGATAGAAGTTGAAGGGAATTCTCAG

CTGCAAATCTCTTTCTCGACGGCCTTAGCCAGCGCCGAATTCCGCGTACAAGTCTGT

TCTACACAAGTACACTGTGCAGCCGAGTGCCACCCCCCGAAGGACCACATAGTCAA

CTACCCGGCGTCACATACCACCCTCGGGGTCCAGGACATCTCCGCTACGGCGATGTC

ATGGGTGCAGAAGATCACGGGAGGTGTGGGACTGGTTGTTGCTGTTGCCGCACTGAT

TCTAATCGTGGTGCTATGCGTGTCGTTCAGCAGGCACTAACTTGACAATTAAGTATG

AAGGTATATGTGTCCCCTAAGAGACACACTGTACATAGCAAATAATCTATAGATCAA

AGGGCTACGCAACCCCTGAATAGTAACAAAATACAAATCACTAAAAATTATAAAA

ACAGAAAAATACATAAATAGGTATACGTGTCCCCTAAGAGACACATTGTATGTAGG

TGATAAGTATAGATCAAAGGGCCGAATAACCCCTGAATAGTAACAAAATATGAAAA

TCAATAAAAATCATAAAATAGAAAAACCATAAACAGAAGTAGTTCAAAGGGCTATA

AAACCCCTGAATAGTAACAAAACATAAAATTAATAAAAATCAAATGAATACCATAA

TTGGCAAACGGAAGAGATGTAGGTACTTAAGCTTCCTAAAAGCAGCCGAACTCACT

TTGAGAAGTAGGCATAGCATACCGAACTCTTCCACGATTCTCCGAACCCACAGGGA

CGTAGGAGATGTTATTTTGTTTTTAATATTTCAAAAAAAAAAAAAAAAAAAAAAAA

Amino acid sequence of E2 protein from LR2006_OPY1 Chikungunya
virus strain-amino acids 339-742 from structural polyprotein
GenBank Accession: ABD95938.1 (1-1248 aa)

SEQ ID NO: 2

STKDNFNVYKATRPYLAHCPDCGEGHSCHSPVALERIRNEATDGTLKIQVSLQIGIKTDD

SHDWTKLRYMDNHMPADAERAGLFVRTSAPCTITGTMGHFILARCPKGETLTVGFTDS

RKISHSCTHPFHHDPPVIGREKFHSRPQHGKELPCSTYVQSTAATTEEIEVHMPPDTPDHT

LMSQQSGNVKITVNGQTVRYKCNCGGSNEGLTTTDKVINNCKVDQCHAAVTNHKKWQ

YNSPLVPRNAELGDRKGKIHIPFPLANVTCRVPKARNPTVTYGKNQVIMLLYPDHPTLLS

YRNMGEEPNYQEEWVMHKKEVVLTVPTEGLEVTWGNNEPYKYWPQLSTNGTAHGHP

HEIILYYYELYPTMTVVVVSVATFILLSMVGMAAGMCMCARRRCITPYELTPGATVPFL

LSLICCIRTAKA

Some E2 variants identified herein
E168K variant of E2 protein from Chikungunya virus

SEQ ID NO: 3

STKDNFNVYKATRPYLAHCPDCGEGHSCHSPVALERIRNEATDGTLKIQVSLQIGIKTDD

SHDWTKLRYMDNHMPADAERAGLFVRTSAPCTITGTMGHFILARCPKGETLTVGFTDS

RKISHSCTHPFHHDPPVIGREKFHSRPQHGKELPCSTYVQSTAATTEEIKVHMPPDTPDH

TLMSQQSGNVKITVNGQTVRYKCNCGGSNEGLTTTDKVINNCKVDQCHAAVTNHKKW

QYNSPLVPRNAELGDRKGKIHIPFPLANVTCRVPKARNPTVTYGKNQVIMLLYPDHPTL

-continued

LSYRNMGEEPNYQEEWVMHKKEVVLTVPTEGLEVTWGNNEPYKYWPQLSTNGTAHG

HPHEIILYYYELYPTMTVVVVSVATFILLSMVGMAAGMCMCARRRCITPYELTPGATVP

FLLSLICCIRTAKA

G55R variant of E2 protein from Chikungunya virus
SEQ ID NO: 4
STKDNFNVYKATRPYLAHCPDCGEGHSCHSPVALERIRNEATDGTLKIQVSLQIRIKTDD

SHDWTKLRYMDNHMPADAERAGLFVRTSAPCTITGTMGHFILARCPKGETLTVGFTDS

RKISHSCTHPFHHDPPVIGREKFHSRPQHGKELPCSTYVQSTAATTEEIEVHMPPDTPDHT

LMSQQSGNVKITVNGQTVRYKCNCGGSNEGLTTTDKVINNCKVDQCHAAVTNHKKWQ

YNSPLVPRNAELGDRKGKIHIPFPLANVTCRVPKARNPTVTYGKNQVIMLLYPDHPTLLS

YRNMGEEPNYQEEWVMHKKEVVLTVPTEGLEVTWGNNEPYKYWPQLSTNGTAHGHP

HEIILYYYELYPTMTVVVVSVATFILLSMVGMAAGMCMCARRRCITPYELTPGATVPFL

LSLICCIRTAKA

E247K variant of E2 protein from Chikungunya virus
SEQ ID NO: 5
STKDNFNVYKATRPYLAHCPDCGEGHSCHSPVALERIRNEATDGTLKIQVSLQIGIKTDD

SHDWTKLRYMDNHMPADAERAGLFVRTSAPCTITGTMGHFILARCPKGETLTVGFTDS

RKISHSCTHPFHHDPPVIGREKFHSRPQHGKELPCSTYVQSTAATTEEIEVHMPPDTPDHT

LMSQQSGNVKITVNGQTVRYKCNCGGSNEGLTTTDKVINNCKVDQCHAAVTNHKKWQ

YNSPLVPRNAKLGDRKGKIHIPFPLANVTCRVPKARNPTVTYGKNQVIMLLYPDHPTLL

SYRNMGEEPNYQEEWVMHKKEVVLTVPTEGLEVTWGNNEPYKYWPQLSTNGTAHGH

PHEIILYYYELYPTMTVVVVSVATFILLSMVGMAAGMCMCARRRCITPYELTPGATVPF

LLSLICCIRTAKA

G82R variant of E2 protein from Chikungunya virus
SEQ ID NO: 6
STKDNFNVYKATRPYLAHCPDCGEGHSCHSPVALERIRNEATDGTLKIQVSLQIGIKTDD

SHDWTKLRYMDNHMPADAERARLFVRTSAPCTITGTMGHFILARCPKGETLTVGFTDS

RKISHSCTHPFHHDPPVIGREKFHSRPQHGKELPCSTYVQSTAATTEEIEVHMPPDTPDHT

LMSQQSGNVKITVNGQTVRYKCNCGGSNEGLTTTDKVINNCKVDQCHAAVTNHKKWQ

YNSPLVPRNAELGDRKGKIHIPFPLANVTCRVPKARNPTVTYGKNQVIMLLYPDHPTLLS

YRNMGEEPNYQEEWVMHKKEVVLTVPTEGLEVTWGNNEPYKYWPQLSTNGTAHGHP

HEIILYYYELYPTMTVVVVSVATFILLSMVGMAAGMCMCARRRCITPYELTPGATVPFL

LSLICCIRTAKA

H232Y variant of E2 protein from Chikungunya virus
SEQ ID NO: 7
STKDNFNVYKATRPYLAHCPDCGEGHSCHSPVALERIRNEATDGTLKIQVSLQIGIKTDD

SHDWTKLRYMDNHMPADAERAGLFVRTSAPCTITGTMGHFILARCPKGETLTVGFTDS

RKISHSCTHPFHHDPPVIGREKFHSRPQHGKELPCSTYVQSTAATTEEIEVHMPPDTPDHT

LMSQQSGNVKITVNGQTVRYKCNCGGSNEGLTTTDKVINNCKVDQCHAAVTNYKKWQ

YNSPLVPRNAELGDRKGKIHIPFPLANVTCRVPKARNPTVTYGKNQVIMLLYPDHPTLLS

YRNMGEEPNYQEEWVMHKKEVVLTVPTEGLEVTWGNNEPYKYWPQLSTNGTAHGHP

HEIILYYYELYPTMTVVVVSVATFILLSMVGMAAGMCMCARRRCITPYELTPGATVPFL

LSLICCIRTAKA

Primer 1F for CHIKV-Δ5nsP3 sequencing

SEQ ID NO: 8

TTAGGATCCGATGGCTGCGTGAGACAC

Primer 1R for CHIKV-Δ5nsP3 sequencing

SEQ ID NO: 9

TAACTCGAGCCGTCAGGTCTGTTGAACAT

Primer 2F for CHIKV-Δ5nsP3 sequencing

SEQ ID NO: 10

TTAGGATCCTACCACCAGGCGATTAAAG

Primer 2R for CHIKV-Δ5nsP3 sequencing

SEQ ID NO: 11

TAACTCGAGCTTTGCCCACTTACTGAAGG

Primer 3F for CHIKV-Δ5nsP3 sequencing

SEQ ID NO: 12

TTAGGATCCTGCTACAGAAGTCACGCC

Primer 3R for CHIKV-Δ5nsP3 sequencing

SEQ ID NO: 13

TAACTCGAGGCCAAAGCGTGAATCAG

Primer 4F for CHIKV-Δ5nsP3 sequencing

SEQ ID NO: 14

TTAGGATCCAACAGCTTGAGGACAGAGCG

Primer 4R for CHIKV-Δ5nsP3 sequencing

SEQ ID NO: 15

TAACTCGAGCTCTGTCTCATCACGTCGG

Primer 5F for CHIKV-Δ5nsP3 sequencing

SEQ ID NO: 16

TTAGGATCCAAATTGCAGTCATAGGAGTCTTC

Primer 5R for CHIKV-Δ5nsP3 sequencing

SEQ ID NO: 17

TAACTCGAGAGTACGTTGACGTGCTCTGA

Primer 6F for CHIKV-Δ5nsP3 sequencing

SEQ ID NO: 18

TTAGGATCCGTGGGTTAAACAACTGCAAA

Primer 6R for CHIKV-Δ5nsP3 sequencing

SEQ ID NO: 19

TAACTCGAGGGTTAAAGTCTTCTATCCTCCTGG

Primer 7F for CHIKV-Δ5nsP3 sequencing

SEQ ID NO: 20

TTAGGATCCGGATAACCACTGGGATAATAGG

Primer 7R for CHIKV-Δ5nsP3 sequencing

SEQ ID NO: 21

TAACTCGAGAGTTGTGAAATTCCTTCTGCC

Primer 8F for CHIKV-Δ5nsP3 sequencing

SEQ ID NO: 22

TTAGGATCCCGCAGATAGAACCAGTGAAC

Primer 8R for CHIKV-Δ5nsP3 sequencing

SEQ ID NO: 23

TAACTCGAGCAGCAGCTCTACTTGGGTC

Primer 9F for CHIKV-Δ5nsP3 sequencing

SEQ ID NO: 24

TTAGGATCCAGGAGGGAAAGACAGGCT

Primer 9R for CHIKV-Δ5nsP3 sequencing

SEQ ID NO: 25

TAACTCGAGCCCTCGCCTTCTTCTG

Primer 10F for CHIKV-Δ5nsP3 sequencing

SEQ ID NO: 26

TTAGGATCCCAAAATAGAAGGAGTGCAAAAAG

Primer 10R for CHIKV-Δ5nsP3 sequencing

SEQ ID NO: 27

TAACTCGAGCCTGGAGTTTCTTAAGTAATAGTTGC

-continued

Primer 11F for CHIKV-Δ5nsP3 sequencing

SEQ ID NO: 28

TTAGGATCCACCGGTCCAGGTCATTTA

Primer 11R for CHIKV-Δ5nsP3 sequencing

SEQ ID NO: 29

TAACTCGAGGCAGCAAATTCTTCCCAG

Primer 12F for CHIKV-Δ5nsP3 sequencing

SEQ ID NO: 30

TTAGGATCCCCATTCCAGAACACACTACAG

Primer 12R for CHIKV-Δ5nsP3 sequencing

SEQ ID NO: 31

TAACTCGAGATACCTGATTTCATCATGGC

Primer 13F for CHIKV-Δ5nsP3 sequencing

SEQ ID NO: 32

TTAGGATCCCCTTTGATAAGAGCCAAGATG

Primer 13R for CHIKV-Δ5nsP3 sequencing

SEQ ID NO: 33

TAACTCGAGTACAAAGTTATGACGGGTCCT

Primer 14F for CHIKV-Δ5nsP3 sequencing

SEQ ID NO: 34

TTAGGATCCCAACGAACAGGGCTAATTG

Primer 14R for CHIKV-Δ5nsP3 sequencing

SEQ ID NO: 35

TAACTCGAGGACCGCTTAAAGGCCAG

Primer 15F for CHIKV-Δ5nsP3 sequencing

SEQ ID NO: 36

TTAGGATCCGTGCATGAAAATCGAAAATG

Primer 15R for CHIKV-Δ5nsP3 sequencing

SEQ ID NO: 37

TAACTCGAGTGGTCTTGTGGCTTTATAGACA

Primer 16F for CHIKV-Δ5nsP3 sequencing

SEQ ID NO: 38

TTAGGATCCAACCGGAGGAAACCCTAC

Primer 16R for CHIKV-Δ5nsP3 sequencing

SEQ ID NO: 39

TAACTCGAGGTACCGCACCGTCTGG

Primer 17F for CHIKV-Δ5nsP3 sequencing

SEQ ID NO: 40

TTAGGATCCAGCTACCTTGCAGCACGT

Primer 17R for CHIKV-Δ5nsP3 sequencing

SEQ ID NO: 41

TAACTCGAGCCCACCATCGACAGG

Primer 18F for CHIKV-Δ5nsP3 sequencing

SEQ ID NO: 42

TTAGGATCCCGAGCCGTATAAGTATTGGC

Primer 18R for CHIKV-Δ5nsP3 sequencing

SEQ ID NO: 43

TAACTCGAGCGCCGGTGAAGACCTTAC

Primer 19F for CHIKV-Δ5nsP3 sequencing

SEQ ID NO: 44

TTAGGATCCACTACTGTCAGTCACTTTGGAGC

Primer 19R for CHIKV-Δ5nsP3 sequencing

SEQ ID NO: 45

TAACTCGAGTACCGGGTTTGTTGCTATTT

Primer 20F for CHIKV-Δ5nsP3 sequencing

SEQ ID NO: 46

TTAGGATCCCACAACTGGTACTGCAGAGAC

Primer 20R for CHIKV-Δ5nsP3 sequencing

SEQ ID NO: 47

TAACTCGAGGCGTAGCCCTTTGATCTATAG

-continued

Primer 21F for CHIKV-Δ5nsP3 sequencing
                                                            SEQ ID NO: 48

TTAGGATCCGGTGCTATGCGTGTCGT

Primer 21R for CHIKV-Δ5nsP3 sequencing
                                                            SEQ ID NO: 49

TAACTCGAGATCTCCTACGTCCCTGTGGG

The invention claimed is:

1. A pharmaceutical composition comprising chikungu-nya virus (CHIKV)-Δ5nsP3 particles, wherein said pharmaceutical composition comprises:

(i) at least $10^3$ CHIKV-Δ5nsP3 particles which express an E2 structural protein as defined by the amino acid sequence of SEQ ID NO: 2; and (ii) 1-70% CHIKV-Δ5nsP3 particles which express an E2 structural protein having at least one mutation compared with the amino acid sequence of SEQ ID NO: 2, wherein said at least one mutation is selected from the group consisting of E168K, E247K, H99Y, G55R, H232Y and T230I.

2. The pharmaceutical composition according to claim 1, wherein the CHIKV-Δ5nsP3 particles of (ii) express an E2 structural protein having no more than three mutations compared with the amino acid sequence of SEQ ID NO: 2.

3. The pharmaceutical composition according to claim 1, wherein the CHIKV-Δ5nsP3 particles of (ii) express an E2 structural protein having no more than two mutations compared with the amino acid sequence of SEQ ID NO: 2.

4. The pharmaceutical composition according to claim 1, wherein the CHIKV-Δ5nsP3 particles of (ii) express an E2 structural protein having no more than one mutation compared with the amino acid sequence of SEQ ID NO: 2.

5. The pharmaceutical composition according to claim 1, wherein the pharmaceutical composition comprises up to $3 \times 10^4$ CHIKV-Δ5nsP3 particles which express the E2 structural protein as defined by the amino acid sequence of SEQ ID NO: 2.

6. The pharmaceutical composition according to claim 1, wherein the pharmaceutical composition comprises up to $10^5$ CHIKV-Δ5nsP3 particles which express the E2 structural protein as defined by the amino acid sequence of SEQ ID NO: 2.

7. The pharmaceutical composition according to claim 1, wherein the pharmaceutical composition comprises 1-50% of CHIKV-Δ5nsP3 particles which express an E2 structural protein having at least one mutation compared with the amino acid sequence of SEQ ID NO: 2.

8. The pharmaceutical composition according to claim 1, wherein said CHIKV-Δ5nsP3 particles of (i) comprise an RNA genome corresponding to the DNA sequence of SEQ ID NO: 1.

9. The pharmaceutical composition according to claim 1, wherein said pharmaceutical composition induces neutralizing antibodies against CHIKV-Δ5nsP3 in a mouse immunized with said pharmaceutical composition resulting in a mouse serum comprising said neutralizing antibodies, and wherein said mouse serum neutralizes CHIKV infection of Vero cells by at least 80% in an in vitro plaque reduction neutralization assay at a 1:80 serum dilution.

10. The pharmaceutical composition according to claim 1, wherein said pharmaceutical composition induces neutralizing antibodies against CHIKV-Δ5nsP3 in a mouse immunized with said pharmaceutical composition resulting in a mouse serum comprising said neutralizing antibodies, and wherein said mouse serum neutralizes CHIKV infection of Vero cells by at least 90% in an in vitro plaque reduction neutralization assay at a 1:80 serum dilution.

11. The pharmaceutical composition according to claim 1, wherein said pharmaceutical composition induces neutralizing antibodies against CHIKV-Δ5nsP3 in a mouse immunized with said pharmaceutical composition, resulting in a mouse serum comprising said neutralizing antibodies, and wherein said mouse serum neutralizes CHIKV infection of Vero cells by at least 95% in an in vitro plaque reduction neutralization assay at a 1:80 serum dilution.

12. The pharmaceutical composition according to claim 1, which is obtained by production of CHIKV-Δ5nsP3 particles on Vero cells, wherein said production comprises passaging CHIKV-Δ5nsP3 particles comprising an RNA genome corresponding to the DNA sequence of SEQ ID NO: 1 on Vero cells in culture fewer than five times.

13. The pharmaceutical composition according to claim 12, wherein said CHIKV-Δ5nsP3 particles are passaged on Vero cells in culture at most three times.

14. The pharmaceutical composition according to claim 1, wherein said pharmaceutical composition is a one-shot pharmaceutical composition.

15. The pharmaceutical composition according to claim 1, wherein said pharmaceutical composition is a vaccine.

16. The pharmaceutical composition according to claim 1, wherein said pharmaceutical composition is provided in a lyophilized form.

17. The pharmaceutical composition according to claim 1, wherein said pharmaceutical composition is formulated for subcutaneous administration.

18. The pharmaceutical composition of claim 1, wherein said pharmaceutical composition comprises a pharmaceutically acceptable excipient.

19. A method of protection against disease caused by CHIKV in a subject in need thereof, comprising administering to the subject an effective amount of the pharmaceutical composition according to claim 1.

20. The method according to claim 19, wherein the subject is a human subject.

\* \* \* \* \*

SEQUENCE LISTING

Sequence total quantity: 49
SEQ ID NO: 1                   moltype = DNA   length = 11674
FEATURE                        Location/Qualifiers
source                         1..11674
                               mol_type = genomic DNA
                               organism = Chikungunya virus
SEQUENCE: 1
gatggctgcg tgagacacac gtagcctacc agtttcttac tgctctactc tgcaaagcaa  60
gagattaata acccatcatg gatcctgtgt acgtggacat agacgctgac agcgcctttt  120
tgaaggccct gcaacgtgcg taccccatgt ttgaggtgga accaaggcag gtcacaccga  180
atgaccatgc taatgctaga gcgttctcgc atctagctat aaaactaata gagcaggaaa  240
ttgaccccga ctcaaccatc ctggatatcg gcagtgcgcc agcaaggagg atgatgtcgg  300
acaggaagta ccactgcgtc tgcccgatgc gcagtgcgga agatcccgag agactcgcca  360
attatgcgag aaagctagca tctgccgcag gaaaagtcct ggacagaaac atctctggaa  420
agatcgggga cttacaagca gtaatggccg tgccagacac ggagacgcca acattctgct  480
tacacacaga cgtctcatgt agacagagag cagacgtcgc tatataccaa gacgtctatg  540
ctgtacacgc acccacgtcg ctataccacc aggcgattaa aggggtccga gtggcgtact  600
gggttgggtt cgacacaacc ccgttcatgt acaatgccat ggcgggtgcc tacccctcat  660
actcgacaaa ctgggcagat gagcaggtac tgaaggctaa gaacatagga ttatgttcaa  720
cagacctgac ggaaggtaga cgaggcaagt tgtctattat gagagggaaa aagctaaaac  780
cgtgcgaccg tgtgctgttc tcagtagggt caacgctcta cccggaaagc cgcaagctac  840
ttaagagctg gcacctgcca tcggtgttcc atttaaaggg caaactcagc ttcacatgcc  900
gctgtgatac agtggtttcg tgtgagggct acgtcgttaa gagaataacg atgagcccag  960
gccttatgg aaaaaccaca gggtatgcgg taacccacca cgcagacgga ttcctgatgt  1020
gcaagactac cgacacggtt gacggcgaaa gaatgtcatt ctcggtgtgc acatacgtgc  1080
cggcgaccat ttgtgatcaa atgaccggca tccttgctac agaagtcacg ccggaggatg  1140
cacagaagct gttggtgggg ctgaaccaga gaatagtggt taacggcaga acgcaacgga  1200
atacgaacac catgaaaaat tatctgcttc ccgtggtcgc ccaagccttc agtaagtggg  1260
caaaggagtg ccggaaagac atggaagatg aaaaactcct gggggtcaga gaaagaaaca  1320
tgacctgctg ctgtctcatgg gcattcaaga agcagaaaac acacacggtc tacaagaggc  1380
ctgatacccca gtcaattcag aaggttcagg ccgagtttga cagcttttgtg gtaccgagtc  1440
tgtggtcgtc cgggttgtca atccctttga ggactagaat caaatggttg ttaagcaagg  1500
tgccaaaaac cgacctgatc ccatacagcg gagacgcccg agaagcccgg gacgcagaaa  1560
aagaagcaga ggaagaacga gaagcagaac tgactcgcga agccctacca cctctacagg  1620
cagcacagga agatgttcag gtcgaaatcg acgtggaaca gcttgaggac agagcgggcg  1680
caggaataat agagactccg agaggagcta tcaaagttac tgcccaacca acagaccacg  1740
tcgtgggaga gtacctggta ctctcccccg agaccgtact acgtagccag aagctcagtc  1800
tgattcacgc tttggcggag caagtgaaga cgtgcacgca caacggacga gcagggaggt  1860
atgcggtcga agcgtacgac ggccgagtcc tagtgccctc aggctatgca atctcgcctg  1920
aagacttcca gagtctaagc gaaagcgcaa cgatggtgta taacgaaaga gagttcgtaa  1980
acagaaagct cacaccatatt gcgatgcacg gaccagccgt gaacaccgac gaagagtcgt  2040
atgagctggt gagggcagag aggacagaac acgagtacgt ctacgacgtg gatcagagaa  2100
gatgctgtaa gaaggaagaa gccgcaggac tggtactggt gggcgacttg actaatccgc  2160
cctaccacga attcgcatat gaagggctaa aaatccgccc tgcctgccca tacaaaattg  2220
cagtcatagg agtcttcgga gtaccgggat ctggcaagtc agctattatc aagaacctag  2280
ttaccaggca ggacctggtg actagcggaa agaaagaaaa ctgccaagaa atcaccaccg  2340
acgtgatgag acagagaggt ctagagatat ctgcacgtac ggttgactcg ctgctcttga  2400
atgggtgcaa cagaccagtc gacgtgttgt acgtagacga ggcgtttgcg tgccactctg  2460
gaacgctact tgctttgatc gccttggtga gaccaaggca gaaagttgta ctttgtggtg  2520
acccaagca gtgcggcttc ttcaatatga tgcagatgaa agtcaactat aatcacaaca  2580
tctgcaccca gtgtaccac aaaagtatct ccaggcggtg tacactgcct gtgaccgcca  2640
ttgtgtcatc gttgcattac gaaggcaaaa tgcgcactac gaatgagtac aacaagccga  2700
ttgtagtgga cactacaggc tcaacaaaac ctgaccctgg atacctcgtg ttaacgtgct  2760
tcagagggtg ggtaaacaa ctgcaaattg actatcgtgg atacgaggtc atgacagcag  2820
ccgcatccca agggttaacc agaaaaggag tttacgcagt tagacaaaaa gttaatgaaa  2880
accgctctca tgcatcaacg tcagagcacg tcaacgtact cctaacgcgt acggaaggta  2940
aactggtatg gaagacactt ccggcgacc cgtggataaa gacgtgcag aacccaccga  3000
aaggaaactt caaagcaact attaaggagt gggaggtgga gcatgcatca ataatgcggg  3060
gcatctgcag tcaccaaatg accttcgata cattccaaaa taaagccaac gtttgttggg  3120
ctaagagctt ggtccctatc ctcgaaacag cggggataaa actaaatgat aggcagtggt  3180
ctcagataat tcaagccttc aaagaagaca aagcatactc acctgaagta gccctgaatg  3240
aaatatgtac gcgcatgtat gggtggatc tagacagcgg gctatttttct aaccgttgg  3300
tgtctgtgta ttacgcggat aaccactggg ataataggcc tggagggaaa atgttcggat  3360
ttaacccga ggcagcatcc attctagaaa gaaagtatcc attcacaaaa gggagtggga  3420
acatcaacaa gcagatctgc gtgactacca ggaggataga agactttaac cctaccacca  3480
acatcatacc ggccaacagg agactaccac actcattagt ggccgaacac cgcccagtaa  3540

```
aagggggaaag aatggaatgg ctggttaaca agataaacgg ccaccacgtg ctcctggtca   3600
gtggctataa ccttgcactg cctactaaga gagtcacttg ggtagcgccg ttaggtgtcc   3660
gcggagcgga ctacacatac aacctagagt tgggtctgcc agcaacgctt ggtaggtatg   3720
acctagtggt cataaacatc cacacacctt ttcgcataca ccattaccaa cagtgcgtcg   3780
accacgcaat gaaactgcaa atgctcgggg gtgactcatt gagactgctc aaaccgggcg   3840
gctctctatt gatcagagca tatggttacg cagatagaac cagtgaacga gtcatctgcg   3900
tattgggacg caagtttaga tcgtctagag cgttgaaacc accatgtgtc accagcaaca   3960
ctgagatgtt tttcctattc agcaactttg acaatggcag aaggaatttc acaactcatg   4020
tcatgaacaa tcaactgaat gcagccttcg taggacaggt cacccgagca ggatgtgcac   4080
cgtcgtaccg ggtaaaacgc atggacatcg cgaagaacga tgaagagtgc gtagtcaacg   4140
ccgctaaccc tcgcgggtta ccgggtggcg gtgtttgcaa ggcagtatac aaaaaatggc   4200
cggagtcctt taagaacagt gcaacaccag tgggaaccgc aaaaacagtt atgtgcggta   4260
cgtatccagt aatccacgct gttggaccaa acttctctaa ttattcggag tctgaaggggg  4320
accgggaatt ggcagctgcc tatcgagaag tcgcaaagga agtaactagg ctgggagtaa   4380
atagtgtagc tatacctctc ctctccacag gtgtatactc aggagggaaa gacaggctga   4440
cccagtcact gaaccacctc tttacagcca tggactcgac ggatgcagac gtggtcatct   4500
actgccgcga caaagaatgg gagaagaaaa tatctgaggc catacagatg cggacccaag   4560
tagagctgct ggatgagcac atctccatag actgcgatat tgttcgcgtg caccctgaca   4620
gcagcttggc aggcagaaaa ggatacagca ccacggaagg cgcactgtac tcatatctag   4680
aagggacccg ttttcatcag acggctgtgg atatggcgga gatacatact atgtggccaa   4740
agcaaacaga ggccaatgag caagtctgcc tatatgccct gggggaaagt attgaatcga   4800
tcaggcagaa atgcccggtg gatgatgcag acgcatcatc tccccccaaa actgtcccgt   4860
gcctttgccg ttacgctatg actccagaac gcgtcacccg gcttcgcatg aaccacgtca   4920
caagcataat tgtgtgttct tcgtttcccc tcccaaagta caaaatagaa ggagtgcaaa   4980
aagtcaaatg ctctaaggta atgctatttg accacaacgt gccatcgcgc gtaagtccaa   5040
gggcttatag aggtgccgct gccggtaacc ttgcggccgt gtctgattgg gtaatgagca   5100
ccgtacctgt cgcgccgccc agaagaaggc gagggagaaa cctgactgtg acatgtgacg   5160
agagagaagg gaatataaca cccatggcta gcgtccgatt ctttagggca gagctgtgtc   5220
cggtcgtaca agaaacagcg gagacgcgtg acacagcaat gtctcttcag gcaccaccga   5280
gtaccgccac ggaaccgaat catccgccga tctccttcgg agcatcaagc gagacgttcc   5340
ccattacatt tggggacttc aacgaaggag aaatcgaaag cttgtcttct gagctactaa   5400
ctttcggaga cttcttacca ggagaagtgg atgacttgac agacagcgac tggtccacgt   5460
gctcagacac ggacgacgag ttaagactag acagggcagg tgggtatata ttctcgtcgg   5520
acaccggtcc aggtcattta caacagaagt cagtacgcca gtcatgctg ccggtgaaca   5580
ccctggagga agtccacgag gagaagtgtt acccacctaa gctggatgaa gcaaaggagc   5640
aactattact taagaaactc caggagagtg catccatggc caacagaagc aggtatcagt   5700
cgcgcaaagt agaaaacatg aaagcagcaa tcatccagag actaaagaga ggctgtagac   5760
tatacttaat gtcagagacc ccaaaagtcc ctacttaccg gactacatat ccggcgcctg   5820
tgtactcgcc tccgatcaac gtccgattgt ccaatcccga gtccgcagtg gcagcatgca   5880
atgagttctt agctagaaac tatccaactg tctcatcata ccaaattacc gacgagtatg   5940
atgcatatct agacatggtg gacgggtcgg agagttgcct ggaccgagcg acattcaatc   6000
cgtcaaaact caggagctac ccgaaacagc acgcttacca cgcgccctcc atcagaagcg   6060
ctgtaccgtc cccattccag aacacactac agaatgtact ggcagcacca acgaaaagaa   6120
actcaacgt cacacagatg agggaattac ccactttgga ctcagcagta ttcaacgtgg   6180
agtgtttcaa aaaattcgca tgcaaccaag aatactggga agaatttgct gccagcccta   6240
ttaggataac aactgagaat ttagcaacct atgttactaa actaaaaggg ccaaaagcag   6300
cagcgctatt cgcaaaaacc cataatctac tgccactaca ggaagtacca atggataggt   6360
tcacagtaga tatgaaaagg gacgtaaagg tgactcctgg tacaaagcat acagaggaaa   6420
gacctaaggt gcaggttata caggcggctg aaccccttggc gacagcatac ctatgtggga   6480
ttcacagaga gctggttagg aggctgaacg ccgtcctcct acccaatgta catacactat   6540
ttgacatgtc tgccgaggat ttcgatgcca tcatagccgc acactttaag ccaggagaca   6600
ctgtttttgga aacggacata gcctcctttg ataagagcca agatgattca cttgcgctta   6660
ctgctttgat gctgttagag gatttagggg tggatcactc cctgctggac ttgatagagg   6720
ctgctttcgg agagatttcc agctgtcacc taccgacagg tacgcgcttc aagttcggcg   6780
ccatgatgaa atcaggtatg ttcctaactc tgttcgtcaa cacattgtta aacatcacca   6840
tcgccagccg agtgctggaa gatcgtctga caaaatccgc gtgcgcggcc ttcatcggcg   6900
acgacaacat aatacatgga gtcgtctccg atgaattgat ggcagccaga tgtgccactt   6960
ggatgaacat ggaagtgaag atcatagatg cagttgtatc cttgaaagcc ccttactttt   7020
gtggagggtt tatactgcac gatactgtga caggaacagc ttgcagagtg gcagaccccc   7080
taaaaaggct ttttaaactg ggcaaaccgc tagcggcagg tgacgaacaa gatgaagata   7140
gaagacgagc gctggctgac gaagtgatca gatggcaacg aacagggcta attgatgagc   7200
tggagaaagc ggtatactct aggtacgaag tgcagggtat atcagttgtg gtaatgtcca   7260
tggccaccctt tgcaagctcc agatccaact tcgagaagct cagaggaccc gtcataactt   7320
tgtacgggcgg tcctaaatag gtacgcacta cagctaccta ttttgcagaa gccgacagca   7380
agtatctaaa cactaatcag ctacaatgga gttcatccca acccaaactt tttacaataag   7440
gaggtaccag cctcgaccct ggactccgcg ccctactatc caagtcatca ggcccagacc   7500
gcgccctcag aggcaagctg ggcaacttgc ccagctgatc tcagcagtta ataaactgac   7560
aatgcgcgcg gtaccacaac agaagcacg caggaatcgg aagaataaga agcaaaagca   7620
aaaacaacag cgcgcacaaa acaacacaaa tcaaaagaag cagccaccta aaaagaaacc   7680
ggctcaaaag aaaaagaagc cgggccgcag agagaggatg tgcatgaaaa tcgaaaatga   7740
ttgtatttc gaagtcaagc acgaaggtaa ggtaacaggt tacgcgtgcc tggtggggga   7800
caaagtaatg aaaccagcac acgtaaaggg gaccatcgat aacgcggacc tggccaaact   7860
ggcctttaag cggtcatcta gtatgacct tgaatgcgcg cagatacccg tgcacatgaa   7920
gtccgacgct tcgaagttca cccatgagaa accggagggt tactacaact ggcaccacgg   7980
agcagtacag tactcaggag gccggttcac catccctaca ggtgctggca accaggggga   8040
cagcggcaga ccgatcttcg acaacaaggg acgcgtggtg gccatagtct taggaggagc   8100
taatgaagga gcccgtacag ccctctcggt ggtgacctgg aataaagaca ttgtcactaa   8160
aatcacccc gagggggccg aagagtggag tcttgccatc ccagttatgt gcctgttggc   8220
aaacaccacg ttcccctgct cccagcccccc ttgcacgccc tgctgctacg aaaaggaacc   8280
```

-continued

```
ggaggaaacc ctacgcatgc ttgaggacaa cgtcatgaga cctgggtact atcagctgct   8340
acaagcatcc ttaacatgtt ctccccaccg ccagcgacgc agcaccaagg acaacttcaa   8400
tgtctataaa gccacaagac catacttagc tcactgtccc gactgtggag aagggcactc   8460
gtgccatagt cccgtagcac tagaacgcat cagaaatgaa gcgacagacg ggacgctgaa   8520
aatccaggtc tccttgcaaa tcggaataaa gacggatgaa gccacgatt ggaccaagct   8580
gcgttatatg gacaaccaca tgccagcaga cgcagagagg gcggggctat ttgtaagaac   8640
atcagcaccg tgtacgatta ctggaacaat gggacacttc atcctggccc gatgtccaaa   8700
aggggaaact ctgacggtgg gattcactga cagtaggaag attagtcact catgtacgca   8760
cccatttcac cacgaccctc ctgtgatagg tcgggaaaaa ttccattccc gaccgcagca   8820
cggtaaagag ctaccttgca gcacgtacgt gcagagcacc gccgcaacta ccgaggagat   8880
agaggtacac atgcccccag acacccctga tcgcacatta atgtcacaac agtccggcaa   8940
cgtaaagatc acagtcaatg gccagacggt gcggtacaag tgtaattgcg gtggctcaaa   9000
tgaaggacta acaactacag acaaagtgat taataactgc aaggttgatc aatgtcatgc   9060
cgcggtcacc aatcacaaaa agtggcagta taactcccct ctggtcccgc gtaatgctga   9120
acttggggac cgaaaaggaa aaattcacat cccgtttccg ctggcaaatg taacatgcag   9180
ggtgcctaaa gcaaggaacc ccaccgtgac gtacgggaaa aaccaagtca tcatgctact   9240
gtatcctgac cacccaacac tcctgtccta ccggaatatg ggagaagaac caaactatca   9300
agaagagtgg gtgatgcata agaaggaagt cgtgctaacc gtgccgactg aagggctcga   9360
ggtcacgtgg ggcaacaacg agccgtataa gtattggccg cagttatcta caaacgtac   9420
agcccatggc cacccgcatg agataattct gtattattat gagctgtacc ccactatgac   9480
tgtagtagtt gtgtcagtgg ccacgttcat actcctgtcg atggtgggta tggcagcggg   9540
gatgtgcatg tgtgcacgac gcagatgcat cacaccgtat gaactgacac caggagctac   9600
cgtccctttc ctgcttagcc taatatgctg catcagaaca gctaaagcgg ccacatacca   9660
agaggctgcg atatacctgt ggaacgagca gcaacctttg tttggctac aagcccttat   9720
tccgctggca gccctgattg ttctatgcaa ctgtctgaga ctcttaccat gctgctgaa   9780
aacgttggct tttttagccg taatgagcgt cggtgcccac gtgatgagcg cgtacgaaca   9840
cgtaacagtg atcccgaaca cggtgggagt accgtataag actctagtca atagacctgg   9900
ctacagcccc atggtattgg agatggaact actgtcagtc actttggagc caacactatc   9960
gcttgattac atcacgtgcg agtacaaaac cgtcatcccg tctccgtacg tgaagtgctg   10020
cggtacagca gagtgcaagg acaaaaacct acctgactac agctgtaagg tcttcaccgg   10080
cgtctaccca tttatgtggg gcggcgccta ctgcttctgc gacgctgaaa acacgcagtt   10140
gagcgaagca cacgtggaga agtccgaatc atgcaaaaca gaatttgcat cagcatacag   10200
ggctcatacc gcatctgcat cagctaagct ccgcgtcctt taccaggaa ataacatcac   10260
tgtaactgcc tatgcaaacg gcgaccatgc cgtcacagt aaggacgcca aattcattgt   10320
ggggccaatg tcttcagcct ggacaccttt cgacaacaaa attgtggtgt acaaaggtga   10380
cgtctataac atggactacc cgcccttggg cgcaggaaga ccaggacaat ttggcgatat   10440
ccaaagtcgc acacctgaga gtaaagacgt ctatgctaat acacaactgg tactgcagag   10500
accggctgtg ggtacggtac acgtgccata ctctcaggca ccatctggct ttaagtattg   10560
gctaaaagaa cgcggggcgt cgctgcagca cacagcacca tttggctgcc aaatagcaac   10620
aaacccggta agagcggtga actgcgccgt agggaacatg cccatctcca tcgacatacc   10680
ggaagcggcc ttcactaggg tcgtcgacgc gccctcttta acgacatgt cgtgcgaggt   10740
accagcctgc acccattcct cagactttgg gggcgtcgcc attattaaat atgcagccag   10800
caagaaaggc aagtgtgcgg tgcattcgat gactaacgcc gtcactattc gggaagctga   10860
gatagaagtt gaagggaatt ctcagctgca aatctctttc tcgacggcct tagccagcgc   10920
cgaattccgc gtacaagtct gttctacaca agtacactgt gcagccgagt gccaccccc   10980
gaaggaccac atagtcaact acccggcgtc acataccacc ctcggggtcc aggacatctc   11040
cgctacggcg atgtcatggg tgcagaagat cacgggaggt gactggttgt tgttgctgt   11100
tgccgcactg attctaatcg tggtgctatg cgtgtcgttc agcaggcact aacttgacaa   11160
ttaagtatga aggtatatgt gtcccctaag agacacactg tacatagcaa ataatctata   11220
gatcaaaggg ctacgcaacc cctgaatagt aacaaaatac aaaatcacta aaaattataa   11280
aaacagaaaa atacataaat aggtatacgt gtcccctaag agacacattg tatgtaggtg   11340
ataagtatag atcaaagggc cgaataaccc ctgaatagta acaaaatatg aaaatcaata   11400
aaaatcataa aatagaaaaa ccataaacag aagtagttca aagggctata aaaccccctga   11460
atagtaacaa aacataaat taataaaat caaatgaata ccataattgg caaacggaag   11520
agatgtaggt acttaagctt cctaaaagca gccgaactca ctttgagaag taggcatagc   11580
ataccgaact cttccacgat tctccgaacc cacagggacg taggagatgt tattttgttt   11640
ttaatatttc aaaaaaaaaa aaaaaaaaaa aaaa                               11674
```

```
SEQ ID NO: 2              moltype = AA  length = 423
FEATURE                   Location/Qualifiers
source                    1..423
                          mol_type = protein
                          organism = Chikungunya virus
SEQUENCE: 2
STKDNFNVYK ATRPYLAHCP DCGEGHSCHS PVALERIRNE ATDGTLKIQV SLQIGIKTDD   60
SHDWTKLRYM DNHMPADAER AGLFVRTSAP CTITGTMGHF ILARCPKGET LTVGFTDSRK   120
ISHSCTHPFH HDPPVIGREK FHSRPQHGKE LPCSTYVQST AATTEEIEVH MPPDTPDHTL   180
MSQQSGNVKI TVNGQTVRYK CNCGGSNEGL TTTDKVINNC KVDQCHAAVT NHKKWQYNSP   240
LVPRNAELGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                 423
```

```
SEQ ID NO: 3              moltype = AA  length = 423
FEATURE                   Location/Qualifiers
REGION                    1..423
                          note = mutation arising from Vero passaging
source                    1..423
                          mol_type = protein
```

```
                              organism = synthetic construct
SEQUENCE: 3
STKDNFNVYK ATRPYLAHCP DCGEGHSCHS PVALERIRNE ATDGTLKIQV SLQIGIKTDD   60
SHDWTKLRYM DNHMPADAER AGLFVRTSAP CTITGTMGHF ILARCPKGET LTVGFTDSRK   120
ISHSCTHPFH HDPPVIGREK FHSRPQHGKE LPCSTYVQST AATTEEIKVH MPPDTPDHTL   180
MSQQSGNVKI TVNGQTVRYK CNCGGSNEGL TTTDKVINNC KVDQCHAAVT NHKKWQYNSP   240
LVPRNAELGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                423

SEQ ID NO: 4            moltype = AA  length = 423
FEATURE                 Location/Qualifiers
REGION                  1..423
                        note = mutation arising from Vero passaging
source                  1..423
                        mol_type = protein
                        organism = synthetic construct
SEQUENCE: 4
STKDNFNVYK ATRPYLAHCP DCGEGHSCHS PVALERIRNE ATDGTLKIQV SLQIRIKTDD   60
SHDWTKLRYM DNHMPADAER AGLFVRTSAP CTITGTMGHF ILARCPKGET LTVGFTDSRK   120
ISHSCTHPFH HDPPVIGREK FHSRPQHGKE LPCSTYVQST AATTEEIEVH MPPDTPDHTL   180
MSQQSGNVKI TVNGQTVRYK CNCGGSNEGL TTTDKVINNC KVDQCHAAVT NHKKWQYNSP   240
LVPRNAELGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                423

SEQ ID NO: 5            moltype = AA  length = 423
FEATURE                 Location/Qualifiers
REGION                  1..423
                        note = mutation arising from Vero passaging
source                  1..423
                        mol_type = protein
                        organism = synthetic construct
SEQUENCE: 5
STKDNFNVYK ATRPYLAHCP DCGEGHSCHS PVALERIRNE ATDGTLKIQV SLQIGIKTDD   60
SHDWTKLRYM DNHMPADAER AGLFVRTSAP CTITGTMGHF ILARCPKGET LTVGFTDSRK   120
ISHSCTHPFH HDPPVIGREK FHSRPQHGKE LPCSTYVQST AATTEEIEVH MPPDTPDHTL   180
MSQQSGNVKI TVNGQTVRYK CNCGGSNEGL TTTDKVINNC KVDQCHAAVT NHKKWQYNSP   240
LVPRNAKLGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                423

SEQ ID NO: 6            moltype = AA  length = 423
FEATURE                 Location/Qualifiers
REGION                  1..423
                        note = mutation arising from Vero passaging
source                  1..423
                        mol_type = protein
                        organism = synthetic construct
SEQUENCE: 6
STKDNFNVYK ATRPYLAHCP DCGEGHSCHS PVALERIRNE ATDGTLKIQV SLQIGIKTDD   60
SHDWTKLRYM DNHMPADAER ARLFVRTSAP CTITGTMGHF ILARCPKGET LTVGFTDSRK   120
ISHSCTHPFH HDPPVIGREK FHSRPQHGKE LPCSTYVQST AATTEEIEVH MPPDTPDHTL   180
MSQQSGNVKI TVNGQTVRYK CNCGGSNEGL TTTDKVINNC KVDQCHAAVT NHKKWQYNSP   240
LVPRNAELGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                423

SEQ ID NO: 7            moltype = AA  length = 423
FEATURE                 Location/Qualifiers
REGION                  1..423
                        note = mutation arising from Vero passaging
source                  1..423
                        mol_type = protein
                        organism = synthetic construct
SEQUENCE: 7
STKDNFNVYK ATRPYLAHCP DCGEGHSCHS PVALERIRNE ATDGTLKIQV SLQIGIKTDD   60
SHDWTKLRYM DNHMPADAER AGLFVRTSAP CTITGTMGHF ILARCPKGET LTVGFTDSRK   120
ISHSCTHPFH HDPPVIGREK FHSRPQHGKE LPCSTYVQST AATTEEIEVH MPPDTPDHTL   180
MSQQSGNVKI TVNGQTVRYK CNCGGSNEGL TTTDKVINNC KVDQCHAAVT NYKKWQYNSP   240
LVPRNAELGD RKGKIHIPFP LANVTCRVPK ARNPTVTYGK NQVIMLLYPD HPTLLSYRNM   300
GEEPNYQEEW VMHKKEVVLT VPTEGLEVTW GNNEPYKYWP QLSTNGTAHG HPHEIILYYY   360
ELYPTMTVVV VSVATFILLS MVGMAAGMCM CARRRCITPY ELTPGATVPF LLSLICCIRT   420
AKA                                                                423
```

```
SEQ ID NO: 8          moltype = DNA   length = 27
FEATURE               Location/Qualifiers
misc_feature          1..27
                      note = primer
source                1..27
                      mol_type = other DNA
                      organism = synthetic construct
SEQUENCE: 8
ttaggatccg atggctgcgt gagacac                                          27

SEQ ID NO: 9          moltype = DNA   length = 29
FEATURE               Location/Qualifiers
misc_feature          1..29
                      note = primer
source                1..29
                      mol_type = other DNA
                      organism = synthetic construct
SEQUENCE: 9
taactcgagc cgtcaggtct gttgaacat                                        29

SEQ ID NO: 10         moltype = DNA   length = 28
FEATURE               Location/Qualifiers
misc_feature          1..28
                      note = primer
source                1..28
                      mol_type = other DNA
                      organism = synthetic construct
SEQUENCE: 10
ttaggatcct accaccaggc gattaaag                                         28

SEQ ID NO: 11         moltype = DNA   length = 29
FEATURE               Location/Qualifiers
misc_feature          1..29
                      note = primer
source                1..29
                      mol_type = other DNA
                      organism = synthetic construct
SEQUENCE: 11
taactcgagc tttgcccact tactgaagg                                        29

SEQ ID NO: 12         moltype = DNA   length = 27
FEATURE               Location/Qualifiers
misc_feature          1..27
                      note = primer
source                1..27
                      mol_type = other DNA
                      organism = synthetic construct
SEQUENCE: 12
ttaggatcct gctacagaag tcacgcc                                          27

SEQ ID NO: 13         moltype = DNA   length = 26
FEATURE               Location/Qualifiers
misc_feature          1..26
                      note = primer
source                1..26
                      mol_type = other DNA
                      organism = synthetic construct
SEQUENCE: 13
taactcgagg ccaaagcgtg aatcag                                           26

SEQ ID NO: 14         moltype = DNA   length = 29
FEATURE               Location/Qualifiers
misc_feature          1..29
                      note = primer
source                1..29
                      mol_type = other DNA
                      organism = synthetic construct
SEQUENCE: 14
ttaggatcca acagcttgag gacagagcg                                        29

SEQ ID NO: 15         moltype = DNA   length = 28
FEATURE               Location/Qualifiers
misc_feature          1..28
                      note = primer
source                1..28
                      mol_type = other DNA
                      organism = synthetic construct
SEQUENCE: 15
taactcgagc tctgtctcat cacgtcgg                                         28
```

-continued

```
SEQ ID NO: 16            moltype = DNA   length = 32
FEATURE                  Location/Qualifiers
misc_feature             1..32
                         note = primer
source                   1..32
                         mol_type = other DNA
                         organism = synthetic construct
SEQUENCE: 16
ttaggatcca aattgcagtc ataggagtct tc                            32

SEQ ID NO: 17            moltype = DNA   length = 29
FEATURE                  Location/Qualifiers
misc_feature             1..29
                         note = primer
source                   1..29
                         mol_type = other DNA
                         organism = synthetic construct
SEQUENCE: 17
taactcgaga gtacgttgac gtgctctga                                29

SEQ ID NO: 18            moltype = DNA   length = 29
FEATURE                  Location/Qualifiers
misc_feature             1..29
                         note = primer
source                   1..29
                         mol_type = other DNA
                         organism = synthetic construct
SEQUENCE: 18
ttaggatccg tgggttaaac aactgcaaa                                29

SEQ ID NO: 19            moltype = DNA   length = 33
FEATURE                  Location/Qualifiers
misc_feature             1..33
                         note = primer
source                   1..33
                         mol_type = other DNA
                         organism = synthetic construct
SEQUENCE: 19
taactcgagg gttaaagtct tctatcctcc tgg                           33

SEQ ID NO: 20            moltype = DNA   length = 31
FEATURE                  Location/Qualifiers
misc_feature             1..31
                         note = primer
source                   1..31
                         mol_type = other DNA
                         organism = synthetic construct
SEQUENCE: 20
ttaggatccg gataaccact gggataatag g                             31

SEQ ID NO: 21            moltype = DNA   length = 30
FEATURE                  Location/Qualifiers
misc_feature             1..30
                         note = primer
source                   1..30
                         mol_type = other DNA
                         organism = synthetic construct
SEQUENCE: 21
taactcgaga gttgtgaaat tccttctgcc                               30

SEQ ID NO: 22            moltype = DNA   length = 29
FEATURE                  Location/Qualifiers
misc_feature             1..29
                         note = primer
source                   1..29
                         mol_type = other DNA
                         organism = synthetic construct
SEQUENCE: 22
ttaggatccc gcagatagaa ccagtgaac                                29

SEQ ID NO: 23            moltype = DNA   length = 28
FEATURE                  Location/Qualifiers
misc_feature             1..28
                         note = primer
source                   1..28
                         mol_type = other DNA
                         organism = synthetic construct
SEQUENCE: 23
```

```
taactcgagc agcagctcta cttgggtc                                    28

SEQ ID NO: 24          moltype = DNA   length = 27
FEATURE                Location/Qualifiers
misc_feature           1..27
                       note = primer
source                 1..27
                       mol_type = other DNA
                       organism = synthetic construct
SEQUENCE: 24
ttaggatcca ggagggaaag acaggct                                     27

SEQ ID NO: 25          moltype = DNA   length = 25
FEATURE                Location/Qualifiers
misc_feature           1..25
                       note = primer
source                 1..25
                       mol_type = other DNA
                       organism = synthetic construct
SEQUENCE: 25
taactcgagc cctcgccttc ttctg                                       25

SEQ ID NO: 26          moltype = DNA   length = 32
FEATURE                Location/Qualifiers
misc_feature           1..32
                       note = primer
source                 1..32
                       mol_type = other DNA
                       organism = synthetic construct
SEQUENCE: 26
ttaggatccc aaaatagaag gagtgcaaaa ag                               32

SEQ ID NO: 27          moltype = DNA   length = 35
FEATURE                Location/Qualifiers
misc_feature           1..35
                       note = primer
source                 1..35
                       mol_type = other DNA
                       organism = synthetic construct
SEQUENCE: 27
taactcgagc ctggagtttc ttaagtaata gttgc                            35

SEQ ID NO: 28          moltype = DNA   length = 27
FEATURE                Location/Qualifiers
misc_feature           1..27
                       note = primer
source                 1..27
                       mol_type = other DNA
                       organism = synthetic construct
SEQUENCE: 28
ttaggatcca ccggtccagg tcattta                                     27

SEQ ID NO: 29          moltype = DNA   length = 27
FEATURE                Location/Qualifiers
misc_feature           1..27
                       note = primer
source                 1..27
                       mol_type = other DNA
                       organism = synthetic construct
SEQUENCE: 29
taactcgagg cagcaaattc ttcccag                                     27

SEQ ID NO: 30          moltype = DNA   length = 30
FEATURE                Location/Qualifiers
misc_feature           1..30
                       note = primer
source                 1..30
                       mol_type = other DNA
                       organism = synthetic construct
SEQUENCE: 30
ttaggatccc cattccagaa cacactacag                                  30

SEQ ID NO: 31          moltype = DNA   length = 29
FEATURE                Location/Qualifiers
misc_feature           1..29
                       note = primer
source                 1..29
                       mol_type = other DNA
                       organism = synthetic construct
```

```
SEQUENCE: 31
taactcgaga tacctgattt catcatggc                                        29

SEQ ID NO: 32          moltype = DNA   length = 30
FEATURE                Location/Qualifiers
misc_feature           1..30
                       note = primer
source                 1..30
                       mol_type = other DNA
                       organism = synthetic construct
SEQUENCE: 32
ttaggatccc ctttgataag agccaagatg                                       30

SEQ ID NO: 33          moltype = DNA   length = 30
FEATURE                Location/Qualifiers
misc_feature           1..30
                       note = primer
source                 1..30
                       mol_type = other DNA
                       organism = synthetic construct
SEQUENCE: 33
taactcgagt acaaagttat gacgggtcct                                       30

SEQ ID NO: 34          moltype = DNA   length = 28
FEATURE                Location/Qualifiers
misc_feature           1..28
                       note = primer
source                 1..28
                       mol_type = other DNA
                       organism = synthetic construct
SEQUENCE: 34
ttaggatccc aacgaacagg gctaattg                                         28

SEQ ID NO: 35          moltype = DNA   length = 26
FEATURE                Location/Qualifiers
misc_feature           1..26
                       note = primer
source                 1..26
                       mol_type = other DNA
                       organism = synthetic construct
SEQUENCE: 35
taactcgagg accgcttaaa ggccag                                           26

SEQ ID NO: 36          moltype = DNA   length = 29
FEATURE                Location/Qualifiers
misc_feature           1..29
                       note = primer
source                 1..29
                       mol_type = other DNA
                       organism = synthetic construct
SEQUENCE: 36
ttaggatccg tgcatgaaaa tcgaaaatg                                        29

SEQ ID NO: 37          moltype = DNA   length = 31
FEATURE                Location/Qualifiers
misc_feature           1..31
                       note = primer
source                 1..31
                       mol_type = other DNA
                       organism = synthetic construct
SEQUENCE: 37
taactcgagt ggtcttgtgg ctttatagac a                                     31

SEQ ID NO: 38          moltype = DNA   length = 27
FEATURE                Location/Qualifiers
misc_feature           1..27
                       note = primer
source                 1..27
                       mol_type = other DNA
                       organism = synthetic construct
SEQUENCE: 38
ttaggatcca accggaggaa accctac                                          27

SEQ ID NO: 39          moltype = DNA   length = 25
FEATURE                Location/Qualifiers
misc_feature           1..25
                       note = primer
source                 1..25
                       mol_type = other DNA
```

-continued

```
                              organism = synthetic construct
SEQUENCE: 39
taactcgagg taccgcaccg tctgg                                    25

SEQ ID NO: 40            moltype = DNA   length = 27
FEATURE                  Location/Qualifiers
misc_feature             1..27
                         note = primer
source                   1..27
                         mol_type = other DNA
                         organism = synthetic construct
SEQUENCE: 40
ttaggatcca gctaccttgc agcacgt                                  27

SEQ ID NO: 41            moltype = DNA   length = 24
FEATURE                  Location/Qualifiers
misc_feature             1..24
                         note = primer
source                   1..24
                         mol_type = other DNA
                         organism = synthetic construct
SEQUENCE: 41
taactcgagc ccaccatcga cagg                                     24

SEQ ID NO: 42            moltype = DNA   length = 29
FEATURE                  Location/Qualifiers
misc_feature             1..29
                         note = primer
source                   1..29
                         mol_type = other DNA
                         organism = synthetic construct
SEQUENCE: 42
ttaggatccc gagccgtata agtattggc                                29

SEQ ID NO: 43            moltype = DNA   length = 27
FEATURE                  Location/Qualifiers
misc_feature             1..27
                         note = primer
source                   1..27
                         mol_type = other DNA
                         organism = synthetic construct
SEQUENCE: 43
taactcgagc gccggtgaag accttac                                  27

SEQ ID NO: 44            moltype = DNA   length = 32
FEATURE                  Location/Qualifiers
misc_feature             1..32
                         note = primer
source                   1..32
                         mol_type = other DNA
                         organism = synthetic construct
SEQUENCE: 44
ttaggatcca ctactgtcag tcactttgga gc                            32

SEQ ID NO: 45            moltype = DNA   length = 29
FEATURE                  Location/Qualifiers
misc_feature             1..29
                         note = primer
source                   1..29
                         mol_type = other DNA
                         organism = synthetic construct
SEQUENCE: 45
taactcgagt accgggtttg ttgctattt                                29

SEQ ID NO: 46            moltype = DNA   length = 30
FEATURE                  Location/Qualifiers
misc_feature             1..30
                         note = primer
source                   1..30
                         mol_type = other DNA
                         organism = synthetic construct
SEQUENCE: 46
ttaggatccc acaactggta ctgcagagac                               30

SEQ ID NO: 47            moltype = DNA   length = 30
FEATURE                  Location/Qualifiers
misc_feature             1..30
                         note = primer
source                   1..30
```

-continued

```
                        mol_type = other DNA
                        organism = synthetic construct
SEQUENCE: 47
taactcgagg cgtagccctt tgatctatag                                    30

SEQ ID NO: 48          moltype = DNA   length = 26
FEATURE                Location/Qualifiers
misc_feature           1..26
                        note = primer
source                 1..26
                        mol_type = other DNA
                        organism = synthetic construct
SEQUENCE: 48
ttaggatccg gtgctatgcg tgtcgt                                        26

SEQ ID NO: 49          moltype = DNA   length = 29
FEATURE                Location/Qualifiers
misc_feature           1..29
                        note = primer
source                 1..29
                        mol_type = other DNA
                        organism = synthetic construct
SEQUENCE: 49
taactcgaga tctcctacgt ccctgtggg                                     29
```